US009650413B2

(12) United States Patent
Konstantinov et al.

(10) Patent No.: US 9,650,413 B2
(45) Date of Patent: May 16, 2017

(54) INTEGRATED CONTINUOUS MANUFACTURING OF THERAPEUTIC PROTEIN DRUG SUBSTANCES

(71) Applicant: Genzyme Corporation, Cambridge, MA (US)

(72) Inventors: Konstantin Konstantinov, Bridgewater, NJ (US); Rahul Godawat, Bridgewater, NJ (US); Veena Warikoo, Bridgewater, NJ (US); Sujit Jain, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/627,559

(22) Filed: Feb. 20, 2015

(65) Prior Publication Data

US 2015/0232505 A1    Aug. 20, 2015

Related U.S. Application Data

(63) Continuation of application No. 14/195,481, filed on Mar. 3, 2014.

(60) Provisional application No. 61/775,060, filed on Mar. 8, 2013, provisional application No. 61/856,390, filed on Jul. 19, 2013.

(51) Int. Cl.
*C07K 1/22* (2006.01)
*C07K 16/00* (2006.01)
*C12N 9/00* (2006.01)
*C12P 21/00* (2006.01)

(52) U.S. Cl.
CPC ............ *C07K 1/22* (2013.01); *C07K 16/00* (2013.01); *C12N 9/00* (2013.01); *C12P 21/00* (2013.01)

(58) Field of Classification Search
CPC .. C07K 1/22; C07K 16/00; C12N 9/00; C12P 21/00
See application file for complete search history.

(56) References Cited

U.S. PATENT DOCUMENTS

| 4,401,108 A | 8/1983 | Galkin et al. |
| 4,559,175 A | 12/1985 | Paciorek et al. |
| 5,169,936 A | 12/1992 | Staples et al. |
| 5,423,982 A | 6/1995 | Jungbauer et al. |
| 5,571,720 A | 11/1996 | Grandics et al. |
| 5,606,033 A | 2/1997 | Cramer et al. |
| 5,610,285 A | 3/1997 | Lebing et al. |

(Continued)

FOREIGN PATENT DOCUMENTS

| CN | 102321316 | 1/2012 |
| EP | 0281368 | 9/1988 |

(Continued)

OTHER PUBLICATIONS

Muller-Spath et al., Two step capture and purification of IgG2 using multicolumn countercurrent solvent gradient purification (MCSGP)., Biotechnol Bioeng. (2010), vol. 107(6), pp. 974-984.*

(Continued)

*Primary Examiner* — Alexander Kim
(74) *Attorney, Agent, or Firm* — Fish & Richardson P.C.

(57) ABSTRACT

Provided herein are integrated continuous biomanufacturing processes for producing a therapeutic protein drug substance. Also provided are systems that are capable of continuously producing a therapeutic protein drug substance.

37 Claims, 13 Drawing Sheets

(56) References Cited

U.S. PATENT DOCUMENTS

| | | | |
|---|---|---|---|
| 5,856,179 | A | 1/1999 | Chen et al. |
| 6,127,526 | A | 10/2000 | Blank |
| 6,180,401 | B1 | 1/2001 | Chen et al. |
| 6,265,542 | B1 | 7/2001 | Fahrner et al. |
| 6,307,028 | B1 | 10/2001 | Lebing et al. |
| 6,333,398 | B1 | 12/2001 | Blank |
| 6,359,114 | B1 | 3/2002 | Grimes et al. |
| 6,410,270 | B1 | 6/2002 | Strittmatter et al. |
| 6,417,335 | B1 | 7/2002 | Basey et al. |
| 6,489,447 | B1 | 12/2002 | Basey et al. |
| 6,551,512 | B1 | 4/2003 | Britsch et al. |
| 6,660,172 | B2 | 12/2003 | Koslow |
| 6,870,034 | B2 | 3/2005 | Breece et al. |
| 6,902,909 | B2 | 6/2005 | Navran, Jr. et al. |
| 6,955,917 | B2 | 10/2005 | Alred et al. |
| 7,220,356 | B2 | 5/2007 | Thommes et al. |
| 7,323,553 | B2 | 1/2008 | Fahrner et al. |
| 7,531,645 | B2 | 5/2009 | Basey et al. |
| 7,544,784 | B2 | 6/2009 | Sassenfeld et al. |
| 7,553,938 | B2 | 6/2009 | Buchacher et al. |
| 7,662,930 | B2 | 2/2010 | Zhou |
| 7,673,757 | B2 | 3/2010 | Yavorsky |
| 7,714,112 | B2 | 5/2010 | Engstrand et al. |
| 7,759,117 | B2 | 7/2010 | Pham |
| 7,928,205 | B2 | 4/2011 | Dillon et al. |
| 8,044,017 | B2 | 10/2011 | Emery et al. |
| 8,117,924 | B2 | 2/2012 | Joeris |
| RE43,655 | E | 9/2012 | Lebing et al. |
| 8,580,554 | B2 | 11/2013 | Grillberger et al. |
| 2005/0272146 | A1 | 12/2005 | Hodge et al. |
| 2006/0046261 | A1 | 3/2006 | Porter et al. |
| 2006/0183198 | A1 | 8/2006 | Buechler |
| 2007/0244307 | A1 | 10/2007 | Engstrand et al. |
| 2008/0031877 | A1 | 2/2008 | Covacci et al. |
| 2009/0298121 | A1 | 12/2009 | Schwartz et al. |
| 2010/0330627 | A1 | 12/2010 | Shimada et al. |
| 2012/0255642 | A1 | 10/2012 | Gebauer |
| 2013/0061941 | A1 | 3/2013 | Gebauer |
| 2014/0038264 | A1 | 2/2014 | Grillberger et al. |
| 2014/0255994 | A1 | 9/2014 | Konstantinov et al. |
| 2015/0183821 | A1 | 7/2015 | Konstantinov et al. |
| 2015/0202595 | A1 | 7/2015 | Godawat et al. |
| 2015/0203529 | A1 | 7/2015 | Godawat et al. |
| 2015/0203531 | A1 | 7/2015 | Godawat et al. |
| 2015/0203532 | A1 | 7/2015 | Godawat et al. |

FOREIGN PATENT DOCUMENTS

| | | |
|---|---|---|
| EP | 0621074 | 10/1994 |
| EP | 2020433 | 3/2013 |
| EP | 2682168 | 1/2014 |
| WO | WO 91/06008 | 5/1991 |
| WO | WO 92/17403 | 10/1992 |
| WO | WO 94/22490 | 10/1994 |
| WO | WO 02/41989 | 5/2002 |
| WO | 2006/039588 | 4/2006 |
| WO | WO 2006/096116 | 9/2006 |
| WO | 2008/073620 | 6/2008 |
| WO | WO 2008/110291 | 9/2008 |
| WO | 2008/127087 | 10/2008 |
| WO | WO 2011/076386 | 6/2011 |
| WO | WO 2011/078772 | 6/2011 |
| WO | WO 2011/152788 | 12/2011 |
| WO | 2012/078677 | 6/2012 |
| WO | WO 03/045546 | 6/2013 |
| WO | WO 2013/159858 | 10/2013 |
| WO | 2014/004103 | 1/2014 |
| WO | 2014/004281 | 1/2014 |
| WO | WO 2014/137903 | 9/2014 |
| WO | WO 2015/109146 | 7/2015 |
| WO | WO 2015/109151 | 7/2015 |
| WO | WO 2015/109246 | 7/2015 |

OTHER PUBLICATIONS

Muller-Spath et al. (2010) supplemental information.*
Anderson, "Practical use of continuous processing in developing and scaling up laboratory processes," Org. Proc. Res. Dev., 5(6):613-621, 2001.
Bisschops et al., "Single-Use, Continuous-Countercurrent, Multicolumn Chromatography," BioProcess International, Supplement, pp. 18-23, Jun. 1, 2009.
Grabski and Mierendorf, "Simulated moving bed chromatography," Genetic Engineering & Biotechnology News [online], Oct. 15, 2009 [retrieved on Jul. 16, 2014]. Retrieved from the Internet: < URL: http://www.genengnews.com/gen-articles/simulated-moving-bed-chromatography/3076/>, vol. 29, No. 18, 4 pages.
Holzer et al., "Multicolumn Chromatography: A new approach to relieving capacity bottlenecks for downstream processing efficiency," BioProcess International, Retrieved from the Internet: <URL: http://www.novasep.com/upload/news/PDF/3176Multicolumn_Chromatography-BioProcess-Internationa.pdf>, 6 pages, Sep. 2008.
International Search Report and Written Opinion for PCT/US2014/019909 mailed May 21, 2014, 10 pages.
Jayapal et al., "Recombinant protein therapeutics from CHO cells—20 years and counting," CHO Consortium SBE Special Edition pp. 40-47, 2007.
Laird, "Continuous processes in small-scale manufacture," Organic Process Research & Development, 11(6):927, 2007.
Ohashi et al., "Perfusion cell culture in disposable bioreactors," presented at ESACT in 2001, Sweden, 6 pages.
Vogel et al, "Continuous annular chromatography: General characterization and application for the isolation of recombinant protein drugs," Biotechnol Bioeng., 80(5):559-568, Dec. 5, 2002.
Warikoo et al., "Integrated continuous production of recombinant therapeutic proteins," Biotechnol Bioeng., 109(12):3018-3029. Epub Aug. 6, 2012.
Brower, M., et al., "What Can Continuous Processing Do for You?" Biopharmaceutical Development & Production Week Conference, Huntington Beach, CA, Feb. 28, 2013, 27 pages.
Ransohoff, T.C., "The Potential for Continuous Chromatography and DSP in Clinical Manufacturing of Biopharmaceuticals," Biopharmaceutical Development & Production Week Conference, Huntington Beach, CA, Feb. 28, 2013, 29 pages.
Non-final Office Action issued in U.S. Appl. No. 14/645,138 on Sep. 22, 2015, 14 pages.
Non-final Office Action issued in U.S. Appl. No. 14/195,481 on Sep. 22, 2015, 25 pages.
International Preliminary Report on Patentability in International Application No. PCT/US2014/019909, mailed Sep. 17, 2015, 7 pages.
Blank et al., Self-Immobilizing Recombinant antibody Fragments for Immunoaffinity Chromatography: Generic, Parallel, and Scalable Protein Purification, Protein Expression and Purification (2002), vol. 24, pp. 313-322.
Chisti et al., Large Scale Protein Separations: Engineering Aspects of Chromatography., Biotech. Adv. (1990), vol. 8, pp. 699-708.
Shinkazh et al., Countercurrent tangential chromatography for large-scale protein purification., Biotechnol Bioeng. (Mar. 2011), vol. 108(3), pp. 582-591.
U.S. Appl. No. 61/420,066, filed Dec. 6, 2010, Ransohoff et al.
U.S. Appl. No. 61/775,060, filed Mar. 8, 2013, Konstantinov et al.
U.S. Appl. No. 61/856,390, filed Jul. 19, 2013, Konstantinov et al.
U.S. Appl. No. 61/928,906, filed Jan. 17, 2014, Godawat et al.
U.S. Appl. No. 61/928,929, filed Jan. 17, 2014, Godawat et al.
U.S. Appl. No. 62/001,498, filed May 12, 2014, Godawat et al.
"Capto Adhere—Affinity Chromatography," Feb. 20, 2012 (39 pages).
"Method for radiation sterilization of sensitive chromatographic resins and membranes," IP.com No. IPCOM000188023D (Sep. 18, 2009).

(56) References Cited

OTHER PUBLICATIONS

"Multimodal Chromatography- Handbook GE Healthcare Life Sciences imagination at work Multimodal Chromatography Handbook," Nov. 2013.
Berthod et al., Analytical Separation Science, First Edition, 2015, Wiley-VCH Verlag GmbH & Co., Edited by Jared L. Anderson, Alain Berthod, Veronica Pino Estevez, and Apryll M. Stalcup, pp. 1177-1206.
Database WPI Thomson Scientific, London, GB; RU 2034853 Abstract; May 10, 1995.
Degenhardt et al., "Separation and Purification of Anthocyanins by High-Speed Countercurrent Chromatography and Screening for Antioxidant Activity," *J. Agricultural Food Chem.* 48(2):338-343 (Jan. 13, 2000).
Ferre et al., "Purification of correctly oxidized MHC class I heavy-chain molecules under denaturing conditions: A novel strategy exploiting disulfide assisted protein folding," *Protein Sci.* 12:551-559 (2003).
Final Office Action issued in U.S. Appl. No. 14/629,356, on Feb. 10, 2016, 13 pages.
Final Office Action issued in U.S. Appl. No. 14/629,315, on Mar. 8, 2016.
Final Office Action issued in U.S. Appl. No. 14/645,138, on Feb. 18, 2016, 17 pages.
First Third-Party Submission under 37 CFR 1.290 and Concise Description of Relevance filed in U.S. Appl. No. 14/598,401, filed Nov. 2, 2015 (16 pages).
Gagnon, P., "Dissection of the Separation Mechanisms and Enhancement of Aggregate Removal by Charged-Hydrophobic Mixed Mode Chromatography," $6^{th}$ International Symposium on HIC and RPC, mar. 16-19, 2009, 30 pages.
GE Healthcare, "Ion Exchange Chromatography & Chromatofocusing Principles and Methods, Ion Exchange Chromatography & Chromatofocusing—Principles and Methods imagination at work," Apr. 2010.
GE Healthcare, "Use of sodium hydroxide for cleaning and sanitizing chromatography media and systems," Application Note 18-1124-57 AF Process Chromatography, Sep. 2006, pp. 1-8.
Gil et al., "Challenging the Cleanroom Paradigm for Biopharmaceutical Manufacturing of Bulk Drug Substances," *BioPharm Int.* pp. 1-8, Aug. 1, 2011.
Guide to Irradiation and Sterilization Validation of Single-Use Bioprocess Systems, BioProcess International, May 2008: 10S-22S.
International Preliminary Report on Patentability in International Patent Application No. PCT/US2015/011705, issued Jul. 19, 2016, 11 pages.
International Preliminary Report on Patentability in International Patent Application No. PCT/US2015/011698, mailed Jul. 28, 2016, 8 pages.
International Search Report and Written Opinion for PCT/US2015/011698 mailed Apr. 17, 2015, 13 pages.
International Search Report and Written Opinion issued in PCT/US2015/011705 on Apr. 30, 2015 (16 pages).
Kostova et al., "Preparative Chromatographic Separation of Amino Acid Racemic Mixtures. Absorption Isotherms" *Separation Purification Technol.* 54(3):340-348 (2007).
Moore et al., "Protection of Protein A Sepharose Columns Irradiated to Sterilization Doses," *Radiat. Phys. Chem.* 47(1):161-165 (1996).
Ng et al., "Regeneration Studies of Anion-Exchange Chromatography Resins," Bioprocess Int. 5(5):52-56 (May 2007).
Non-Final Office Action issued in U.S. Appl. No. 14/629,356, on Aug. 29, 2016, 15 pages.
Non-final Office Action issued in U.S. Appl. No. 14/598,401, on Apr. 19, 2016, 7 pages.
Non-final Office Action issued in U.S. Appl. No. 14/195,481, on Apr. 29, 2016, 50 pages.
Non-final Office Action issued in U.S. Appl. No. 14/629,315, on Oct. 20, 2015.
Non-final Office Action issued in U.S. Appl. No. 14/629,356 on Jul. 17, 2015 (16 pages).
Non-final Office Action issued in U.S. Appl. No. 14/629,315, on May 19, 2015.
Rosset, AJ, Neuzil, RW, and Broughton, DB. Industrial application of preparative chromatography in Rodrigues AE, Tondeur D (eds.), Percolation Processes: Theory and Application, Rockville, MD, Sijthoff & Noordhoff Press, 1981.
Second Third-Party Submission under 37 CFR 1.290 and Concise Description of Relevance filed in U.S. Appl. No. 14/598,401, filed Nov. 2, 2015 (21 pages).
Styskin et al., "Gas Chromatography of Phenolic Antioxidants," *J. Chromatography* 77(1):11-19 (1973).
Third-Party Submission under 37 CFR 1.290 and Concise Description of Relevance filed in U.S. Appl. No. 14/598,401, filed Dec. 3, 2015 (16 pages).
Third-Party Submission under 37 CFR 1.290 and Concise Description of Relevance filed in U.S. Appl. No. 14/598,450, filed Nov. 5, 2015 (12 pages).
Third-Party Submission under 37 CFR 1.290 and Concise Description of Relevance filed in U.S. Appl. No. 14/598,450, filed Nov. 2, 2015 (21 pages).
Tricorn column last viewed Sep. 17, 2015, 1 page.
Written Opinion in Singapore Patent Application No. 11201506775V, dated Aug. 16, 2016, 6 pages.
Zbikowska et al., "Protein modification caused by a high dose of gamma irradiation in cryosterilized plasma: Protective effects of ascorbate," *Free Rad. Biol. & Med.* 40:536-542, Oct. 14, 2005.

* cited by examiner

INTEGRATED CONTINUOUS MANUFACTURING OF THERAPEUTIC PROTEIN DRUG SUBSTANCES

CROSS-REFERENCE TO RELATED APPLICATIONS

This application is a continuation of U.S. patent application Ser. No. 14/195,481, filed Mar. 3, 2014, which claims priority to U.S. Provisional Patent Application Ser. No. 61/775,060, filed Mar. 8, 2013, and U.S. Provisional Patent Application Ser. No. 61/856,390, filed Jul. 19, 2013, the entire contents of these applications are herein incorporated by reference.

TECHNICAL FIELD

This invention relates to methods of biotechnology and the biomanufacturing of recombinant proteins.

BACKGROUND

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic protein drug substances.

SUMMARY

The present invention is based, at least in part, on the discovery that integrated, continuous systems that include two multi-column chromatography systems can be used to continuously produce therapeutic protein drug substances. In view of this discovery, provided herein are integrated and continuous processes for manufacturing a therapeutic protein drug substance that include providing a liquid culture medium containing a recombinant therapeutic protein that is substantially free of cells, where the liquid culture medium is fed into a first multi-column chromatography system (MCCS1); capturing the recombinant therapeutic protein in the liquid culture medium using the MCCS1, where the eluate of the MCCS1 containing the recombinant therapeutic protein is continuously fed into a second multi-column chromatography system (MCCS2); and purifying and polishing the recombinant therapeutic protein using the MCCS2, where the eluate from the MCCS2 is a therapeutic protein drug substance; and where the process is integrated and runs continuously from the liquid culture medium to the eluate from the MCCS2 that is the therapeutic protein drug substance. Also provided are systems specifically designed to perform any of the processes described herein. For example, provided herein are biological manufacturing systems that include: a first multi-column chromatography system (MCCS) containing an inlet; and a second MCCS including an outlet, where the first and second MCCSs are in fluid communication with each other, and where the manufacturing system is configured such that fluid can be passed into the inlet, through the first and second MCCSs, and exit the manufacturing system through the outlet.

Provided herein are integrated and continuous processes for manufacturing a therapeutic protein drug substance that include: (i) providing a liquid culture medium containing a recombinant therapeutic protein that is substantially free of cells, where the liquid culture medium is fed into a first multi-column chromatography system (MCCS1); (ii) capturing the recombinant therapeutic protein in the liquid culture medium using the MCCS1, where the eluate of the MCCS1 containing the recombinant therapeutic protein is continuously fed into a second multi-column chromatography system (MCCS2); and (iii) purifying and polishing the recombinant therapeutic protein using the MCCS2, where the eluate from the MCCS2 is a therapeutic protein drug substance; and where the process is integrated and runs continuously from the liquid culture medium to the eluate from the MCCS2 that is the therapeutic protein drug substance. In some embodiments of any of the processes described herein, the liquid culture medium is selected from the group of: liquid culture medium removed from a perfusion bioreactor containing a culture of mammalian cells that secrete the recombinant therapeutic protein, liquid culture medium removed from a fed-batch bioreactor containing a culture of mammalian cells that secrete the recombinant therapeutic protein, and a clarified liquid culture medium from a culture of bacteria or yeast cells that secrete the recombinant therapeutic protein.

In some embodiments of any of the processes described herein, the MCCS1 and/or the MCCS2 performs at least two different unit operations. In some embodiments of any of the processes described herein, the use of the MCCS1 or the MCCS2, or both, involves column switching. In some embodiments of any of the processes described herein, the MCCS1 performs the unit operations of capturing the recombinant therapeutic protein and inactivating viruses. In some embodiments of any of the processes described herein, the MCCS2 performs the unit operations of purifying and polishing the recombinant therapeutic protein. In some embodiments of any of the processes described herein, the MCCS1 and/or the MCCS2 ultilizes at least two chromatography columns. In some embodiments of any of the processes described herein, the MCCS1 and/or the MCCS2 ultilizes at least two chromatographic membranes. In some embodiments of any of the processes described herein, the MCCS1 and/or the MCCS2 utilizes at least one chromatography column and at least one chromatographic membrane. In some embodiments of any of the processes described herein, the liquid culture medium is liquid culture medium removed from a perfusion bioreactor containing a culture of mammalian cells that secrete the recombinant therapeutic protein.

In some embodiments of any of the processes described herein, the MCCS1 is a first periodic counter current chromatography system (PCCS1). In some embodiments of any of the processes described herein, the PCCS1 includes a four-column PCCS. In some embodiments of any of the processes described herein, three of the four columns in the four-column PCCS perform the unit operation of capturing the recombinant therapeutic protein from the liquid culture medium. In some embodiments of any of the processes described herein, the capturing is performed using affinity chromatography, cation exchange chromatography, anion exchange chromatography, or molecular sieve chromatography. In some embodiments of any of the processes described herein, the affinity chromatography is performed with a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some embodiments of any of the processes described herein, the affinity chromatography is performed with a protein-A binding capture mechanism, and the recombinant therapeutic protein is an antibody or an antibody fragment. In some embodiments of any of the processes described herein, the eluate containing the recombinant therapeutic protein from the three of the four columns in the four-column PCCS is fed into the fourth column of the four-column PCCS. In some embodiments of any of the processes described herein, the fourth column of the four-column PCCS performs the unit operation of inactivating viruses by holding the eluate containing recombinant therapeutic protein at a low pH for viral inactivation. In some embodiments of any of the processes described herein, the fourth column of the four-column PCCS holds the eluate containing the recombinant therapeutic protein at a low pH for viral inactivation for a period of about 10 minutes to about 1.5 hours.

In some embodiments of any of the processes described herein, the MCCS2 is a second periodic counter current (PCCS2) chromatography system. Some embodiments of any of the processes described herein further include adjusting the pH of the eluate from the fourth column of the four-column PCCS using an in-line buffer adjustment reservoir before the eluate from the fourth column of the four-column PCCS is fed into the PCCS2. In some embodiments of any of the processes described herein, the PCCS2 chromatography system includes a three chromatography columns and a chromatographic membrane. In some embodiments of any of the processes described herein, the three chromatography columns in the PCCS2 perform the unit operation of purifying the recombinant therapeutic protein from the eluate of the PCCS1 through cation or anion exchange chromatography. In some embodiments of any of the processes described herein, the eluate from the three chromatography columns in the PCCS2 is fed into the chromatographic membrane in the PCCS2. In some embodiments of any of the processes described herein, the chromatographic membrane in the PCCS2 performs the unit function of polishing the recombinant therapeutic protein present in the eluate from the three chromatography columns in the PCCS2 through cation or anion exchange chromatography. In some embodiments of any of the processes described herein, the chromatographic membrane in the PCCS2 performs the unit function of polishing through cation exchange chromatography. In some embodiments of any of the processes described herein, the flow through and wash of the chromatographic membrane is the therapeutic protein drug substance. Some embodiments of any of the processes described herein further include formulating the therapeutic protein drug substance into a pharmaceutical composition.

In some embodiments of any of the processes described herein, the recombinant therapeutic protein is an antibody or antibody fragment, an enzyme, an engineered protein, or an immunogenic protein or protein fragment. Some embodiments of any of the processes described herein further include adjusting the ionic concentration of the eluate from the three columns in the PCCS2 using in-line buffer adjustment before the eluate from the three columns in the PCCS2 is fed into the chromatographic membrane in the PCCS2. Some embodiments of any of the processes described herein further include the use of a break tank (e.g., any break tank described herein) between the PCCS1 and the PCCS2. Some embodiments of any of the processes described herein further include filtering the eluate from the PCCS1 before it is fed into the PCCS2. Some embodiments of any of the methods described herein further include filtering the liquid culture medium before it is fed into the MCCS1.

Also provided are integrated and continuous processes for manufacturing a therapeutic protein drug substance that include: (i) culturing mammalian cells that secrete a recombinant therapeutic protein in a perfusion bioreactor that contains a liquid culture medium, where a volume of the liquid culture medium that is substantially free of cells is continuously or periodically removed from the perfusion bioreactor and fed into a first multi-column chromatography system (MCCS1); (ii) capturing the recombinant therapeutic protein in the removed liquid culture medium using the MCCS1, where the eluate of the MCCS1 containing the recombinant therapeutic protein is continuously fed into a second multi-column chromatography system (MCCS2); and (iii) purifying and polishing the therapeutic recombinant protein in the eluate of the MCCS1 using the MCCS2, where the eluate from the MCCS2 is a therapeutic protein drug substance; where the process is integrated and runs continuously from the removed liquid culture medium to the eluate from the MCCS2 that is the therapeutic protein drug substance.

In some embodiments of any of the processes described herein, the MCCS1 and/or the MCCS2 performs at least two different unit operations. In some embodiments of any of the processes described herein, the use of the MCCS1 or the MCCS2, or both, involves column switching. In some embodiments of any of the processes described herein, the MCCS1 performs the unit operations of capturing the recombinant therapeutic protein and inactivating viruses. In some embodiments of any of the processes described herein, the MCCS2 performs the unit operations of purifying and polishing the recombinant therapeutic protein. In some embodiments of any of the processes described herein, the MCCS1 and/or the MCCS2 ultilizes at least two chromatography columns. In some embodiments of any of the processes described herein, the MCCS1 and/or the MCCS2 ultilizes at least two chromatographic membranes. In some embodiments of any of the processes described herein, the MCCS1 and/or the MCCS2 utilizes at least one chromatography column and at least one chromatographic membrane.

In some embodiments of any of the processes described herein, the MCCS1 is a first periodic counter current chromatography system (PCCS1). In some embodiments of any of the processes described herein, the PCCS1 includes a four-column PCCS. In some embodiments of any of the processes described herein, three of the four columns in the four-column PCCS perform the unit operation of capturing the recombinant therapeutic protein from the liquid culture medium. In some embodiments of any of the processes described herein, the capturing is performed using affinity chromatography, cation exchange chromatography, anion exchange chromatography, or molecular sieve chromatography. In some embodiments of any of the processes described herein, the affinity chromatography is performed with a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some embodiments of any of the processes described herein, the affinity chromatography is performed with a protein-A binding capture mechanism, and the recombinant therapeutic protein is an antibody or an antibody fragment. In some embodiments of any of the processes described herein, the eluate containing the recombinant therapeutic protein from the three of the four columns in the four-column PCCS is fed into the fourth column of the four-column PCCS. In some embodiments of any of the processes described herein, the fourth column of the four-column PCCS performs the unit operation of inactivating viruses by holding the eluate containing recombinant therapeutic protein at a low pH for viral inactivation. In some embodiments of any of the processes described herein, the fourth column of the four-column PCCS holds the eluate containing the recombinant therapeutic protein at a low pH for viral inactivation for a period of about 10 minutes to about 1.5 hours.

In some embodiments of any of the processes described herein, the MCCS2 is a second periodic counter current (PCCS2) chromatography system. Some embodiments of any of the processes described herein further include adjusting the pH of the eluate from the fourth column of the four-column PCCS using an in-line buffer adjustment reservoir before the eluate from the fourth column of the four-column PCCS is fed into the PCCS2. In some embodiments of any of the processes described herein, the PCCS2 chromatography system includes a three chromatography columns and a chromatographic membrane. In some embodiments of any of the processes described herein, the three chromatography columns in the PCCS2 perform the unit operation of purifying the recombinant therapeutic protein from the eluate of the PCCS1 through cation or anion exchange chromatography. In some embodiments of any of the processes described herein, the eluate from the three chromatography columns in the PCCS2 is fed into the chromatographic membrane in the PCCS2. In some embodiments of any of the processes described herein, the chromatographic membrane in the PCCS2 performs the unit function of polishing the recombinant therapeutic protein present in the eluate from the three chromatography columns in the PCCS2 through cation or anion exchange chromatography. In some embodiments of any of the processes described herein, the chromatographic membrane in the PCCS2 performs the unit function of polishing through cation exchange chromatography. In some embodiments of any of the processes described herein, the flow through and wash of the chromatographic membrane is the therapeutic protein drug substance. Some embodiments of any of the processes described herein further include formulating the therapeutic protein drug substance into a pharmaceutical composition. In some embodiments of any of the processes described herein, the recombinant therapeutic protein is an antibody or antibody fragment, an enzyme, an engineered protein, or an immunogenic protein or protein fragment.

Some embodiments of any of the methods described herein further include adjusting the ionic concentration of the eluate from the three columns in the PCCS2 using in-line buffer adjustment before the eluate from the three columns in the PCCS2 is fed into the chromatographic membrane in the PCCS2. Some embodiments of any of the processes described herein further include the use of a break tank (e.g., any break tank described herein) between the PCCS1 and the PCCS2. Some embodiments of any of the processes described herein further include filtering the eluate from the PCCS1 before it is fed into the PCCS2. Some embodiments of any of the processes described herein further include filtering the liquid culture medium before it is fed into the MCCS1.

Also provided are biological manufacturing system that include: a first multi-column chromatography system (MCCS) including an inlet; and a second MCCS including an outlet, where the first and second MCCSs are in fluid communication with each other, and where the manufacturing system is configured such that fluid can be passed into the inlet, through the first and second MCCSs, and exit the manufacturing system through the outlet. Some embodiments of any of the systems described herein further include a bioreactor, where the bioreactor and the inlet are in fluid communication with each other, and where the manufacturing system is configured such that fluid present in the bioreactor can be passed ino the inlet. In some embodiments of any of the systems described herein, the first MCCS or the second MCCS, or both, is/are configured to perform at least two separate unit operations. In some embodiments of any of the systems described herein, use of the MCCS1 or the MCCS2, or both, involves column switching.

In some embodiments of any of the systems described herein, the first MCCS is configured to perform the unit operations of capturing the recombinant therapeutic protein and inactivating viruses. In some embodiments of any of the systems described herein, the second MCCS is configured to perform the unit operations of purifying and polishing the recombinant therapeutic protein. In some embodiments of any of the systems described herein, the first MCCS or the second MCCS, or both, contain(s) at least two chromatography columns. In some embodiments of any of the systems described herein, the first MCCS or the second MCCS, or both, contain(s) at least two chromatographic membranes. In some embodiments of any of the systems described herein, the first MCCS or the second MCCS, or both, contain(s) at least one chromatography column and at least one chromatographic membrane.

In some embodiments of any of the systems described herein, the first MCCS is a first periodic counter current chromatography system (PCCS1). In some embodiments of any of the systems described herein, the PCCS1 includes a four-column PCCS. In some embodiments of any of the systems described herein, three of the four columns in the four-column PCCS are capable of capturing the recombinant therapeutic protein from the liquid culture medium. In some embodiments of any of the systems described herein, the three of the four columns in the four-column PCCS include one or more of an affinity chromatography column, a cationic chromatography column, an anionic chromatography column, and a molecular sieve chromatography column. In some embodiments of any of the systems described herein, the three of the four columns in the four-column PCCS include one or more of an affinity chromatography column utilizing a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some embodiments of any of the systems described herein, the fourth column of the four-column PCCS is a reservoir or a column that is capable of holding eluate from the three of the four columns of the four-column PCCS containing the recombinant therapeutic protein at low pH for viral inactivation. In some embodiments of any of the systems described herein, the fourth column of the four-column PCCS is capable of holding the eluate containing recombinant therapeutic protein from the three of the four columns of the four-column PCCS at low pH for viral inactivation for a period of about 10 minutes to about 1.5 hours.

In some embodiments of any of the systems described herein, the second MCCS is a second periodic counter current chromatography system (PCCS2). Some embodiments of any of the systems described herein further include a fluid conduit disposed between the first MCCS and the second MCCS. Some embodiments of any of the systems described herein further include an in-line buffer adjustment reservoir in fluid communication with the fluid conduit disposed between the first MCCS and the second MCCS, and configured such that buffer contained within the in-line buffer adjustment reservoir is introduced into the fluid present in the fluid conduit disposed between the first MCCS and the second MCCS. Some embodiments of any of the systems described herein further include a filter disposed in the fluid conduit between the first MCCS and the second MCCS, and configured such that the filter is capable of removing particulate matter from the fluid present in the fluid conduit between the first MCCS and the second MCCS.

In some embodiments of any of the systems described herein, the PCCS2 includes three chromatography columns and a chromatographic membrane. Some embodiments of any of the methods described herein further include a fluid conduit disposed between the three chromatography columns in the PCCS2 and the chromatographic membrane in the PCCS2. Some embodiments of any of the systems described herein further include an in-line buffer adjustment reservoir in fluid communication with the fluid conduit disposed between the three chromatography columns in the PCCS2 and the chromatographic membrane in the PCCS2, and configured such that buffer contained within the in-line buffer adjustment reservoir is introduced into the fluid present in the fluid conduit disposed between the three chromatography columns in the PCCS2 and the chromatographic membrane in the PCCS2.

In some embodiments of any of the systems described herein, the three chromatography columns in the PCCS2 are capable of purifying the recombinant therapeutic protein through a cation or anion exchange chromatography. In some embodiments of any of the systems described herein, the chromatographic membrane in the PCCS2 is a cation exchange chromatographic membrane.

Some embodiments of any of the systems described herein further include a fluid conduit between the chromatographic membrane in the PCCS2 and the outlet. Some embodiments of any of the systems described herein further include a filter disposed in the fluid conduit between the chromatographic membrane in the PCCS2 and the outlet, and configured such that the filter is capable of removing particulate matter from the fluid present in the fluid conduit between the chromatographic membrane in the PCCS2 and the outlet. Some embodiments of any of the systems described herein further include a pump system that is in fluid communication with the inlet. In some embodiments of any of the systems described herein, the pump system includes a pump that is capable of pushing the fluid into the inlet. Some embodiments of any of the systems described herein further include a fluid conduit disposed between the pump and the inlet. Some embodiments of any of the systems described herein further include a filter disposed in the fluid conduit between the pump and the inlet, and configured such that the filter is capable of removing particulate matter from the fluid present in the fluid conduit between the pump and the inlet. Some embodiments of any of the systems described herein further include a break tank (e.g., a break tank described herein) disposed in the fluid conduit between the pump and the inlet that is configured such that the break tank is in fluid communication with the fluid conduit between the pump and the inlet, and is capable of storing any fluid present in the fluid conduit that is not able to enter the inlet.

In some embodiments of any of the systems described herein, the first MCCS and the second MCCS are disposed on a skid (e.g., a skid including one or more structures that enable movement). In some embodiments of any of the systems described herein, the first MCCS is disposed on a first skid. In some embodiments of any of the systems described herein, the second MCCS is disposed on a second skid. In some embodiments of any of the systems described herein, the first and second skids each include one or more structures that enable movement. In some embodiments of any of the systems described herein, the entire system is disposed on a skid (e.g., a skid that includes one or more structures that enable movement).

Also provided are biological manufacturing systems that include two or more subsystems, where the two or more subsystems each include: (i) a first multi-column chromatography system (MCCS) comprising an inlet; and (ii) a second MCCS comprising an outlet, where the first and second MCCSs are in fluid communication with each other, and where the manufacturing system is configured such that fluid can be passed into the inlet, through the first and second MCCS, and exit the manufacturing system through the outlet; where the two or more subsystems are configured such that they are each in fluid communication with a single reservoir containing a fluid, and the fluid from the single reservoir passes into the inlet of the two or more subsystems. In some of the embodiments of any of the systems described herein, each of the two or more subsystems is each disposed on its own skid. In some of the embodiments of any of the systems described herein, the skid includes one or more structures that enable movement. In some embodiments of any of the systems described herein, the entire system is disposed on a skid (e.g., a skid that includes one or more structures that enable movement).

As used herein, the word "a" before a noun represents one or more of the particular noun. For example, the phrase "a mammalian cell" represents "one or more mammalian cells."

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "substantially free" means a composition (e.g., a liquid culture medium) that is at least or about 90% free (e.g., at least or about 95%, 96%, 97%, 98%, or at least or about 99% free, or about 100% free) of a specified substance (e.g., a mammalian cell).

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" means the maintenance or proliferation of a mammalian cell under a controlled set of physical conditions.

The term "culture of mammalian cells" means a liquid culture medium containing a plurality of mammalian cells that is maintained or proliferated under a controlled set of physical conditions.

The term "liquid culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a bioreactor can be substantially free of mammalian cells.

The term "animal-derived component free liquid culture medium" means a liquid culture medium that does not contain any components (e.g., proteins or serum) derived from a mammal.

The term "serum-free liquid culture medium" means a liquid culture medium that does not contain a mammalian serum.

The term "serum-containing liquid culture medium" means a liquid culture medium that contains a mammalian serum.

The term "chemically-defined liquid culture medium" is a term of art and means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "agitation" means stirring or otherwise moving a portion of liquid culture medium in a bioreactor. This is performed in order to, e.g., increase the dissolved $O_2$ concentration in the liquid culture medium in a bioreactor. Agitation can be performed using any art known method, e.g., an instrument or propellor. Exemplary devices and methods that can be used to perform agitation of a portion of the liquid culture medium in a bioreactor are known in the art.

The term "therapeutic protein drug substance" means a recombinant protein (e.g., an immunoglobulin, protein fragment, engineered protein, or enzyme) that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell)) and biological contaminants (e.g., viral and bacterial contaminants), and can be formulated into a pharmaceutical agent without any further substantial purification and/or decontamination step.

The term "integrated process" means a process which is performed using structural elements that function cooperatively to achieve a specific result (e.g., the generation of a therapeutic protein drug substance from a liquid culture medium).

The term "continuous process" means a process which continuously feeds fluid through at least a part of the system. For example, in any of the exemplary continuous biological manufacturing systems described herein, a liquid culture medium containing a recombinant therapeutic protein is continuously fed into the system while it is in operation and a therapeutic protein drug substance is fed out of the system. In another example, a continuous process is a process which continuously feeds a liquid culture medium containing a recombinant therapeutic protein from a bioreactor through a first MCCS. Another example of a continuous process is a process which continuously feeds a liquid culture medium containing a recombinant therapeutic protein from a bioreactor through a first and second MCCS. Additional examples include a process which continuously feeds a liquid culture medium containing a recombinant therapeutic protein through a first MCCS, a process that continuously feeds a liquid culture medium containing a recombinant therapeutic protein through a first and second MCCS, or a process that continusouly feeds a fluid containing a recombinant therapeutic protein through a second MCCS.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')2 fragment, or an a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant therapeutic protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant therapeutic protein (e.g., through the use of affinity chromatography). Non-limiting methods for capturing a recombinant therapeutic protein from a liquid culture medium or diluted liquid culture medium are described herein and others are known in the art. A recombinant therapeutic protein can be captured from a liquid culture medium using at least one chromatography column and/or chromatographic membrane (e.g., any of the chromatography columns and/or chromatographic membranes described herein).

The term "purifying" means a step performed to isolate a recombinant therapeutic protein from one or more other impurities (e.g., bulk impurities) or components present in a fluid containing a recombinant therapeutic protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a resin, membrane, or any other solid support that binds either a recombinant therapeutic protein or contaminants (e.g., through the use of affinity chromatography, hydrophobic interaction chromatography, anion or cation exchange chromatography, or molecular sieve chromatography). A recombinant therapeutic protein can be purified from a fluid containing the recombinant therapeutic protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant therapeutic protein that is close to a final desired purity. For example, polishing can be performed by passing a fluid containing the recombinant therapeutic protein through a chromatographic column(s) or membrane absorber(s) that selectively binds to either the target recombinant therapeutic protein or small amounts of contaminants or impurities present in a fluid containing a recombinant therapeutic protein. In such an example, the eluate/filtrate of the chromatographic column(s) or membrane absorber(s) contains the recombinant therapeutic protein.

The term "eluate/filtrate" is a term of art and means a fluid that is emitted from a chromatography column or chromatographic membrane that contains a detectable amount of a recombinant therapeutic protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion bioreactor" means a bioreactor containing a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "clarified liquid culture medium" means a liquid culture medium obtained from a bacterial or yeast cell culture that is substantially free (e.g., at least 80%, 85%, 90%, 92%, 94%, 96%, 98%, or 99% free) of bacteria or yeast cells.

The term "unit operation" is a term of art and means a functional step that can be performed in a process of manufacturing a therapeutic protein drug substance from a liquid culture medium. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant therapeutic protein, and removing unwanted salts.

"Specific productivity rate" or "SPR" is a term of art and as used herein refers to the mass or enzymatic activity of a recombinant therapeutic protein produced per mammalian cell per day. The SPR for a recombinant therapeutic antibody is usually measured as mass/cell/day. The SPR for a recombinant therapeutic enzyme is usually measured as units/cell/day or (units/mass)/cell/day.

"Volume productivity rate" or "VPR" is a term of art and as used herein refers to the mass or enzymatic activity of recombinant therapeutic protein produced per volume of culture (e.g., per L of bioreactor, vessel, or tube volume) per day. The VPR for a recombinant therapeutic antibody is usually measured as mass/L/day. The VPR for a recombinant therapeutic enzyme is usually measured as units/L/day or mass/L/day.

"Skid" is a term of art and as used herein refers to a three-dimensional solid structure that can act as a platform or support for a system described herein. A skid can, if it comprises one or more structures that enable movement (e.g., wheels, rollers, or the like), confer mobility on the system or a portion thereof. Non-limiting examples of skids are described herein. Additional examples of skids are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
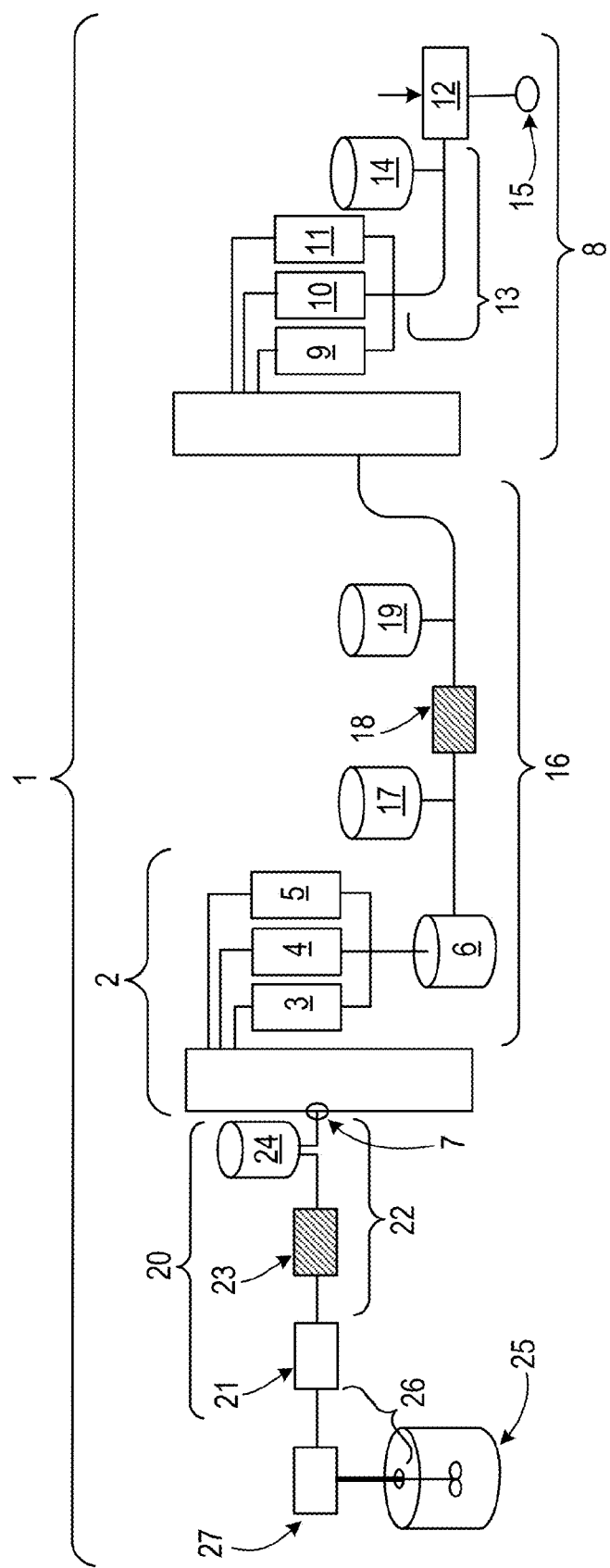
FIG. 1 is a schematic diagram showing an exemplary integrated system that can be used to continuously produce a recombinant protein drug substance.

Provided herein are integrated and fully continuous processes for manufacturing a therapeutic protein drug substance. These processes include, e.g., providing a liquid culture medium containing a recombinant therapeutic protein that is substantially free of cells, then feeding the liquid culture medium into a first multi-column chromatography system (MCCS1). The next step involves capturing the recombinant therapeutic protein in the liquid culture medium using the MCCS1. The next steps involve continuously feeding the eluate of the MCCS1 containing the recombinant therapeutic protein into a second multi-column chromatography system (MCCS2), and purifying and polishing the protein using the MCCS2. The resulting eluate from the MCCS2 is considered a therapeutic protein drug substance. The processes are integrated and can run continuously from the liquid culture medium to the eluate from the MCCS2 that is the therapeutic protein drug substance. Also provided herein are exemplary biological manufacturing systems that can be used to perform these methods.

Biological Manufacturing Systems

The present specification provides exemplary biological manufacturing systems useful for performing the processes described herein. For example, useful systems can include a first multi-column chromatography system (MCCS) that includes an inlet and a second MCCS that includes an outlet. In these systems, the first and second MCCSs are in fluid communication with each other. The systems are also configured such that fluid can be passed into the inlet, through the first and second MCCSs, and exit the manufacturing system through the outlet.

The systems described herein provide for the continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS can be, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the fluid (e.g., a liquid culture medium) containing a therapeutic protein into the first MCCS and eluting a therapeutic protein drug substance (containing the therapeutic protein) from the outlet of the second MCCS is, e.g., greater than about 4 hours and is less than about 40 hours, inclusive, e.g., greater than about 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

Some exemplary systems do not contain a break tank. In others, the system can contain a maximum of 1, 2, 3, 4, or 5 break tank(s) in the entire system. Any of the systems described herein can contain, e.g., a maximum of 1, 2, 3, 4, or 5 break tank(s) in the entire system, where each break tank only holds a therapeutic protein for a total time period of, e.g., between about 5 minutes and about 6 hours, inclusive, e.g., between about 5 minutes and about 5 hours, about 4 hours, about 3 hours, about 2 hours, about 1 hour, or about 30 minutes, inclusive. Break tank(s) described herein can have a capacity that is between 1 mL and about 300 mL, inclusive, between about 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL, inclusive. Any break tank(s) disposed in the system such that fluid enters the break tank(s) prior to entering MCCS1 can have a capacity that is between 1 mL and about 100%, inclusive, e.g., between about 1 mL and about 90%, about 80%, about 70%, about 60%, about 50%, about 40%, about 30%, about 20%, about 10%, or about 5%, inclusive, of the loading volume of the first column of the MCCS1. Any break tanks(s) disposed in the system such that fluid enters the break tank(s) prior to entering the MCCS2 (and after exiting the MCCS1) can have a capacity that is, e.g., between 1 mL and about 100%, inclusive, e.g., between about 1 mL and about 90%, about 80%, about 70%, about 60%, about 50%, about 40%, about 30%, about 20%, about 10%, or about 5%, inclusive, of the loading volume of the first column of the MCCS2.

Exemplary System

A non-limiting example of a system 1 useful in the present invention is provided in FIG. 1. System 1 includes a first MCCS, i.e., a four-column PCCS 2, where three of the four columns 3, 4, and 5 in four-column PCCS 2 perform the unit operation of capturing the recombinant therapeutic protein from a fluid containing the recombinant therapeutic protein (e.g., liquid culture medium that is substantially free of mammalian cells), and one of the columns 6 in PCCS 2 performs the unit operation of inactivating viruses present in the eluate from columns 3, 4, and 5 in PCCS 2 containing the recombinant therapeutic protein. Columns 3, 4, and 5 can contain a resin that utilizes a protein A-binding capture mechanism. Column 6 is capable of holding a fluid at a pH of about 3.75 for about 1 hour. PCCS 1 also has an inlet 7. Inlet 7 can be, e.g., an oriface that accepts entry of a fluid into PCCS 1.

System 1 also includes a second MCCS that is a PPCS 8 that includes three chromatography columns 9, 10, and 11 and one chromatographic membrane 12. Columns 9, 10, and 11 in PCCS 8 can contain a cationic exchange resin. Chromatographic membrane 12 in PCCS 8 can contain a cationic exchange resin. PCCS 8 also has a fluid conduit 13 disposed between columns 9, 10, and 11 in PCCS 8 and chromatographic membrane 12 in PCCS 8. PCCS 8 also has an in-line buffer adjustment reservoir 14 that is in fluid communication with fluid conduit 13, and is configured such that buffer contained within in-line buffer adjustment reservoir 14 is introduced into the fluid present in fluid conduit 13. PCCS 8 also includes an outlet 15. Outlet 15 can be, e.g., an orifice that allows exit of the fluid from PCCS 8.

System 1 may further include a fluid conduit 16 disposed between PCC1 2 and PCC2 8. System 1 may also include an in-line buffer adjustment reservoir 17 in fluid communication with fluid conduit 16 configured such that the buffer contained within in-line buffer adjustment reservoir 17 can be introduced into the fluid present in fluid conduit 16. System 1 may also include a filter 18 disposed in fluid conduit 16 to filter the fluid present in fluid conduit 16. System 1 may also include a second first break tank 19 disposed in fluid conduit 16 and configured to hold any fluid in fluid conduit 11 that cannot be readily fed into PCCS 8.

System 1 may further include a pump system 20 that is in fluid communication with inlet 7. Pump system 20 may include a pump 21 for pushing fluid into inlet 7. System 1 may also include a fluid conduit 22 disposed between pump 21 and inlet 7. System 1 may also include a filter 23 disposed in fluid conduit 22 to filter the fluid (e.g., liquid culture medium) present in fluid conduit 22. System 1 may also include a break tank 24 disposed in fluid conduit 22 configured such that break tank 24 is in fluid communication with fluid conduit 22 and is capable of storing any fluid present in fluid conduit 22 that is not able to enter inlet 7.

System 1 may also include a bioreactor 25 and a fluid conduit 26 disposed between bioreactor 25 and pump 21. A filtration system 27 may be disposed in fluid conduit 26 to filter (e.g., remove cells) from a liquid culture medium present in fluid conduit 26.

Additional Exemplary System Structures and Features

The first MCCS includes an inlet through which fluid (e.g., a liquid culture medium that is substantially free of cells) can be passed into the first MCCS. The inlet can be any structure known in the art for such purposes. It can include, e.g., a threading, ribbing, or a seal that allows for a fluid conduit to be inserted, such that after insertion of the fluid conduit into the inlet, fluid will enter the first MCCS through the inlet without significant seepage of fluid out of the inlet. Non-limiting inlets that can be used in the present systems are known and would be understood by those in the art.

First MCCS

The first MCCS includes at least two chromatography columns, at least two chromatographic membranes, or at least one chromatography column and at least one chromatographic membrane, and an inlet. For example, the first MCCS can include a total of four chromatography columns, or a three chromatography columns and one chromatographic membrane, or any of the other exemplary MCCSs described herein, or have one or more of any of the exemplary features of an MCCS (in any combination) described herein. The chromatography column(s) and/or the chromatographic membrane(s) present in the first MCCS can have one or more of any of the exemplary shapes, sizes, volumes (bed volumes), and/or unit operation(s) described herein.

The chromatography column(s) and/or the chromatographic membrane(s) present in the first MCCS can contain one or more of any of the exemplary resins described herein or known in the art. For example, the resin contained in one or more of the chromatography column(s) and/or chromatographic membrane(s) present in the first MCCS can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin contained in one or more of the chromatography column(s) and/or chromatographic membrane(s) of the first MCCS can be a cation exchange resin, an anion exchange resin, a molecular sieve resin, or a hydrophobic interaction resin, or any combination thereof. Additional examples of resins that can be used to purify a recombinant therapeutic protein are known in the art, and can be contained in one or more of the chromatography column(s) and/or chromatographic membrane(s) present in the first MCCS. The chromatography column(s) and/or chromatography membranes present in the first MCCS can contain the same and/or different resins (e.g., any of the resins described herein or known in the art for use in recombinant protein purification).

The two or more chromatography column(s) and/or chromatographic resin(s) present in the first MCCS can perform one or more unit operations (e.g., capturing a recombinant therapeutic protein, purifying a recombinant therapeutic protein, polishing a recombinant therapeutic protein, inactivating viruses, adjusting the ionic concentration and/or pH of a fluid containing the recombinant therapeutic protein, or filtering a fluid containing a recombinant therapeutic protein). In non-limiting examples, the first MCCS can perform the unit operations of capturing a recombinant therapeutic protein from a fluid (e.g., a liquid culture medium) and inactivating viruses present in the fluid containing the recombinant therapeutic protein. The first MCCS can perform any combinations of two of more unit operations described herein or known in the art.

The chromatography column(s) and/or chromatographic membrane(s) present in the first MCCS can be connected or moved with respect to each other by a switching mechanism (e.g., a column-switching mechanism). The first MCCS can also include one or more (e.g., two, three, four, or five) pumps (e.g., automated, e.g., automated peristaltic pumps). The column-switching events can be triggered by the detection of a level of recombinant therapeutic protein detected by UV absorbance corresponding to a certain level of recombinant therapeutic protein in the fluid passing through the first MCCS (e.g., the input into and/or eluate from one or more of the chromatography column(s) and/or chromatographic membranes in the first MCCS), a specific volume of liquid (e.g., buffer), or specific time elapsed. Column switching generally means a mechanism by which at least two different chromatography columns and/or chromatographic membranes in an MCCS (e.g., two or more different chromatography columns and/or chromatographic membranes present in an MCCS (e.g., the first or second MCCS)) are allowed to pass through a different step (e.g., equilibration, loading, eluting, or washing) at substantially the same time during at least part of the process.

The first MCCS can be a Periodic Counter-Current Chromatography system (PCCS). For example, the PCCS that is the first MCCS can include four chromatography columns, where the first three columns perform the unit operation of capturing a recombinant therapeutic protein from a fluid (e.g., a liquid culture medium), and the fourth column of the PCCS performs the unit operation of inactivating viruses in the fluid containing the recombinant therapeutic protein. A PCCS that is the first MCCS can utilize a column-switching mechanism. The PCC system can utilize a modified ÄKTA system (GE Healthcare, Piscataway, N.J.) capable of running up to, e.g., four, five, six, seven, or eight columns, or more.

The first MCCS can be equipped with: one or more (e.g., two, three, four, five, six, seven, eight, nine, or ten) UV monitors, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The first MCCS can also be equipped with an operating system that utilizes software (e.g., Unicorn-based software, GE Healthcare, Piscataway, N.J.) for sensing when a column-switching should occur (e.g., based upon UV absorbance, volume of liquid, or time elapsed) and affecting (triggering) the column-switching events. In the examples where MCCS includes one or more UV detectors, the UV detectors can be placed optionally at the inlet of one or more (e.g., two, three, four, five, six, seven, eight, nine, or ten) of the chromatography column(s) and/or chromatographic membrane(s) in the first MCCS, and/or at the outlet of one or more of the chromatography column(s) and/or chromatography membrane(s) in the first MCCS.

The first MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the first MCCS can include one or more (e.g., two, three, four, five, or six) break tanks that can hold fluid that cannot readily pass into one or more of the chromatography columns and/or chromatographic membranes in the first MCCS. The systems described herein can contain one or more break tanks (e.g., a break tank described herein) in the first and/or second MCCS. Other examples of the systems described herein do not include a break tank in the first MCCS or the second MCCS, or do not include a break tank in the entire system. Other examples of the systems described herein contain a maximum of one, two, three, four, or five break tank(s) (e.g., any break tank(s) described herein) in the entire system.

Second MCCS

The second MCCS includes at least two chromatography columns, at least two chromatographic membranes, or at least one chromatography column(s) and at least one chromatographic membrane(s), and an outlet. For example, the second MCCS can include a total of four chromatography columns, three chromatography columns and one chromatographic membrane, or any of the other exemplary MCCSs described herein, or can have one or more of any of the exemplary features of an MCCS (in any combination) described herein. The chromatography column(s) and/or the chromatographic membrane(s) present in the second MCCS can have one or more of: any of the shapes, sizes, volumes (bed volumes), and/or unit operations described herein. The chromatography column(s) and/or the chromatographic membrane(s) can contain any of the exemplary resins described herein or known in the art. For example, the resin contained in one or more of the chromatography column(s) and/or chromatographic membrane(s) present in the second MCCS can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). Useful resins include, e.g., a cation exchange resin, an anion exchange resin, a molecular sieve resin, and a hydrophobic interaction resin. Additional examples of resins are known in the art. The chromatography column(s) and/or chromatography membranes present in the second MCCS can contain the same and/or different resins (e.g., any of the resins described herein or known in the art for use in recombinant protein purification).

The chromatography column(s) and/or chromatographic membrane(s) present in the second MCCS can perform one or more unit operations (e.g., any of the unit operations described herein or any combination of the unit operations described herein). In non-limiting examples, the second MCCS can perform the unit operations of purifying a recombinant therapeutic protein from a fluid and polishing the recombinant therapeutic protein present in the fluid containing the recombinant therapeutic protein. In other non-limiting examples, the second MCCS can perform the unit operations of purifying a recombinant therapeutic protein present in a fluid, polishing a recombinant therapeutic protein present in a fluid, and filtering a fluid containing a recombinant therapeutic protein. In another example, the second MCCS can perform the unit operations of purifying a recombinant therapeutic protein present in a fluid, polishing a recombinant therapeutic protein present in a fluid, filtering a fluid containing a recombinant therapeutic protein, and adjusting the ionic concentration and/or pH of a fluid containing a recombinant therapeutic protein. The second MCCS can perform any combination of two of more unit operations described herein or known in the art.

The chromatography column(s) and/or chromatographic membrane(s) present in the second MCCS can be connected or moved with respect to each other by a switching mechanism (e.g., a column-switching mechanism). The second MCCS can also include one or more (e.g., two, three, four, or five) pumps (e.g., automated, e.g., automated peristaltic pumps). The column-switching events can be triggered by the detection of a level of recombinant therapeutic protein detected by UV absorbance corresponding to a certain level of recombinant therapeutic protein in the fluid passing through the second MCCS (e.g., the input into and/or eluate from one or more of the chromatography column(s) and/or chromatographic membranes in the second MCCS), a specific volume of liquid (e.g., buffer), or specific time elapsed.

The second MCCS be a Periodic Counter-Current Chromatography system (PCCS). For example, the PCCS that is the second MCCS can contain three columns that perform the unit operation of purifying a recombinant therapeutic protein from a fluid, and a chromatographic membrane that performs the unit operation of polishing a recombinant therapeutic protein present in a fluid. For example, the three columns that perform the unit operation of purifying a recombinant therapeutic protein from a fluid can contain, e.g., a cationic exchange resin, and the chromatographic membrane that performs the unit operation of polishing can contain a cationic exchange resin. A PCCS that is the second MCCS can utilize a column-switching mechanism. The PCC system can utilize a modified ÄKTA system (GE Healthcare, Piscataway, N.J.) capable of running up to, e.g., four, five, six, seven, or eight columns, or more.

The second MCCS can be equipped with: one or more (e.g., two, three, four, five, six, seven, eight, nine, or ten) UV monitors, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The second MCCS can also be equipped with an operating system that utilizes software (e.g., Unicorn-based softare, GE Healthcare, Piscataway, N.J.) for sensing when a column-switching event should occur (e.g., based upon UV absorbance, volume of liquid, or time elapsed) and affecting the column-switching events. In the examples where the second MCCS includes one or more UV detectors, the UV detectors can be placed optionally at the inlet of one or more (e.g., two, three, four, five, six, seven, eight, nine, or ten) of the chromatography column(s) and/or chromatographic membrane(s) in the second MCCS, and/or at the outlet of one or more of the chromatography column(s) and/or chromatography membrane(s) in the second MCCS.

The second MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the second MCCS can include one or more (e.g., two, three, four, five, or six) break tanks (e.g., any of the break tanks described herein) that can hold fluid that cannot readily pass into one or more of the chromatography columns and/or chromatographic membranes in the second MCCS.

The second MCCS includes an outlet through which the therapeutic protein drug substance can exit the system. The outlet can include, e.g., a threading, ribbing, or a seal that allows for a fluid conduit to be inserted or a vial designed to contain or store the therapeutic protein drug substance. An outlet can contain a surface that can be used to seal a sterile vial or other such storage container onto the outlet in order to allow the recombinant protein drug product to flow directly into the sterile vial or storage container. Non-limiting outlets that can be used in the present systems are known and would be understood by those in the art.

The systems described herein can also include a fluid conduit that is disposed between the first MCCS and the second MCCS. Any of the fluid conduits described herein can be, e.g., a tube that is made of, e.g., polyethylene, polycarbonate, or plastic. The fluid conduit disposed between the first MCCS and the second MCCS can further include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; a break tank (e.g., any of the break tank(s) described herein) that is in fluid communication with the fluid conduit and is positioned such that it can hold any excess fluid present in the fluid conduit that is unable to readily feed into the second MCCS; and one or more filters that are disposed in the fluid conduit such that they are capable of filtering (e.g., removing bacteria) the fluid present in the fluid conduit. Any of the in-line buffer adjustment reservoirs can contain, e.g., a volume of between about 0.5 L to 50 L of buffer (e.g., at a temperature at or below 25° C., 15° C., or 10° C.).

The systems described herein can optionally include a fluid conduit disposed between the final chromatography column or chromatographic membrane in the second MCCS and the outlet. The systems described herein can further include one or more filters in fluid connection with the fluid conduit disposed between the final chromatography column or chromatographic membrane in the second MCCS and the outlet, such that the filter can remove, e.g., precipitated material, particulate matter, or bacteria from the fluid present in the fluid conduit disposed between the final chromatography column or chromatographic membrane in the second MCCS and the outlet.

Some examples of the systems provided herein also include a bioreactor that is in fluid connectivity with the inlet of the first MCCS. Any of the exemplary bioreactors described herein or known in the art can be used in the present systems.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks (e.g., any of the break tanks described herein). Some examples of the systems provided herein further include a fluid conduit disposed between the pump and the inlet of the first MCCS (e.g., any of the exemplary fluid conduits described herein or known in the art). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

Some examples of the systems described herein further include a further fluid conduit connected to the fluid conduit between the pump and the inlet, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system).

The systems provided herein allow for the continuous production of a therapeutic protein drug substance. For example, the systems provided herein allow for a percentage yield of recombinant therapeutic protein (from a starting material, e.g., a starting liquid culture medium) of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The systems described herein can also result in a percentage yield of recombinant therapeutic protein (from a starting material, e.g., a starting liquid culture medium) of between about 80% to about 90%, between about 82% to about 90%, between about 84% to about 90%, between about 84% to about 88%, between about 84% to about 94%, between about 82% to about 92%, or between about 85% to about 95%.

The systems described herein can also result in the production of a therapeutic protein drug substance that contains a concentration of recombinant therapeutic protein that is greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL. As is known in the art, the systems can provide for the periodic elution of a therapeutic protein drug substance. The therapeutic protein drug substance can be eluted from any of the systems described herein for a duration of, e.g., between about 30 seconds and about 5 hours (e.g., between about 1 minute and about 4 hours, between about 1 minute and about 3 hours, between about 1 minute and about 2 hours, between about 1 minute or about 1.5 hours, between about 1 minute and about 1 hour, between about 1 minute and about 30 minutes) at a frequency of, e.g., between about 1 minute and about 6 hours (e.g., between about 1 minute and about 5 hours, between about 1 minute and about 4 hours, between about 1 minute and about 3 hours, between about 1 minute and 2 hours, between about 1 minute and 1 hour, or between about 1 minute and 30 minutes), depending on, e.g., the chromatography column(s) and/or chromatographic membrane(s) used in the first and second MCCS.

The systems described herein can also result in a net yield of recombinant therapeutic protein in the therapeutic protein drug substance of at least about 5 g/day, at least about 6 g/day, at least about 7 g/day, at least about 8 g/day, at least about 9 g/day, at least about 10 g/day, at least about 11 g/day, at least about 12 g/day, at least about 13 g/day, at least about 14 g/day, at least about 15 g/day, at least about 16 g/day, at least about 17 g/day, at least about 18 g/day, at least about 19 g/day, at least about 20 g/day, at least about 25 g/day, at least about 30 g/day, at least about 35 g/day, or at least about 40 g/day over a continuous period of at least about 5 days, at least about 10 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 110 days, at least about 120 days, at least about 130 days, at least about 140 days, at least about 150 days, at least about 160 days, at least about 170 days, at least about 180 days, at least about 190 days, at least about 200 days, at least about 210 days, at least about 220 days, at least about 230 days, at least about 240 days, at least about 250 days, at least about 260 days, at least about 270 days, at least about 280 days, at least about 290 days, at least about 300 days, at least about 310 days, at least about 320 days, at least about 330 days, at least about 340 days, at least about 350 days, or at least about 365 days.

The systems described herein can also continuously produce a recombinant protein drug substance that contains recombinant therapeutic protein having a significantly improved specific productivity rate (as compared to other recombinant protein drug substances prepared by a different process or system). For example, the present systems can achieve a specific productivity rate (in the recombinant protein drug substance) that is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold greater than the specific productivity rate in a recombinant protein drug substance produced using a different process or system (e.g., a batch purification process or a process that is not integrated and/or continuous). The productivity in the recombinant protein drug substance achieved by the present systems can be at least 10,000 units/L, at least 15,000 units/L, at least about 20,000 units/L, at least about 25,000 units/L, at least about 30,000 units/L, at least about 35,000 units/L, or at least about 40,000 units/L (in the first and/or second liquid culture medium). The productivity in the recombinant protein drug substance achieved by the present systems can be at least 1 g/L, at least 1.5 g/L, at least 2.0 g/L, at least 2.5 g/L, at least 3.0 g/L, at least 4.0 g/L, at least 4.5 g/L, or at least 5.0 g/L.

Biological Manufacturing Systems with Two or More Subsystems

Also provided are biological manufacturing systems that include two or more subsystems that each include: (i) a first multi-column chromatography system (MCCS) containing an inlet (e.g., any of the exemplary first MCCSs described herein); and (ii) a second MCCS containing an outlet (e.g., any of the exemplary second MCCSs described herein), where the first and second MCCSs are in fluid communication with each other, and wherein the manufacturing system is configured such that fluid can be passed into the inlet, through the first and second MCCS, and exit the manufacturing system through the outlet; where the two or more subsystems are configured such that they are each in fluid communication with a single reservoir containing a fluid (e.g., a bioreactor), and the fluid from the single reservoir passes into the inlet of the two or more subsystems.

Each of the subsystems can provide for the continuous and time-efficient production of a therapeutic drug substance from a liquid culture medium. For example, the elapsed time for each subsystem, between feeding a fluid (e.g., a liquid culture medium) containing a therapeutic protein into the first MCCS (of the subsystem) and eluting a therapeutic protein drug substance (containing the therapeutic protein) from the outlet of the second MCCS (of the subsystem) can be, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, for each subsystem, the elapsed time between feeding the fluid (e.g., a liquid culture medium) containing a therapeutic protein into the first MCCS (of the subsystem) and eluting a therapeutic protein drug substance (containing the therapeutic protein) from the outlet of the second MCCS (of the subsystem) is, e.g., greater than about 4 hours and is less than about 40 hours, inclusive, e.g., greater than about 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

Some exemplary systems subsystem(s) do not include a break tank. Others include a maximum of 1, 2, 3, 4, or 5 break tanks in the entire subsystem. Any of the subsystem(s) can include a maximum of 1, 2, 3, 4, or 5 break tank(s) in the entire subsystem, where each break tank only holds a therapeutic protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive. Break tank(s) described herein can have a capacity that is, e.g., between 1 mL and about 300 mL, inclusive, e.g., between 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL, inclusive. Any break tank(s) disposed in the subsystem such that fluid enters the break tank(s) prior to entering the MCCS1 (of the subsystem) can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the first MCCS (of the subsystem). Any break tank(s) disposed in the subsystem such that fluid enters the break tank(s) prior to entering the MCCS2 (in any of the subsystem(s)) (and after the fluid exits the MCCS1 of the subsystem) can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the second MCCS (of the subsystem).

Any combination of the features (e.g., type and number of chromatography columns, type and number of chromatographic membranes, volume, size, resin, and unit operation(s), flow rates, pumps, in-line buffer adjustments, UV detectors, one or more filters, and column-switching mechanisms) of the first MCCS and the second MCCS systems described above can be used in the first MCCS and second MCCS in the two or more subsystems. For example, the first MCCS and second MCCS in the two or more subsystems can be substantially the same. In other examples, the two or more subsystems are substantially the same as described in the systems described the Examples.

Skids

Any of the biological manufacturing systems described herein can be disposed on a skid. For example, a system including at least a bioreactor, a first MCCS, and a second MCCS can be disposed on a single skid. In other examples of any of the systems described herein, the first MCCS can be disposed on a first skid and the second MCCS can be disposed on a second skid. Additional examples of any of the systems described herein include a first MCCS and a second MCCS disposed on a single skid, or the entire system disposed on a single skid.

Some examples of the biological manufacturing systems described herein include two or more subsystems that each include: (i) a first multi-column chromatography system (MCCS) containing an inlet (e.g., any of the exemplary first MCCSs described herein); and (ii) a second MCCS containing an outlet (e.g., any of the exemplary second MCCSs described herein), where the first and second MCCSs are in fluid communication with each other, and wherein the manufacturing system is configured such that fluid can be passed into the inlet, through the first and second MCCS, and exit the manufacturing system through the outlet; where the two or more subsystems are configured such that they are each in fluid communication with a single reservoir containing a fluid (e.g., a bioreactor), and the fluid from the single reservoir passes into the inlet of the two or more subsystems. In such systems, the entire system can be disposed on a skid; the reservoir and the one or more subsystems can be on a single skid; each of the two or more subsystems is each disposed on its own skid; or the two or more subsystems can be disposed on a single skid. In any of the systems described herein, a reservoir (e.g., a plastic bag), a break tank (e.g., any of the break tanks described herein), or a bioreactor containing a liquid culture medium containing a recombinant therapeutic protein can be disposed on its own skid.

Non-limiting examples of skids include two or more wheels, a roller, a sled, or a ski that one or more structures that enable movement. As is appreciated by those skilled in the art, skids can be composed of any solid material (e.g., wood, metal, or plastic). Suitable skids can be obtained from Wunderlich-Malec (Minnetonka, Minn.) and Renfrow Brothers (Spartenburg, S.C.). In systems that utilize more than one skid, the skids can be designed to fit together (e.g., fit together via a latch, turn-key, screw, or clamp device).

Integrated and Continuous Processes for Manufacturing a Therapeutic Protein Drug Substance Provided herein are integrated and continuous processes for manufacturing a therapeutic protein drug substance. These processes include providing a liquid culture medium containing a recombinant therapeutic protein that is substantially free of cells, where the liquid culture medium is fed into a first multi-column chromatography system (MCCS1); capturing the recombinant therapeutic protein in the liquid culture medium using the MCCS1, where the eluate of the MCCS1 containing the recombinant therapeutic protein is continuously fed into a second multi-column chromatography system (MCCS2); and purifying and polishing the recombinant therapeutic protein using the MCCS2, where the eluate from the MCCS2 is a therapeutic protein drug substance, and the process is integrated and runs continuously from the liquid culture medium to the eluate from the MCCS2 that is the therapeutic protein drug substance.

The processes described herein provide continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the second MCCS can be, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the fluid (e.g., a liquid culture medium) containing a therapeutic protein into the MCCS1 and eluting a therapeutic protein drug substance (containing the therapeutic protein) from the MCCS2 is, e.g., greater than about 4 hours and less than about 40 hours, inclusive, e.g., greater than about 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

Some exemplary processes do not utilize a holding step (e.g., do not use a reservoir (e.g., break tank) in the entire process). Others may use a maximum of 1, 2, 3, 4, or 5 reservoir(s) (e.g., break tank(s)) in the entire process. Any of the processes described herein can utilize a maximum of 1, 2, 3, 4, or 5 reservoir(s) (e.g., break tank(s)) in the entire process, where each break tank only holds a therapeutic protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive. Any of the reservoir(s) (e.g., break tank(s)) used in the processes described herein can have a capacity that is, e.g., between 1 mL and about 300 mL, inclusive, e.g., between 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive). Any reservoir(s) (e.g., break tank(s)) used (in any of the processes described herein) to hold fluid before before it enters into the first MCCS can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the first MCCS. Any of the reservoir(s) (e.g., break tanks(s)) used (in any of the processes described herein) to hold fluid before it enters into the second MCCS (and after the fluid leaves the first MCCS) can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the second MCCS.

Various additional aspects of these processes are described in detail below and can be used in any combination in the processes provided herein without limitation. Exemplary aspects of the provided processes are described below; however, one skilled in the art will appreciate that additional steps can be added to the processes described herein and other materials can be used to perform any of the steps of the processes described herein.

Liquid Culture Medium

Liquid culture medium that contains a recombinant therapeutic protein that is substantially free of cells can be derived from any source. For example, the liquid culture medium can be obtained from a recombinant cell culture (e.g., a recombinant bacterial, yeast, or mammalian cell culture). The liquid culture medium can be obtained from a fed-batch cell (e.g., mammalian cell) culture (e.g., a fed-batch bioreactor containing a culture of mammalian cells that secrete the recombinant therapeutic protein) or a perfusion cell (e.g., mammalian cell) culture (e.g., a perfusion bioreactor containing a culture of mammalian cells that secrete the recombinant therapeutic protein). The liquid culture medium can also be a clarified liquid culture medium from a culture of bacterial or yeast cells that secrete the recombinant therapeutic protein.

Liquid culture medium obtained from a recombinant cell culture can be filtered or clarified to obtain a liquid culture medium that is substantially free of cells and/or viruses. Methods for filtering or clarifying a liquid culture medium in order to remove cells are known in the art (e.g., 0.2-μm filtration and filtration using an Alternating Tangential Flow (ATF™) system). Recombinant cells can also be removed from liquid culture medium using centrifugation and removing the supernatant that is liquid culture medium that is substantially free of cells, or by allowing the cells to settle to the gravitational bottom of a container (e.g., bioreactor) containing the liquid culture medium, and removing the liquid culture medium (the liquid culture medium that is substantially free of cells) that is distant from the settled recombinant cells.

The liquid culture medium can be obtained from a culture of recombinant cells (e.g., recombinant bacteria, yeast, or mammalian cells) producing any of the recombinant therapeutic proteins described herein. Some examples of any of the processes described herein can further include a step of culturing recombinant cells (e.g., recombinant bacteria, yeast, or mammalian cells) that produce the recombinant therapeutic protein.

The liquid culture medium can be any of the types of liquid culture medium described herein or known in the art. For example, the liquid culture medium can be selected from the group of: animal-derived component free liquid culture medium, serum-free liquid culture medium, serum-containing liquid culture medium, chemically-defined liquid culture medium, and protein-free liquid culture medium. In any of the processes described herein, a liquid culture medium obtained from a culture can be diluted by addition of a second fluid (e.g., a buffer) before it is fed into the first MCCS (e.g., first PCCS).

The liquid culture medium containing a recombinant therapeutic protein that is substantially free of cells can be stored (e.g., at a temperature below about 15° C. (e.g., below about 10° C., below about 4° C., below about 0° C., below about −20° C., below about −50° C., below about −70° C., or below about −80° C.) for at least 1 day (e.g., at least about 2 days, at least about 5 days, at least about 10 days, at least about 15 days, at least about 20 days, or at least about 30 days) prior to feeding the liquid culture medium into the first MCCS (e.g., first PCCS). Alternatively, in some examples the liquid culture medium is fed into the first MCCS (e.g., first PCCS) directly from a bioreactor (e.g., fed into the first MCCS (e.g., first PCCS) directly from the bioreactor after a filtering or clarification step).

Recombinant Therapeutic Proteins

Non-limiting examples of recombinant therapeutic proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant therapeutic antibodies that can be produced by the methods described herein are known in the art. Additional non-limiting examples of recombinant therapeutic proteins that can be produced by the present methods include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factov VIII, factor VIIa, anti-thrombin III, protein C, human albumin, erythropoietin, granulocyte colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Additional examples of recombinant proteins that can be produced by the present methods include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

A secreted, soluble recombinant therapeutic protein can be recovered from the liquid culture medium (e.g., a first and/or second liquid culture medium) by removing or otherwise physically separating the liquid culture medium from the cells (e.g., mammalian cells). A variety of different methods for removing liquid culture medium from cells (e.g., mammalian cells) are known in the art, including, for example, centrifugation, filtration, pipetting, and/or aspiration. The secreted recombinant therapeutic protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

Multi-Column Chromatography Systems

The processes described herein include the use of two or more (e.g., two, three, four, five, or six) multi-column chromatography systems (MCCSs). A MCCS can include two or more chromatography columns, two or more chromatographic membranes, or a combination of at least one chromatography column and at least one chromatographic membrane. In non-limiting examples, a MCCS (e.g., the first and/or second MCCS described in any of the processes herein) can include four chromatographic columns, three chromatographic columns and a chromatographic membrane, three chromatographic columns, two chromatographic columns, two chromatographic membranes, and two chromatographic columns and one chromatographic membrane. Additional examples of combinations of chromatography columns and/or chromatographic membranes can be envisioned for use in an MCCS (e.g., a first and/or second MCCS) by one skilled in the art without limitation. The individual chromatography columns and/or chromatographic membranes present in a MCCS can be identical (e.g., have the same shape, volume, resin, capture mechanism, and unit operation), or can be different (e.g., have one or more of a different shape, volume, resin, capture mechanism, and unit operation). The individual chromatography column(s) and/or chromatographic membrane(s) present in a MCCS (e.g., the first and/or second MCCS) can perform the same unit operation (e.g., the unit operation of capturing, purifying, or polishing) or different unit operations (e.g., different unit operations selected from, e.g., the group of capturing, purifying, polishing, inactivating viruses, adjusting the ionic concentration and/or pH of a fluid containing the recombinant therapeutic protein, and filtering).

The one or more chromatography column(s) that can be present in an MCCS (e.g., present in the first and/or second MCCS) can have a resin volume of, e.g., at least about 2 mL, at least about 5 mL, at least about 10 mL, at least about 15 mL, at least about 20 mL, at least about 25 mL, at least about 30 mL, at least about 35 mL, at least about 40 mL, at least about 45 mL, at least about 50 mL, at least about 55 mL, at least about 60 mL, at least about 65 mL, at least about 70 mL, at least about 75 mL, at least about 80 mL, at least about 85 mL, at least about 90 mL, at least about 95 mL, or at least about 100 mL. The one or more chromatography column(s) that can be present in an MCCS (e.g., present in the first and/or second MCCS) can have a resin volume of between about 2 mL to about 100 mL, between about 2 mL and about 90 mL, between about 2 mL and about 80 mL, between about 2 mL and about 70 mL, between about 2 mL and about 60 mL, between about 2 mL and about 50 mL, between about 5 mL and about 50 mL, between about 2 mL and about 45 mL, between about 5 mL and about 45 mL, between about 2 mL and about 40 mL, between about 5 mL and about 40 mL, between about 2 mL and about 35 mL, between about 5 mL and about 35 mL, between about 2 mL and about 30 mL, between about 5 mL and about 30 mL, between about 2 mL and about 25 mL, between about 5 mL and about 25 mL, between about 15 mL and about 60 mL, between about 10 mL and about 60 mL, between about 10 mL and about 50 mL, and between about 15 mL and about 50 mL. The one or more chromatography column(s) in an MCCS (e.g., the first and/or second MCCS) used in any of the processes described herein can have the substantially the same resin volume or can have different resin volumes. The flow rate used for the one or more chromatography column (s) in an MCCS (e.g., the first and/or second MCCS) can be, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute).

The one or more chromatography column (s) in an MCCS (e.g., the first and/or second MCCS) can have substantially the same shape or can have substantially different shapes. For example, the one or more chromatography column(s) in an MCCS (e.g., in the first and/or second MCCS) can have substantially the shape of a circular cylinder or can have substantially the same shape of an oval cylinder.

The one or more chromatographic membrane(s) that can be present in an MCCS (e.g., present in the first and/or second MCCS) can have a bed volume of, e.g., between about 1 mL to about 500 mL (e.g., between about 1 mL to about 475 mL, between about 1 mL to about 450 mL, between about 1 mL to about 425 mL, between about 1 mL to about 400 mL, between about 1 mL to about 375 mL, between about 1 mL to about 350 mL, between about 1 mL to about 325 mL, between about 1 mL to about 300 mL, between about 1 mL to about 275 mL, between about 1 mL to about 250 mL, between about 1 mL to about 225 mL, between about 1 mL to about 200 mL, between about 1 mL to about 175 mL, between about 1 mL to about 150 mL, between about 1 mL to about 125 mL, between about 1 mL to about 100 mL, between about 2 mL to about 100 mL, between about 5 mL to about 100 mL, between about 1 mL to about 80 mL, between about 2 mL to about 80 mL, between about 5 mL to about 80 mL, between about 1 mL to about 60 mL, between about 2 mL to about 60 mL, between about 5 mL to about 60 mL, between about 1 mL to about 40 mL, between about 2 mL to about 40 mL, between about 5 ml, to about 40 mL, between about 1 mL to about 30 mL, between about 2 mL to about 30 mL, between about 5 mL to about 30 mL, between about 1 mL and about 25 mL, between about 2 mL and about 25 mL, between about 1 mL and about 20 mL, between about 2 mL and about 20 mL, between about 1 mL and about 15 mL, between about 2 mL and about 15 mL, between about 1 mL and about 10 mL, or between about 2 mL and about 10 mL.

One or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the two or more MCCSs in any of the processes described herein. As is known in the art, the one or more types of buffer used in the two or more MCCSs used in the processes described herein will depend on the resin present in the chromatography column(s) and/or the chromatographic membrane(s) of the two or more MCCSs (e.g., the first and second MCCSs), the recombinant therapeutic protein, and unit operation (e.g., any of the exemplary unit operations described herein) performed by the specific chromatography column(s) and/or chromatography membranes of the two or more MCCSs. The volume and type of buffer employed during the use of the two or more MCCSs in any of the processes described herein can also be determined by one skilled in the art (e.g., discussed in more detail below). For example, the volume and type(s) of buffer employed during the use of the two or more MCCSs in any of the processes described herein can be chosen in order to optimize one or more of the following in the recombinant protein drug product: the overall yield of recombinant therapeutic protein, the activity of the recombinant therapeutic protein, the level of purity of the recombinant therapeutic protein, and the removal of biological contaminants from a fluid containing the recombinant therapeutic protein (e.g., absence of active viruses, mycobacteria, yeast, bacteria, or mammalian cells).

Figure 3:
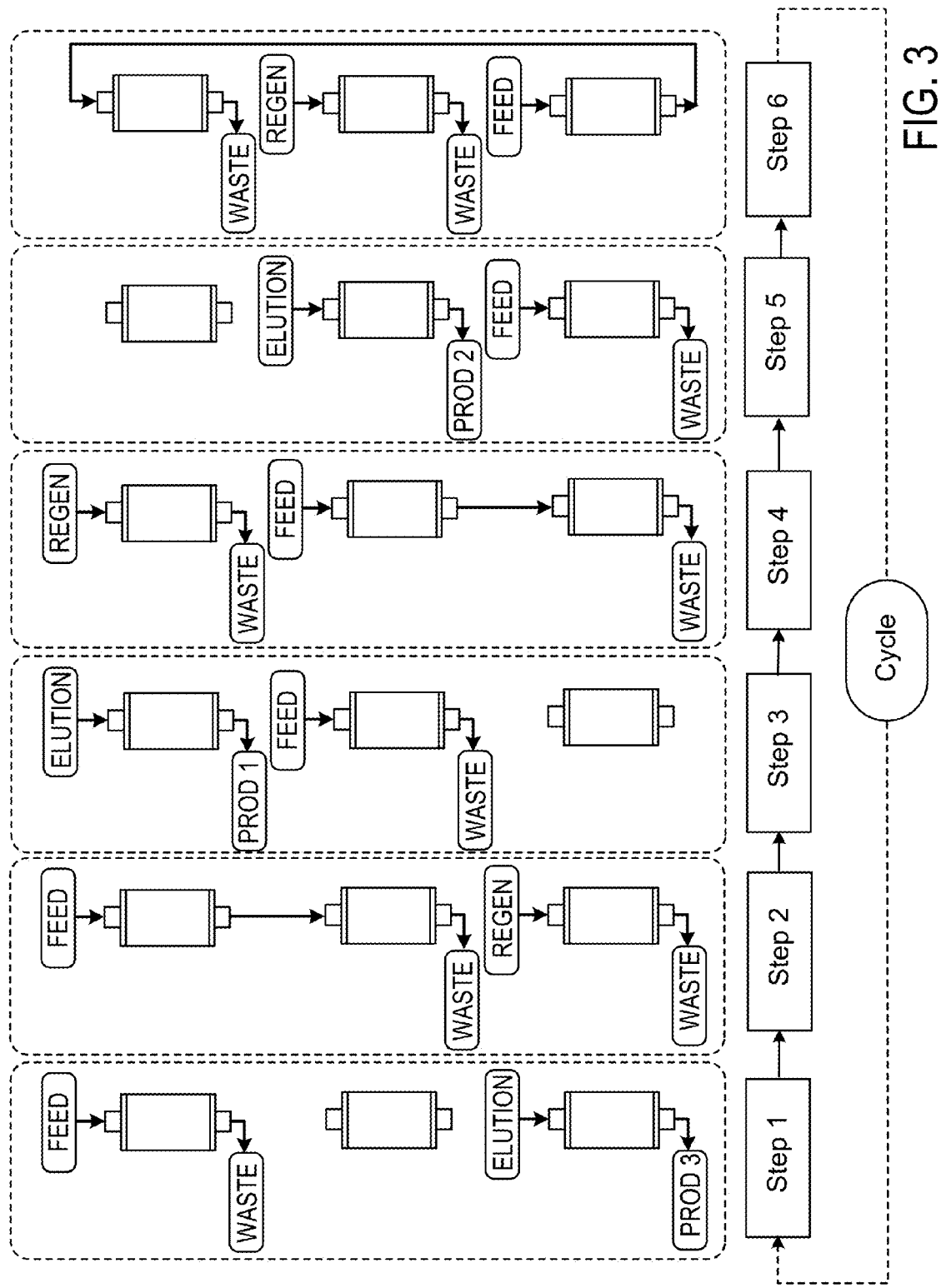
FIG. 3 is a diagram of a PCC system cycle containing three chromatography columns. At the beginning of a cycle, the feed solution is loaded onto column 1, and the flow through goes to waste until product breakthrough occurs (step 1). At this point, the flow through from column 1 is directed to column 2 to capture the unbound recombinant therapeutic protein from column 1 (step 2). Once column 1 is fully loaded, the feed is now directed loaded onto column 2, while column 1 is washed, eluted, regenerated, and re-equilibrated for the next cycle (steps 3 and 4). Column 2 now goes through steps 3-5, which are identical to steps 1-3 for column 1. Finally, column 3 goes through steps 5-6, the same as columns 1 and 2. Once all three columns have completed these steps, the cycle restarts with column 1.

The first and/or second MCCS can be a periodic counter current chromatography system (PCCS). A PCCS can, e.g., include two or more chromatography columns (e.g., three columns or four columns) that are switched in order to allow for the continuous elution of recombinant therapeutic protein from the two or more chromatography columns. A PCCS can include two or more chromatography columns, two or more chromatographic membranes, or at least one chromatographic column and at least one chromatographic membrane. A column operation generally consists of the load, wash, eluate, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography. An example of the three column-switching technique used in a PCCS containing three columns is shown in FIG. 3. A cycle is defined as three complete column operations resulting in an elution pool from each of the three columns used in the column-switching technique. Once all the steps in the cycle are completed, the cycle is re-started. As a result of the continuous cycling and elutation, fluid entering a PCCS is processed continuously, and the eluate containing recombinant therapeutic protein is continuously produced.

To advance from one step to another in a PCCS cycle, such as the exemplary cycle shown in FIG. 3, a column-switching strategy is employed. The column switching method employs two automated switching operations per column in the three-columns in the exemplary PCCS system shown in FIG. 3, the first of which is related to the initial product breakthrough, while the second coincides with column saturation. The determination of when the column switching operations should take place is determined by monitoring the recombinant therapeutic protein concentration (e.g., monitoring performed by UV monitoring) in the eluate from each chromatography column present in a PCCS. For example, column switching can be determined by any PAT tool capable of in-line measurement of product concentration with feedback control. The PAT tool is capable of real-time in-line measurement of product concentration with feedback control.

Figure 4:
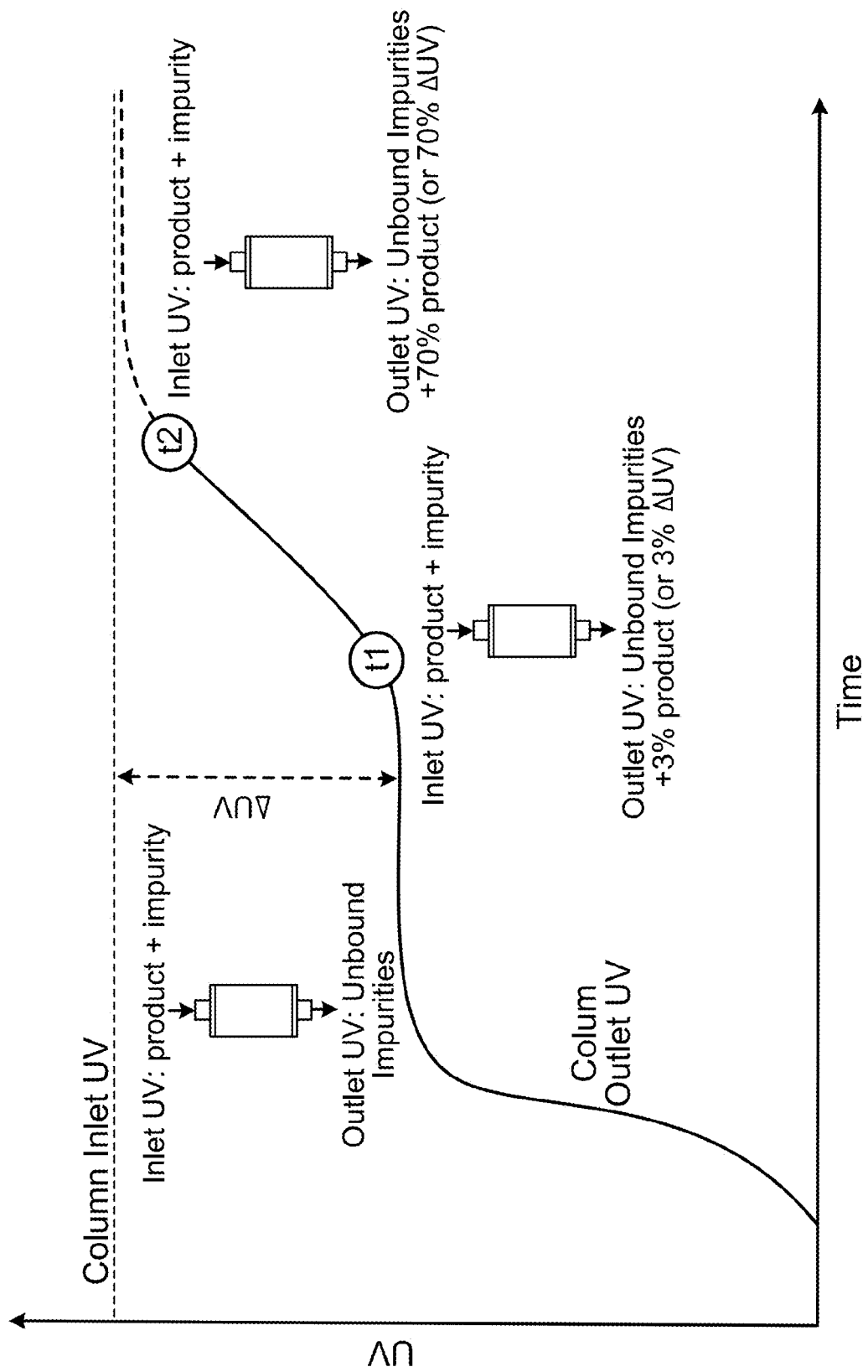
FIG. 4 is a schematic diagram demonstrating the principle of column switching based on ΔUV. T1 designates the time when the ΔUV has reached a pre-determined threshold level. Once this threshold level is reached, the flow through from column 1 is directed onto column 2 rather than to the waste. T2 designates the time when the column has been saturated with product. The ΔUV value for both T1 and T2 are process specific.

FIG. 4 depicts an example of column switching in an exemplary PCCS based on the UV absorbance difference (ΔUV) between the feed inlet and column outlet. For example, during column loading (Step 1; FIG. 3), the PCC control system determines the impurity baseline level when the absorbance stabilizes. As the product breaks through (Step 2; FIG. 3), there is an increase in the outlet UV signal above the impurity baseline. At the point when ΔUV has reached a pre-determined threshold (e.g., 3% breakthrough of the product), the flow-through from column 1 is directed onto column 2 instead of to the waste (t1; FIG. 4). When column 1 is nearly saturated with product and the ΔUV has reached a pre-determined value (t2; FIG. 4), the feed is switched to column 2. The column-switching strategy used in PCCSs allows for the uniform loading of the columns irrespective of the feed product concentration and the capacity. Similar switches of the columns based on the level of recombinant protein detected in the eluate from each column can be designed. As in known in the art, column switches can also be designed based on time or the amount of fluid (e.g., buffer) passed through the one or more chromatography column(s) and/or chromatographic membranes in the first or second MCCS.

In PCCSs, the residence time (RT) of the recombinant therapeutic protein on the each chromatography column and/or chromatographic membrane present in the PCCS can be decreased without increasing the column/membrane size because the breakthrough from the first column/membrane can be captured on another column/membrane in the PCCS. A continuous process system can be designed to process liquid culture medium at any perfusion rate (D) by varying the column/membrane volume (V) and RT using the equation of: V=D*RT.

The one or more unit operations that can be performed by the at least two MCCSs (e.g., the first and/or second MCCSs) used in the presently described processes include, for example, capturing the recombinant therapeutic protein, inactivating viruses present in a fluid containing the recombinant therapeutic protein, purifying the recombinant therapeutic protein, polishing the recombinant therapeutic protein, holding a fluid containing the recombinant therapeutic protein (e.g., using any of the exemplary break tank(s) described herein), filtering or removing particulate material and/or cells from a fluid containing the recombinant therapeutic protein, and adjusting the ionic concentration and/or pH of a fluid containing the recombinant therapeutic protein.

The unit operation of capturing can be performed using one or more MCCSs (e.g., a first and/or second MCCS) that includes at least one chromatography column and/or chromatography resin, e.g., that utilizes a capture mechanism. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Capturing can also be performed using a resin that can be used to perform cation exchange or anion exchange chromatography, or molecular sieve chromatography. Non-limiting resins that can be used to capture a recombinant therapeutic protein are described herein. Additional examples of resins that can be used to capture a recombinant therapeutic protein are known in the art.

The unit operation of inactivating viruses present in a fluid containing the recombinant therapeutic protein can be performed using one or more MCCSs (e.g., a first and/or second MCCS) that include(s), e.g., a chromatography column, a chromatography membrane, or a holding tank that is capable of incubating a fluid containing the recombinant therapeutic protein at a pH of between about 3.0 to 5.0 (e.g., between about 3.5 to about 4.5, between about 3.5 to about 4.25, between about 3.5 to about 4.0, between about 3.5 to about 3.8, or about 3.75) for a period of at least 30 minutes (e.g., a period of between about 30 minutes to 1.5 hours, a period of between about 30 minutes to 1.25 hours, a period of between about 0.75 hours to 1.25 hours, or a period of about 1 hour).

The unit operation of purifying a recombinant protein can be performed using one or more MCCSs (e.g., a first and/or second MCCS) that include(s), e.g., a chromatography column or chromatographic membrane that contains a resin, e.g., that utilizes a capture system. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Purifying can also be performed using a resin that can be used to perform cation exchange or anion exchange chromatography, or molecular sieve chromatography. Non-limiting resins that can be used to purify a recombinant therapeutic protein are described herein. Additional examples of resins that can be used to purify a recombinant therapeutic protein are known in the art.

The unit operation of polishing a recombinant protein can be performed using one or more MCCSs (e.g., a first and/or second MCCS) that include(s), e.g., a chromatography column or chromatographic membrane that contains a resin, e.g., that can be used to perform cation exchange, anion exchange, or molecular sieve chromatography. Non-limiting resins that can be used to polish a recombinant therapeutic protein are described herein. Additional examples of resins that can be used to polish a recombinant therapeutic protein are known in the art.

The unit operation of holding a fluid containing the recombinant therapeutic protein can be performed using an MCCS (e.g., a first and/or second MCCS) that includes at least one reservoir (e.g., a break tank) or a maximum of 1, 2, 3, 4, or 5 reservoir(s) (e.g., break tank(s)) in the first and second MCCS combined. For example, the reservoir(s) (e.g., break tank(s)) that can be used to achieve this unit operation can each have a volume of between about 1 mL to about 1 L (e.g., between about 1 mL to about 800 mL, between about 1 mL to about 600 mL, between about 1 mL to about 500 mL, between about 1 mL to about 400 mL, between about 1 mL to about 350 mL, between about 1 mL to about 300 mL, between about 10 mL and about 250 mL, between about 10 mL and about 200 mL, between about 10 mL and about 150 mL, and between about 10 mL to about 100 mL). The reservoir(s) (e.g., break tank(s)) used in the processes described herein can have a capacity that is, e.g., between 1 mL and about 300 mL, inclusive, e.g., between 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL, inclusive. Any of the reservoir(s) (e.g., break tank(s)) used (in any of the processes described herein) to hold fluid before it enters into the first MCCS can have a capacity that is, e.g., between 1 mL and about 100%, inclusive, between about 1 mL and about 90%, about 80%, about 70%, about 60%, about 50%, about 40%, about 30%, about 20%, about 10%, or about 5%, inclusive, of the loading volume of the first column of the first MCCS. Any of the reservoir(s) (e.g., break tanks(s)) used to hold a fluid before it enters the second MCCS (and after the fluid leaves the first MCCS) can have a capacity that is, e.g., between 1 mL and about 100%, inclusive, e.g., between about 1 mL and about 90%, about 80%, about 70%, about 60%, about 50%, about 40%, about 30%, about 20%, about 10%, or about 5%, inclusive, of the loading volume of the first column of the second MCCS.

The reservoir(s) (e.g., break tank(s)) can each hold the fluid containing the recombinant therapeutic protein for at least 10 minutes (e.g., at least 20 minutes, at least 30 minutes, at least 1 hour, at least 2 hours, at least 4 hours, or at least 6 hours). In other examples, the reservoir(s) (e.g., break tank(s)) only holds a therapeutic protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive. The reservoir (s) (e.g., break tank(s)) can be used to both hold and refrigerate (e.g., at a temperature of less than 25° C., less than 15° C., or less than 10° C.) the fluid containing the recombinant therapeutic protein. The reservoir can have any shape, including a circular cylinder, an oval cylinder, or an approximately rectangular sealed and nonpermeable bag.

The unit operations of filtering a fluid containing the recombinant therapeutic protein can be performed using an MCCS (e.g., the first and/or second MCCS) that includes, e.g., a filter, or a chromatography column or chromatographic membrane that contains a molecule sieve resin. As is known in the art, a wide variety of submicron filters (e.g., a filter with a pore size of less than 1 µm, less than 0.5 µm, less than 0.3 µm, about 0.2 µm, less than 0.2 µm, less than 100 nm, less than 80 nm, less than 60 nm, less than 40 nm, less than 20 nm, or less than 10 nm) are available in the art that are capable of removing any precipated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 µm or less than 0.2 µm are known to effectively remove bacteria from the fluid containing the recombinant therapeutic protein. As is known in the art, a chromatography column or a chromatographic membrane containing a molecular sieve resin can also be used in an MCCS (e.g., the first and/or second MCCS) to perform the unit operation of filtering a fluid containing a recombinant therapeutic protein.

The unit operations of adjusting the ionic concentration and/or pH of a fluid containing the recombinant therapeutic protein can be performed using a MCCS (e.g., the first and/or second MCCS) that includes and utilizes a buffer adjustment reservoir (e.g., an in-line buffer adjustment reservoir) that adds a new buffer solution into a fluid that contains the recombinant therapeutic protein (e.g., between columns within a single MCCS, or after the last column in a penultimate MCCS (e.g., the first MCCS) and before the fluid containing the recombinant therapeutic protein is fed into the first column of the next MCCS (e.g., the second MCCS). As can be appreciated in the art, the in-line buffer adjustment reservoir can be any size (e.g., greater than 100 mL) and can contain any buffered solution (e.g., a bufferered solution that has one or more of: an increased or decreased pH as compared to the fluid containing the recombinant therapeutic protein, a an increased or decreased ionic (e.g., salt) concentration compared to the fluid containing the recombinant therapeutic protein, and/or an increased or decreased concentration of an agent that competes with the recombinant therapeutic protein for binding to resin present in at least one chromatographic column or at least one chromatographic membrane in an MCCS (e.g., the first or the second MCCS)).

The first and/or second MCCS can perform two or more unit operations. For example, the first and/or second MCCS can each perform at least the following unit operations: capturing the recombinant therapeutic protein and inactivating viruses present in the fluid containing the recombinant therapeutic protein; capturing the recombinant therapeutic protein, inactivating viruses present in the fluid containing the recombinant therapeutic protein, and adjusting the ionic concentration and/or pH of a liquid containing the recombinanant therapeutic protein; purifying the recombinant therapeutic protein and polishing the recombinant therapeutic protein; purifying the recombinant therapeutic protein, polishing the recombinant therapeutic protein, and filtering a fluid containing the recombinant therapeutic protein or removing precipitates and/or particular matter from a fluid containing the recombinant therapeutic protein; and purifying the recombinant therapeutic protein, polishing the recombinant therapeutic protein, filtering a fluid containing the recombinant therapeutic protein or removing precipitates and/or particular matter from a fluid containing the recombinant therapeutic protein, and adjusting the ionic concentration and/or pH of a liquid containing the recombinant therapeutic protein.

Capturing the Recombinant Therapeutic Protein

The present processes include a step of capturing the recombinant therapeutic protein using a first MCCS. As can be appreciated in the art, the liquid culture medium containing the recombinant therapeutic protein can be continuously fed onto the first MCCS using a variety of different means. For example, the liquid culture medium can be actively pumped into the first MCCS or the liquid culture medium can be fed into the first MCCS using gravitational force. The liquid culture medium can be stored in a reservoir (e.g., a holding tank) before it is fed into the first MCCS or the liquid culture medium can be actively pumped from a bioreactor containing a culture of cells (e.g., mammalian cells that secrete the recombinant therapeutic protein into the culture medium) into the first MCCS.

The liquid culture medium can be fed (loaded) into the first MCCS at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The liquid culture medium containing the recombinant therapeutic protein can be derived from any of the exemplary sources described herein or known in the art.

Some examples further include the optional step of filtering the liquid culture medium before it is fed onto the first MCCS. Any of the exemplary means of filtering a liquid culture medium or a fluid containing the recombinant therapeutic protein described herein, or any filtration means known in the art, can be used to filter the liquid culture medium containing the recombinant therapeutic protein before it is fed into the first MCCS.

In the methods described herein, the capturing of the recombinant therapeutic protein from the liquid culture medium is performed using a first MCCS. As can be appreciated in the art, in order to achieve the capture of the recombinant therapeutic protein, at least one chromatographic column or at least one chromatographic membrane in the first MCCS must contain a resin that utilizes a capturing mechanism (e.g., any of the exemplary capturing mechanisms described herein), or contains a resin capable of performing cation exchange, anion exchange, or molecule sieve chromatography. For example, if the recombinant therapeutic protein is an antibody or an antibody fragment, the capturing system can be a protein A-binding capturing mechanism or an antigen-binding capturing mechanism (where the capturing antigen is specifically recognized by the recombinant therapeutic antibody or antibody fragment). If the recombinant therapeutic protein is an enzyme, the capturing mechanism can use an antibody or antibody fragment that specifically binds to the enzyme to capture the recombinant therapeutic enzyme, a substrate of the enzyme to capture the recombinant therapeutic enzyme, a cofactor of the enzyme to capture the recombinant therapeutic enzyme, or, if the recombinant therapeutic enzyme contains a tag, a protein, metal chelate, or antibody (or antibody fragment) that specifically binds to the tag present in the recombinant therapeutic enzyme. Non-limiting resins that can be used to capture a recombinant therapeutic protein are described herein and additional resins that can be used to capture a recombinant therapeutic protein are known in the art. One non-limiting example of resin that utilizes a protein A-binding capture mechanism is MabSelect SuRe resin (GE Healthcare, Piscataway, N.J.).

Exemplary non-limiting sizes and shapes of the chromatography column(s) or chromatographic membrane(s) present in the first MCCS that can be used to capture the recombinant therapeutic protein are described herein. The liquid culture medium fed (loaded) into the first MCCS can contain, e.g., between about 0.05 mg/mL to about 100 mg/mL recombinant therapeutic protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant therapeutic protein). The mean time required for the recombinant therapeutic protein to bind to the resin used to perform the unit operation of capturing can be, e.g., between about 5 seconds to about 10 minutes (e.g., between about 10 seconds to about 8 minutes, between about 10 seconds to about 7 minutes, between about 10 seconds to about 6 minutes, between about 10 seconds to about 5 minutes, between about 30 seconds to about 5 minutes, between about 1 minute to about 5 minutes, between about 10 seconds to about 4 minutes, between about 30 seconds to about 4 minutes, or between about 1 minute to about 4 minutes).

As can be appreciated in the art, in order to capture the recombinant therapeutic protein using the chromatography column(s) or chromatographic membrane(s) present in the first MCCS, one must perform the sequential chromatographic steps of loading, washing, eluting, and regenerating the chromatography column(s) or chromatography membrane(s) present in the first MCCS. Any of the exemplary flow rates, buffer volumes, and/or lengths of time allotted for each sequential chromatographic step described herein can be used in the one or more of these different sequential chromatographic steps (e.g., one or more of the sequential chromatographic steps of loading, washing, eluting, and regenerating the chromatography column(s) or chromatography membrane(s) present in the first MCCS that are used for capturing the recombinant therapeutic protein). Non-limiting flow rates, buffer volumes, and/or lengths of time allotted for each sequential chromatographic step that can be used for capturing chromatographic column(s) and/or chromatographic membrane(s) in the first MCCS (e.g., a first PCC system) are provided below. In addition, exemplary buffers elution buffers that can be used in the first MCCS are described below.

The first MCCS containing at least one chromatographic column and/or chromatographic membrane containing a resin that can perform the unit operation of capturing (e.g., any of exemplary resins that can be used for capturing described herein) can be loaded with the liquid culture medium containing a recombinant therapeutic protein using any of loading flow rates (fed rates) described above. In some examples, a single chromatographic column or single chromatographic membrane containing a resin that is capable of performing the unit operation of capturing is loaded in, e.g., between about 10 minutes to about 90 minutes (e.g., between about 15 minutes and about 90 minutes, between about 20 minutes and 80 minutes, between about 30 minutes and 80 minutes, between about 40 minutes and about 80 minutes, between about 50 minutes and about 80 minutes, and between about 60 minutes and 80 minutes). In some examples, wherein the first MCCS includes at least two chromatographic columns that contain a resin that is capable of performing the unit operation of capturing in series, the time required to load two of the chromatographic columns in series is, e.g., between about 50 minutes to about 180 minutes (e.g., between about 60 minutes and about 180 minutes, between about 70 minutes and about 180 minutes, between about 80 minutes and about 180 minutes, between about 90 minutes and about 180 minutes, between about 100 minutes and about 180 minutes, between about 110 minutes and about 180 minutes, between about 125 minutes and about 145 minutes).

Following the loading of the recombinant therapeutic protein onto the at least one chromatographic column or chromatographic membrane in the first MCCS that contains a resin that is capable of performing the unit operation of capturing, the at least one chromatographic column or chromatographic membrane is washed with at least one washing buffer. As can be appreciated in the art, the at least one (e.g., two, three, or four) washing buffer is meant to elute all proteins that are not the recombinant therapeutic protein from the at least one chromatography column or chromatographic membrane, while not disturbing the interaction of the recombinant therapeutic protein with the resin.

The wash buffer can be passed through the at least one chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, or between about 30 minutes to about 1 hour).

Following the washing of the at least one chromatographic column or chromatographic membrane in the first MCCS that contains a resin that is capable of performing the unit operation of capturing, the recombinant therapeutic protein is eluted from the at least one chromatographic column or chromatographic membrane by passing an elution buffer through the at least one chromatographic column or chromatographic membrane in the first MCCS that contains a resin that is capable of performing the unit operation of capturing. The elution buffer can be passed through the at least one chromatography column or chromatographic membrane that contains a resin that is capable of performing the unit operation of capturing at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 1.0 mL/minute and about 15.0 mL/minute). The volume of elution buffer used to elute the recombinant therapeutic protein from each of the at least one chromatographic column or chromatographic membrane containing a resin that is capable of performing the unit operation of purifying can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes). Non-limiting examples of elution buffers that can be used in these methods will depend on the capture mechanism and/or the therapeutic protein. For example, an elution buffer can contain a different concentration of salt (e.g., increased salt concentration), a different pH (e.g., an increased or decreased salt concentration), or a molecule that will compete with the recombinant therapeutic protein for binding to the resin that is capable of performing the unit operation of capturing. Examples of such elution buffers for each exemplary capture mechanism described herein are well known in the art.

Following the elution of the recombinant therapeutic protein from the at least one chromatographic column or chromatographic membrane in the first MCCS that contains a resin that is capable of performing the unit operation of capturing, and before the next volume of liquid culture medium can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane that contains a resin that is capable of performing the unit operation of capturing at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute). The volume of regeneration buffer used to equilibrate the at least one chromatography column or chromatographic membrane that contains a resin that is capable of performing the unit operation of capturing can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 2×CV to about 5×CV, about 4×CV to about 11×CV, about 5×CV to about 11×CV, or about 5×CV to about 10×CV).

In some of the processes described herein, the first MCCS includes a reservoir that holds a fluid containing the recombinant therapeutic protein at low pH (e.g., a pH below 4.6, below 4.4, below 4.2, below 4.0, below 3.8, below 3.6, below 3.4, below 3.2, or below 3.0) for, e.g., about 1 minute to 1.5 hours (e.g., about 1 hour), and inactivates the viruses present in a fluid containing the recombinant therapeutic protein. An example of a reservoir that can be used to perform the unit operation of inactivating viruses is a stir flask (e.g., 500-mL stir flask, e.g., a 500-mL stir flask with a programmed stir plate) that is capable of holding a fluid containing a recombinant therapeutic protein for, e.g., about 1 minute to 1.5 hours, before the fluid containing the recombinant therapeutic protein is fed into the second MCCS. The reservoir that is used to perform the unit operation of inactivation of viruses can be a 500-mL stir flask with a programmed stir plate (e.g., a stir plate programmed to mix (e.g., periodically mix) the fluid within the reservoir, e.g., every 4 hours). Another example of a reservoir that can be used to perform the unit operation of inactivation of viruses is a plastic bag (e.g., 500-mL plastic bag) that is capable of holding a fluid containing a recombinant therapeutic protein for, e.g., about 1 minute to 1.5 hours, before the fluid containing the recombinant therapeutic protein is fed into the second MCCS. In some examples, the fluid containing the recombinant therapeutic protein can already have a low pH (e.g., a pH below 4.6, below 4.4, below 4.2, below 4.0, below 3.8, below 3.6, below 3.4, below 3.2, or below 3.0) when it is fed into the reservoir that is used to perform the unit operation of viral inactivation. As can be appreciated by those skilled in the art, a variety of other means can be used to perform the unit operation of inactivating viruses. For example, UV irradiation of a fluid containing recombinant therapeutic protein can also be used to perform the unit operation of inactivating viruses. Non-limiting examples of reservoirs that can be used to perform the unit operation of inactivation of viruses present in a fluid containing the recombinant therapeutic protein are described herein.

The first MCCS can include a PCCS containing four chromatography columns, where at least three of the four chromatography columns perform the unit operation of capturing the recombinant therapeutic protein from the liquid culture medium (e.g., using a first MCCS that includes any of the at least one chromatography columns that contain a resin that is capable of performing the unit operation of capturing (e.g., any of those described herein)). In these examples, the fourth-column of the PCC can perform the unit operation of inactivating viruses in a fluid that contains the recombinant therapeutic protein (e.g., any of the exemplary columns described herein that can be used to achieve viral inactivation of a fluid containing the recombinant therapeutic protein).

A fluid containing the recombinant therapeutic protein is continuously eluted from the first MCCS (e.g., the first PCC system), and is continuously fed into the second MCCS. The percent of the recombinant therapeutic protein recovered in the eluate of the first MCCS (e.g., the first PCC system) can be, e.g., at least 70%, at least 72%, at least 74%, at least 76%, at least 78%, at least 80%, at least 82%, at least 84%, at least 86%, at least 88%, at least 90%, at least 92%, at least 94%, at least 96%, or at least 98%). The eluate from the first MCCS (e.g., the first PCC system) can be fed into the second MCCS (e.g., second PCC system) using a variety of means known in the art (e.g., tubing). The eluate of the first MCCS (e.g., first PCC system) can be fed into the second MCCS (e.g., second PCC system) at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, between about 15 mL/minute to about 25 mL/minute, or between about 1.0 mL/minute and about 15.0 mL/minute).

Some processes described herein can further include a step of adjusting the ionic concentration and/or pH of the eluate from the first MCCS (e.g., first PCC system) before it is fed into the second MCCS (e.g., second PCC system). As described herein, the ionic concentration and/or pH of the eluate from the first MCCS (e.g., first PCC system) can be adjusted (before it is fed into the second MCCS) by adding a buffer to the eluate (e.g., through the use of an in-line buffer adjustment reservoir). The buffer can be added to the eluate from the first MCCS at a flow rate of, e.g., between about 0.1 mL/minute to about 15 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, or between about 0.5 mL/minute to about 5 mL/minute).

The processes described herein can further include a step of holding or storing (and optionally also refridgerating) the eluate from the first MCCS prior to feeding the eluate from the first MCCS into the second MCCS. As described herein, this holding or storing step can be performed using any of the reservoirs (e.g., back-up tanks) described herein.

The processes described herein can also include a step of filtering the eluate from the first MCCS before the eluate is fed into the second MCCS. Any of the exemplary filters or methods for filtration described herein can be used to filter the eluate from the first MCCS before the eluate is fed into the second MCCS.

Polishing and Purifying the Recombinant Therapeutic Protein

The processes described herein include a step of purifying and polishing the recombinant therapeutic protein using a second MCCS, where the eluate from the MCC2 is a therapeutic protein drug substance. The second MCCS can include at least one (e.g., two, three, or four) chromatography column or chromatographic membrane that can be used to perform the unit operation of purifying a recombinant therapeutic protein, and at least one (e.g., two, three, or four) chromatography column or chromatographic membrane that can be used to perform the unit operation of polishing the recombinant therapeutic protein.

The at least one chromatography column or chromatographic membrane that can be used to perform the unit operation of purifying the recombinant therapeutic protein can contain a resin that utilizes a capture mechanism (e.g., any of the capture mechanisms described herein or known in the art), or a resin that can be used to perform anion exchange, cation exchange, or molecular sieve chromatography. The at least one chromatography column or chromatographic membrane that can be used to perform the unit of operation of polishing the recombinant therapeutic protein can contain a resin can be used to perform anion exchange, cation exchange, or molecular sieve chromatography (e.g., any of the exemplary resins for performing anion exchange, cation exchange, or molecular sieve chromatography described herein or known in the art).

The size, shape, and volume of the at least one chromatography column or chromatography membrane that can be used to perform the unit of operation of purifying the recombinant therapeutic protein, and/or the size and shape of the at least one chromatographic membrane that can be used to perform the unit of operation of polishing the recombinant membrane can any of combination of the exemplary sizes, shapes, and volumes of chromatography columns or chromatographic membranes described herein. As can be appreciated by one skilled in the art, the step of purifying or polishing a recombinant therapeutic protein can, e.g., include the steps of loading, washing, eluting, and equilibrating the at least one chromatography column or chromatographic membrane used to perform the unit of operation of purifying or polishing the recombinant therapeutic protein. Typically, the elution buffer coming out of a chromatography column or chromatographic membrane used to perform the unit operation of purifying contains the recombinant therapeutic protein. Typically, the loading and/or wash buffer coming out of a chromatography column or chromatographic membrane used to perform the unit operation of polishing contains the recombinant therapeutic protein.

For example, the size of the at least one chromatography column or chromatographic membrane that can be used to perform unit operation of purifying the recombinant therapeutic protein can have a volume of, e.g., between about 2.0 mL to about 200 mL (e.g., between about 2.0 mL to about 180 mL, between about 2.0 mL to about 160 mL, between about 2.0 mL to about 140 mL, between about 2.0 mL to about 120 mL, between about 2.0 mL to about 100 mL, between about 2.0 mL to about 80 mL, between about 2.0 mL to about 60 mL, between about 2.0 mL to about 40 mL, between about 5.0 mL to about 40 mL, between about 2.0 mL to about 30 mL, between about 5.0 mL to about 30 mL, or between about 2.0 mL to about 25 mL). The flow rate of the fluid containing the recombinant therapeutic protein as it is loaded onto the at least one chromatography column or at least one chromatographic that can be used to perform the unit operation of purifying the recombinant therapeutic protein can be, e.g., between about 0.1 mL/minute to about 25 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, between about 0.1 mL/minute to about 3 mL/minute, between about 0.1 mL/minute to about 2 mL/minute, or about 0.2 mL/minute to about 4 mL/minute). The concentration of the recombinant therapeutic protein in the fluid loaded onto the at least one chromatography column or chromatographic membrane that can be used to perform the unit operation of purifying the recombinant therapeutic protein can be, e.g., between about 0.05 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant therapeutic protein). The resin in the at least one chromatography column or chromatographic membrane used to perform unit operation of purifying can be a resin that can be used to perform anion exchange or cation exchange chromatography. The resin in the at least one chromatography column or chromatographic membrane that is used to perform the unit operation of purifying can be a cationic exchange resin (e.g., Capto-S resin, GE Healthcare Life Sciences, Piscataway, N.J.).

Following the loading of the recombinant therapeutic protein onto the at least one chromatographic column or chromatographic membrane in the second MCCS that can be used to perform the unit operation of purifying the recombinant therapeutic protein, the at least one chromatographic column or chromatographic membrane is washed with at least one washing buffer. As can be appreciated in the art, the at least one (e.g., two, three, or four) washing buffer is meant to elute all proteins that are not the recombinant therapeutic protein from the at least one chromatography column or chromatographic membrane, while not disturbing the interaction of the recombinant therapeutic protein with the resin or otherwise eluting the recombinant therapeutic protein.

The wash buffer can be passed through the at least one chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, between about 30 minutes to about 1 hour, between about 2 minutes and 10 minutes, between about 2 minutes and 15 minutes, or between about 2 minutes and 30 minutes).

Following the washing of the at least one chromatographic column or chromatographic membrane in the second MCCS that can be used to perform the unit operation of purifying the recombinant therapeutic protein, the recombinant therapeutic protein is eluted from the at least one chromatographic column or chromatographic membrane by passing an elution buffer through the at least one chromatographic column or chromatographic membrane in the second MCCS that can be used to perform the unit operation of purifying the recombinant therapeutic protein. The elution buffer can be passed through the at least one chromatography column or chromatographic membrane that can be used to perform the unit operation of purifying the recombinant therapeutic protein at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 1.0 mL/minute and about 15.0 mL/minute). The volume of elution buffer used to elute the recombinant therapeutic protein from each the at least one chromatographic column or chromatographic membrane that can be used to perform the unit operation of purifying the recombinant therapeutic protein can be, e.g., between about 1× column volume (CV) to about 25×CV (e.g., between about 1×CV to about 20×CV, between about 15×CV and about 25×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes, or between about 30 minutes and 1.0 hour). Non-limiting examples of elution buffers that can be used in these methods will depend on the resin and/or the therapeutic protein. For example, an elution buffer can contain a different concentration of salt (e.g., increased salt concentration), a different pH (e.g., an increased or decreased salt concentration), or a molecule that will compete with the recombinant therapeutic protein for binding to the resin. Examples of such elution buffers for each of the exemplary capture mechanisms described herein are well known in the art.

Following the elution of the recombinant therapeutic protein from the at least one chromatographic column or chromatographic membrane in the second MCCS that can be used to perform the unit operation of purifying the recombinant therapeutic protein, and before the next volume of fluid containing a recombinant therapeutic protein can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane that can be used to perform the unit operation of purifying the recombinant therapeutic protein at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute). The volume of regeneration buffer used to equilibrate the at least one chromatography column or chromatographic membrane that contains a resin that can be used to perform the unit operation of purifying the recombinant therapeutic protein can be, e.g., between about 1× column volume (CV) to about 15×CV (e.g., between about 1×CV to about 14×CV, between about 1×CV to about 13×CV, between about 1×CV to about 12×CV, between about 1×CV to about 11×CV, between about 2×CV to about 11×CV, between about 3×CV to about 11×CV, between about 2×CV to about 5×CV, between about 2.5×CV to about 7.5×CV, between about 4×CV to about 11×CV, between about 5×CV to about 11×CV, or between about 5×CV to about 10×CV). The concentration of recombinant therapeutic protein in the eluate of the at least one chromatography column or chromatographic membrane that can be used to perform the unit operation of purifying the recombinant therapeutic protein can be, e.g., between about 0.05 mg/mL to about 100 mg/mL recombinant therapeutic protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant therapeutic protein).

The at least one chromatography column or chromatographic membrane that can be used to perform the unit operation of polishing the recombinant therapeutic protein can contain a resin that can be used to perform cation exchange, anion exchange, or molecular sieve chromatography. As can be appreciated in the art, polishing a recombinant therapeutic protein using the at least one chromatography column or chromatography membrane that can be used to perform the unit operation of polishing the recombinant therapeutic protein in the second MCCS can include, e.g., the steps of loading, chasing, and regenerating the at least one chromatography column or chromatographic membrane that can be used to perform the unit operation of polishing the recombinant therapeutic protein. For example, when the steps of loading, chasing, and regenerating are used to perform the polishing, the recombinant therapeutic protein does not bind the resin in the at least one chromatography column or chromatography membrane in the second MCCS that is used to perform the unit operation of polishing the recombinant therapeutic protein, and the recombinant therapeutic protein is eluted from the at least one chromatography column or chromatographic membrane in the loading and chasing steps, and the regenerating step is used to remove any impurities from the at least one chromatography column or chromatographic membrane before additional fluid containing the recombinant therapeutic protein can be loaded onto the at least one chromatography column or chromatographic membrane. Exemplary flow rates and buffer volumes to be used in each of the loading, chasing, and regenerating steps are described below.

The size, shape, and volume of the at least one chromatography column or chromatography membrane that can be used to perform the unit operation of polishing the recombinant therapeutic protein, and/or the size and shape of the at least one chromatographic membrane that can be used to perform the unit operation of polishing the recombinant therapeutic protein can any of combination of the exemplary sizes, shapes, and volumes of chromatography columns or chromatographic membranes described herein. For example, the size of the at least one chromatography column or chromatographic membrane that can be used to perform the unit operation of polishing the recombinant therapeutic protein can have a volume of, e.g., between about 0.5 mL to about 200 mL (e.g., between about 0.5 mL to about 180 mL, between about 0.5 mL to about 160 mL, between about 0.5 mL to about 140 mL, between about 0.5 mL to about 120 mL, between about 0.5 mL to about 100 mL, between about 0.5 mL to about 80 mL, between about 0.5 mL to about 60 mL, between about 0.5 mL to about 40 mL, between about 5.0 mL to about 40 mL, between about 0.5 mL to about 30 mL, between about 5.0 mL to about 30 mL, between about 0.5 mL to about 25 mL, between about 0.2 mL to about 10 mL, or between about 0.2 mL to about 5 mL). The flow rate of the fluid containing the recombinant therapeutic protein as it is loaded onto the at least one chromatography column or chromatographic membrane that can be used to perform the unit operation of polishing the recombinant therapeutic protein can be, e.g., between about 0.1 mL/minute to about 25 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, between about 0.1 mL/minute to about 3 mL/minute, between about 2 mL/minute and about 6 mL/minute, between about 0.1 mL/minute to about 2 mL/minute, or about 0.2 mL/minute to about 4 mL/minute). The total volume of fluid containing a recombinant therapeutic protein loaded onto the at least one chromatography column or chromatographic membrane that can be used to perform the unit operation of polishing the recombinant therapeutic protein can be, e.g., between about 1.0 mL to about 250 mL (e.g., between about 1.0 mL to about 225 mL, between about 1.0 mL to about 200 mL, between about 1.0 mL to about 175 mL, between about 1.0 mL to about 150 mL, between about 100 mL to about 125 mL, between about 100 mL to about 150 mL, between about 1.0 mL to about 150 mL, between about 1.0 mL to about 125 mL, between about 1.0 mL to about 100 mL, between about 1.0 mL to about 75 mL, between about 1.0 mL to about 50 mL, or between about 1.0 mL to about 25 mL). The resin in the at least one chromatography column or chromatographic membrane used to perform the polishing can be an anion exchange or cation exchange resin. The resin in the at least one chromatography column or chromatographic membrane that is used to perform the unit operation of polishing can be a cationic exchange resin (e.g., Sartobind® Q resin, Sartorius, Goettingen, Germany).

Following the loading step, the at least one chromatographic column or chromatographic membrane in the second MCCS that can be used to perform the unit operation of polishing the recombinant therapeutic protein, a chasing step is performed (e.g., a chase buffer is passed through the at least one chromatography membrane or chromatographic membrane to collect the recombinant therapeutic protein which does not substantially bind to the at least one chromatography column or chromatographic membrane). In these examples, the chase buffer can be passed through the at least one chromatography column or chromatographic membrane at a flow rate of between about 0.2 mL/minute to about 50 mL/minute (e.g., between about 1 mL/minute to about 40 mL/minute, between about 1 mL/minute to about 30 mL/minute, between about 5 mL/minute to about 45 mL/minute, between about 10 mL/minute to about 40 mL/minute, between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of chase buffer used can be, e.g., between about 1× column volume (CV) to about 100×CV (e.g., between about 1×CV to about 90×CV, between about 1×CV to about 80×CV, between about 1×CV to about 70×CV, between about 1×CV to about 60×CV, between about 1× to about 50×CV, between about 1×CV to about 40×CV, between about 1×CV to about 30×CV, between about 1×CV to about 20×CV, between about 1×CV to about 15×CV, between about 5×CV to about 20×CV, between about 5×CV to about 30×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV). The total time of the chasing can be, e.g., between about 1 minute to about 3 hours (e.g., between about 1 minute to about 2.5 hours, between about 1 minute to about 2.0 hours, between about 1 minutes to about 1.5 hours, between about 2 minutes to about 1.5 hours, between about 1 minutes to about 1.25 hours, between about 2 minutes to about 1.25 hours, between about 1 minute to about 5 minutes, between about 1 minute to about 10 minutes, between about 2 minutes to about 4 minutes, between about 30 minutes to about 1 hour, between about 2 minutes and 10 minutes, between about 2 minutes and 15 minutes, or between about 2 minutes and 30 minutes). The combined concentration of therapeutic recombinant protein present in the eluate coming through the column in the loading step and the chasing step can be, e.g., between about 0.1 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, between about 0.5 mg/mL to about 10 mg/mL, or between about 1 mg/mL and about 5 mg/mL recombinant therapeutic protein).

Following the chasing step and before the next volume fluid containing a recombinant therapeutic protein can be loaded onto the at least one chromatographic column or chromatographic membrane that can be used to perform the unit operation of polishing, the at least one chromatography column or chromatographic membrane must be regenerated using a regeneration buffer. The regeneration buffer can be passed through the at least one chromatography column or chromatographic membrane that can be used to perform the unit operation of polishing the recombinant therapeutic protein at a flow rate of, e.g., between about 0.2 mL/minute to about 50 mL/minute (e.g., between about 1 mL/minute to about 40 mL/minute, between about 1 mL/minute to about 30 mL/minute, between about 5 mL/minute to about 45 mL/minute, between about 10 mL/minute to about 40 mL/minute, between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of regeneration buffer used to regenerate the at least one chromatography column or chromatographic membrane that can be used to perform the unit operation of polishing can be, e.g., between about 1× column volume (CV) to about 500×CV (e.g., between about 1×CV to about 450×CV, between about 1×CV to about 400×CV, between about 1×CV to about 350×CV, between about 1×CV to about 300×CV, between about 1×CV to about 250×CV, between about 1×CV to about 200×CV, between about 1×CV to about 150×CV, between about 1×CV to about 100×CV, between about 1×CV to about 90×CV, between about 1×CV to about 80×CV, between about 1×CV to about 70×CV, between about 1×CV to about 60×CV, between about 1× to about 50×CV, between about 1×CV to about 40×CV, between about 1×CV to about 30×CV, between about 1×CV to about 20×CV, between about 1×CV to about 15×CV, between about 5×CV to about 20×CV, between about 5×CV to about 30×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV).

In other examples, the one or more chromatography column(s) and/or chromatographic membranes used to perform the unit operation of polishing contain a resin that selectively binds or retains the impurities present in a fluid containing the recombinant therapeutic protein, and instead of regenerating the one or more column(s) and/or membrane(s), the one or more column(s) and/or membrane(s) are replaced (e.g., replaced with a substantially similar column(s) and/or membrane(s)) once the binding capacity of the resin in the one or more column(s) and/or membrane(s) has been reached or is substantially close to being reached.

In some examples of these processes, the second MCCS includes a PCCS containing three chromatography columns and one chromatographic membrane, e.g., where the three chromatography columns in the PCCS perform the unit operation of purifying the recombinant therapeutic protein (e.g., using at least one chromatography column(s) that can be used to perform the unit of operation of purifying the protein) and the chromatographic membrane in the PCCS performs the unit operation of polishing the recombinant therapeutic protein. In these examples, the chromatographic membrane in the PCCS that can be used to perform the unit operation of polishing the recombinant therapeutic protein can be any of the exemplary chromatographic membranes described herein that can be used to perform the unit operation of polishing the recombinant therapeutic protein. Any of the column switching methods described herein can be used to determine when the first three chromatography columns and the chromatographic membrane in the PCCS in this example can be switched.

Some embodiments of this example can further include a step of adjusting the ionic concentration and/or pH of the eluate from the three chromatographic columns in the PCCS before the eluate is fed into the chromatographic membrane in the PCCS. As described herein, the ionic concentration and/or pH of the eluate from the three chromatography columns in PCCS can be adjusted (before it is fed into the chromatographic membrane in the PCCS in this example)) by adding a buffer to the eluate of the three chromatography columns in the PCCS (e.g., through the use of an in-line buffer adjustment reservoir). The buffer can be added to the eluate at a flow rate of, e.g., between about 0.1 mL/minute to about 15 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, or between about 0.5 mL/minute to about 5 mL/minute).

These examples can further include a step of holding or storing the eluate from the three chromatography columns in the PCCS in this example prior to feeding the eluate into the chromatographic membrane (chromatographic membrane that can be used to perform the unit operation of polishing the recombinant therapeutic protein). As described herein, this holding or storing step can be performed using any of the reservoirs (e.g., back-up tanks) described herein.

These examples can also include a step of filtering the eluate from the chromatographic membrane in the exemplary PCCS system (eluate of the chromatographic membrane that can be used to perform the unit operation of polishing the recombinant therapeutic protein). Any of the exemplary filters or methods for filtration described herein can be used to filter the eluate from the chromatographic membrane in this exemplary PCCS (eluate of the chromatographic membrane that can be used to perform the unit operation of polishing the recombinant therapeutic protein).

As can be appreciated by those in the art, the therapeutic protein drug substance can be periodically eluted from the second MCCS using any of the processes described herein. For example, any of the processes described herein can elute the therapeutic protein drug substance for a duration of, e.g., between about 30 seconds and about 5 hours (e.g., between about 1 minute and about 4 hours, between about 1 minute and about 3 hours, between about 1 minute and about 2 hours, between about 1 minute or about 1.5 hours, between about 1 minute and about 1 hour, between about 1 minute and about 30 minutes) at a frequency of, e.g., between about 1 minute and about 6 hours (e.g., between about 1 minute and about 5 hours, between about 1 minute and about 4 hours, between about 1 minute and about 3 hours, between about 1 minute and 2 hours, between about 1 minute and 1 hour, or between about 1 minute and 30 minutes), depending on, e.g., the chromatography column(s) and/or chromatographic membrane(s) used in the first and second MCCS.

Culturing Methods

Some of the processes described herein further include a step of culturing cells (e.g., recombinant mammalian cells) that secrete a recombinant therapeutic protein in a bioreactor (e.g., a perfusion or fed-batch bioreactor) that contains a liquid culture medium, wherein a volume of the liquid culture medium that is substantially free of cells (e.g., mammalian cells) is continuously or periodically removed from the perfusion bioreactor and fed into the first multi-column chromatography system (MCC1). The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about 1 L and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a fed-batch bioreactor or a perfusion bioreactor. Non-limiting examples and different aspects of culturing cells (e.g., culturing mammalian cells) are described below and can be used in any combination.

Cells

The cells that are cultured in some of the processes described herein can be bacteria (e.g., gram negative bacteria), yeast (e.g., *Saccharomyces cerevisiae, Pichia pastoris, Hansenula* polymorphs, *Kluyveromyces lactis, Schizosaccharomyces pombe, Yarrowia lipolytica,* or *Arxula adeninivorans*), or mammalian cells. The mammalian cell can be a cell that grows in suspension or an adherent cell. Non-limiting examples of mammalian cells that can be cultured in any of the processes described herein include: Chinese hamster ovary (CHO) cells (e.g., CHO DG44 cells or CHO-K1s cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, and Madin-Darby Canine (Cocker Spaniel) kidney epithelial cells (MDCK) cells. In some examples where an adherent cell is cultured, the culture can also contain a plurality of microcarriers (e.g., microcarriers that contain one or more pores). Additional mammalian cells that can be cultured in any of the processes described herein are known in the art.

The mammalian cell can contain a recombinant nucleic acid (e.g., a nucleic acid stably integrated in the mammalian cell's genome) that encodes a recombinant therapeutic protein. Non-limiting examples of recombinant nucleic acids that encode exemplary recombinant therapeutic proteins are described below, as are recombinant therapeutic proteins that can be produced using the methods described herein. In some instances, the mammalian cell that is cultured in a bioreactor (e.g., any of the bioreactors described herein) was derived from a larger culture.

A nucleic acid encoding a recombinant therapeutic protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant therapeutic protein is not stably integrated into a chromosome of the mammalian cell (transient transfection), while in others the nucleic acid is integrated. Alternatively or in addition, the nucleic acid encoding a recombinant therapeutic protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant therapeutic protein is a secreted protein and is released by the mammalian cell into the extracellular medium (e.g., the first and/or second liquid culture medium). For example, a nucleic acid sequence encoding a soluble recombinant therapeutic protein can contain a sequence that encodes a secretion signal peptide at the N- or C-terminus of the recombinant therapeutic protein, which is cleaved by an enzyme present in the mammalian cell, and subsequently released into the extracellular medium (e.g., the first and/or second liquid culture medium).

Culture Media

Liquid culture media are known in the art. The liquid culture media (e.g., a first and/or second tissue culture medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid culture medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different media.

Additional Features of Exemplary Bioreactors

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system).

Temperature

The step of culturing of mammalian cells can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the cell (e.g., mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

$CO_2$

The culturing step described herein can further include exposing the liquid culture medium in the bioreactor to an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

Perfusion Bioreactor

The culturing step described herein can be performed using a perfusion bioreactor. Culturing a cell (e.g., a mammalian cell) in a perfusion bioreactor includes the removal from the bioreactor of a first volume of a first liquid culture medium (e.g., containing any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by a mechanical system that can remove the first volume of the first liquid culture medium from the bioreactor (e.g., the first volume of the first liquid culture medium that is substantially free of cells from the bioreactor). Alternatively or in addition, the first volume of the first liquid culture medium can be removed by seeping or gravity flow of the first volume of the first liquid culture medium through a sterile membrane with a molecular weight cut-off that excludes the cell (e.g., mammalian cell).

The second volume of the second liquid culture medium can be added to the first liquid culture medium in an automated fashion, e.g., by perfusion pump.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

Fed-Batch Bioreactor

The culturing step described herein can be performed using a fed-batch bioreactor. Culturing a cell in a fed-batch bioreactor includes, over the majority of the culturing period, the addition (e.g., periodic or continuous addition) to the first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media. In other instances, the first liquid culture medium and the second liquid culture medium can be different. The volume of the second liquid culture medium can be added to the first liquid culture medium in an automated fashion, e.g., by perfusion pump.

In some instances, adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell. The cell culture medium in fed-batch cultures is typically harvested at the end of culture period and used in any of the processes described herein, however, the cell culture medium in fed-batch cultures can also be harvested at one or more time points during the culturing period and used in any of the processes described herein.

Skilled practitioners will appreciate that any of the various culture parameters (e.g., containers, volumes, rates or frequencies of replacing culture volumes, agitation frequencies, temperatures, media, and $CO_2$ concentrations) can be used in any combination in to perform these methods.

Further, any of the mammalian cells described herein or known in the art can be used to produce a recombinant protein.

Exemplary Advantages

The processes described herein can result in a substantial increase in the volumetric productivity of the recombinant therapeutic protein present in the therapeutic protein drug substance. For example, the processes described herein can result at least a 2-fold, 3-fold, 4-fold, 5-fold, 6-fold, 7-fold, 8-fold, 9-fold, and 10-fold increase in the volumetric productivity of the recombinant therapeutic protein present in the therapeutic protein drug substance. The biological activity of a recombinant therapeutic protein can be assessed using a variety of methods known in the art, and will depend on the activity of the specific recombinant therapeutic protein. For example, the biological activity of a recombinant therapeutic protein that is an immunoglobulin (e.g., an antibody or an antibody fragment) can be determined by measuring the affinity of the recombinant therapeutic antibody to bind to its specific epitope (e.g., using Biocore or competitive enzyme-linked immunosorbent assays). The recombinant therapeutic protein may be an enzyme (e.g., a recombinant galactosidase, e.g., a recombinant alpha-galactosidase) and the biological activity may be determined by measuring the recombinant therapeutic enzyme's activity (e.g., determining the catalytic rate constant of the recombinant therapeutic enzyme by measuring a decrease in the concentration of a detectable substrate or an increase in the concentration of a detectable product (e.g., using spectrophotometry or light emission). For example, the biological activity of a recombinant therapeutic galactosidase can be detected by measuring a decrease in the level of globotriasylceramide (GL-3) or galabiosylceramide, or an increase in the level of ceramide dihexoside or galactose.

The processes described herein can result in an increased percentage of recovery of the recombinant therapeutic protein (e.g., increased percentage of yield of the recombinant therapeutic protein present in the liquid culture medium in the therapeutic protein drug substance). For example, the present processes can result in a percentage yield of recombinant therapeutic protein of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The present processes can result in a percentage yield of between about 80% to about 90%, between about 82% to about 90%, between about 84% to about 90%, between about 84% to about 88%, between abour 84% to about 94%, between about 82% to about 92%, or between about 85% to about 95%.

The concentration of recombinant therapeutic protein present in the therapeutic protein drug substance can be greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL.

The processes described herein can result in a net yield of recombinant therapeutic protein in the therapeutic protein drug substance of at least about 5 g/day, at least about 6 g/day, at least about 7 g/day, at least about 8 g/day, at least about 9 g/day, at least about 10 g/day, at least about 11 g/day, at least about 12 g/day, at least about 13 g/day, at least about 14 g/day, at least about 15 g/day, at least about 16 g/day, at least about 17 g/day, at least about 18 g/day, at least about 19 g/day, at least about 20 g/day, at least about 25 g/day, at least about 30 g/day, at least about 35 g/day, or at least about 40 g/day over a continuous period of at least about 5 days, at least about 10 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 110 days, at least about 120 days, at least about 130 days, at least about 140 days, at least about 150 days, at least about 160 days, at least about 170 days, at least about 180 days, at least about 190 days, at least about 200 days, at least about 210 days, at least about 220 days, at least about 230 days, at least about 240 days, at least about 250 days, at least about 260 days, at least about 270 days, at least about 280 days, at least about 290 days, at least about 300 days, at least about 310 days, at least about 320 days, at least about 330 days, at least about 340 days, at least about 350 days, or at least about 365 days.

The processes provided herein can result in a significantly improved specific productivity rate. For example, the specific productivity rate achieved in the recombinant protein drug substance is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold greater than the specific productivity rate achieved using a different process (e.g., a batch purification process or a process that is not integrated and/or continuous). The productivity in the recombinant protein drug substance achieved by the present processes can be at least 10,000 units/L, at least 15,000 units/L, at least about 20,000 units/L, at least about 25,000 units/L, at least about 30,000 units/L, at least about 35,000 units/L, or at least about 40,000 units/L (in the first and/or second liquid culture medium). The productivity in the recombinant protein drug substance achieved by the present methods can be at least 1 g/L, at least 1.5 g/L, at least 2.0 g/L, at least 2.5 g/L, at least 3.0 g/L, at least 4.0 g/L, at least 4.5 g/L, or at least 5.0 g/L.

The processes described herein also provide for time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS is, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and about 20 hours, between about 10 hours and about 18 hours, between about 10 hours and about 16 hours, between about 10 hours and about 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the fluid (e.g., a liquid culture medium) containing a therapeutic protein into the first MCCS and eluting a therapeutic protein drug substance (containing the therapeutic protein) from the outlet of the second MCCS is, e.g., greater than about 4 hours and is less than about 40 hours, inclusive, e.g., greater than 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive. The invention is further described in the following examples, which do not limit the scope of the invention described in the claims.

EXAMPLES

Example 1

Use of a Single Periodic Counter-Current Chromatography System (PCCS) in the Continuous Flow Processing of a Recombinant Therapeutic Protein A set of initial experiments was performed in order to test parameters necessary for the successful use of a single PCCS in the continuous flow processing of a recombinant therapeutic protein.

Materials and Methods

Cell Culture

Bioreactors with a working volume of 12 L (Broadley-James Corp., Irvine, Calif.) were operated in perfusion mode utilizing the ATF (Refine Technologies) cell retention system with polyethersulfone 0.2-μm filters. Sintered spargers (20-μm) were used for $O_2$ gas to maintain the dissolved $O_2$ set point, and drilled-hole spargers (990-μm) were used for $N_2$ gas to maintain the $pCO_2$ set point. Cell density in the cell culture was monitored by offline measurements (Vi-CELL, Beckman Coulter, Brea, Calif.) and/or via online capacitance probes (Futura, Aber Instruments, Grand Island, N.Y.).

The bioreactor cell culture process runs utilized chemically-defined culture media and Chinese hamster ovary (CHO) cell lines that secrete recombinant therapeutic antibodies or recombinant therapeutic human enzymes. The cell concentration in the bioreactor culture immediately following inoculation was $0.5 \times 10^6$ cells/mL. The cells were allowed to grow to 50-60×10$^6$ cells/mL. Once the culture reached this cell density, cell-bleeding methods were initiated to maintain cell density at a steady state. Perfusion of the cell culture began at 24-h after inoculation, at 1 reactor volume/day, with the rate of perfusion increased proportional to the cell concentration in the culture. A steady-state cell specific perfusion rate of 0.04-0.05 nL/cell-d was maintained. Dissolved O$_2$ in the bioreactor was kept above 30% of air saturation. pH in the culture medium was maintained between 6.8 and 6.95 through sodium carbonate addition. Antifoam (FoamAway, GIBCO, Grand Island, N.Y.) was added to the liquid culture medium to control foam levels. The liquid culture medium obtained from the bioreactors was pumped onto the single PCCS without additional clarification.

Periodic Counter-Current (PCC) Chromatographic System (PCCS)

The PCCS used in these experiments was a custom-modified ÄKTA (GE Healthcare, Piscataway, N.J.) system capable of running up to four columns. The system was equipped with five UV monitors (UV-900), three pumps (P-900), multiple valves (PV-908, SV-903), one pH and one conductivity meter (pH/C-900), and Unicorn-based custom software (GE Healthcare, Piscataway, N.J.).

Breakthrough Curves

Protein breakthrough curves are required to determine the appropriate column switching strategy for the single PCCS. To obtain breakthrough curves under the capture conditions, frontal loading experiments were performed. The dynamic binding capacity (DBC) was evaluated as a function of residence time using clarified harvest and breakthrough profiles measured by UV absorbance (280 nm). Column sizes of 6.0-mL and 1.0-mL were used for the determination of DBC for the recombinant therapeutic antibody and recombinant therapeutic human enzyme, respectively. The residence times were selected such that they were sufficiently long to satisfy the binding capacity requirements, while also ensuring that the loading time was longer than the rest of the column operations (wash, elution, regeneration, etc.). Accordingly, the loading flow rate was adjusted to achieve a target residence time of 2.5 minutes for the recombinant therapeutic antibody and 4.8 minutes for the recombinant therapeutic human enzyme.

Integration of the Single PCCS to the Bioreactor

In PCCSs, the residence time (RT) of the protein on the column can be decreased without increasing the column size because the breakthrough from the first column in the system can be captured on the second column in the system. This unique feature was used to design a continuous process such that the culture harvest could be processed at any perfusion rate (D) by varying the column volume (V) and RT, as outlined by Eq. 1:

$$V = D * RT \tag{1}$$

Figure 2:
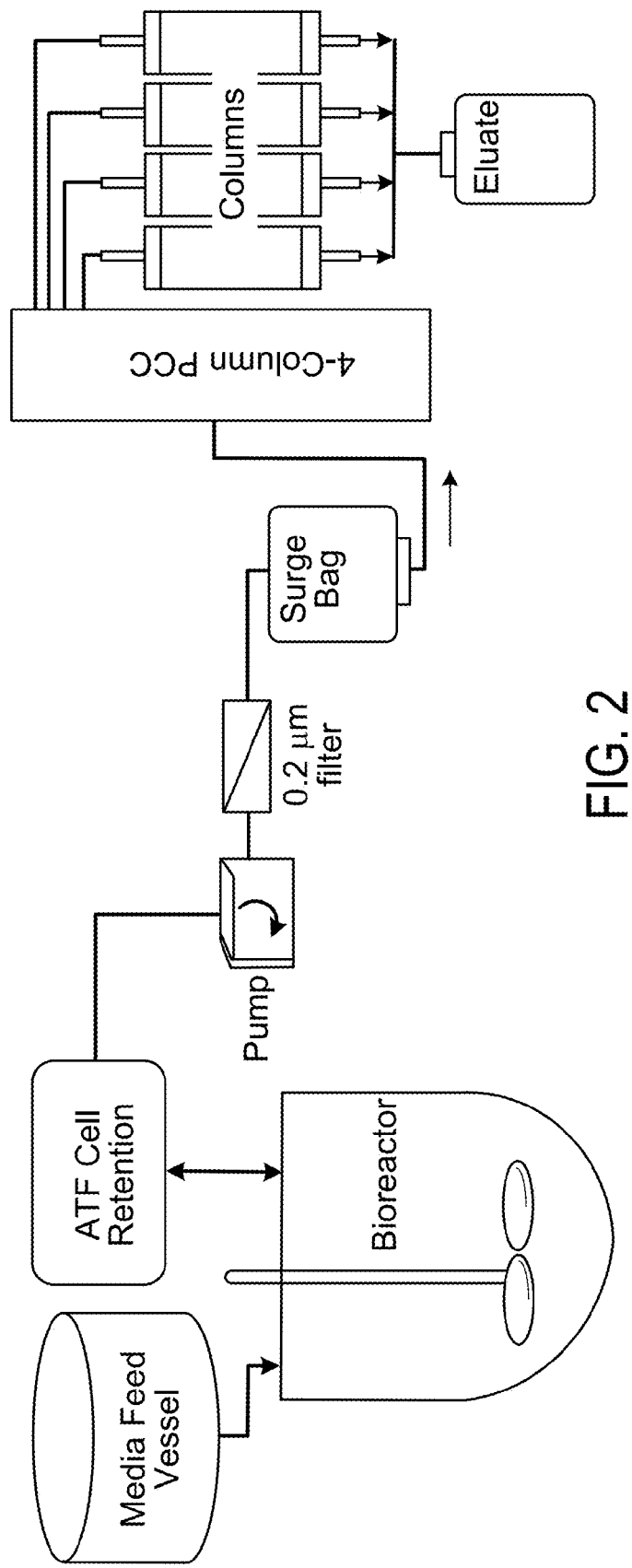
FIG. 2 is a diagram of the single PCC system connected to a perfusion cell culture bioreactor that can be used to capture a recombinant therapeutic protein present in the cell culture medium obtained from the bioreactor.

To achieve continuous capture of the recombinant protein, the single PCCS was directly connected to the bioreactor as shown in FIG. 2. The harvest from the bioreactor/ATF was pumped into a 2-L disposable bag serving as a small surge vessel (Hyclone, Logan, Utah) using a peristaltic pump (Masterflex, Cole-Parmer, Vernon Hills, Ill.). A 0.2-μm filter (Millipack 40, Millipore, Billerica, Mass.) was added between the bioreactor and the surge bag as an additional sterile barrier. MabSelect SuRe (GE Healthcare, Piscataway, N.J.) and a Hydrophobic Interaction Chromatography (HIC) media in a XK16', 1.6-cm×6-cm (GE Healthcare) column was used to capture the recombinant therapeutic antibody and the recombinant therapeutic human enzyme, respectively). The operation of each column consisted of equilibration, load, wash, elution, and regeneration steps. Since the engineering of the bench-scale single PCCS did not allow for closed operation, sodium azide was added to the process stream in-line.

Analytical Methods

Recombinant Therapeutic Antibodies

In-house assays were used for the quantitation of the titer of host cell proteins (HCP), aggregation, residual protein A, and potency of the recombinant antibodies. Titer was measured using a Protein A column (Applied Biosystems, Carlsbad, Calif.). Residual protein A and HCP were quantitated by ELISA using antigen and antibodies produced in-house. Aggregation was measured by HPLC-SEC using a TSK-GEL, G3000SWXL, 7.8 mM×30 cm, 5-μm column (TOSO HAAS, King of Prussia, Pa.). Recombinant therapeutic antibody potency was measured by an in vitro cell-based assay.

Recombinant Therapeutic Human Enzyme Activity Assay

The titer of recombinant therapeutic human enzyme in the column load and eluate was determined by measuring the hydrolysis rate of a synthetic substrate linked to p-nitrophenol (pNP) (Sigma Aldrich, St. Louis, Mo.). The samples (25-μL) were incubated with 225 μL of 40 μM substrate for 15 minutes at 37° C. The reactions were quenched with 250 μL of 0.3 M glycine, pH 10.5, and the absorbance was measured at 400 nm. One unit of activity was defined as the amount of recombinant therapeutic enzyme required to hydrolyze one micromole of substrate to pNP per minute under the defined assay conditions. Protein concentration was determined by RP-HPLC using a POROS R2/H 2.1×30 mM column (Applied Biosystems, Carlsbad, Calif.). The specific activity was expressed as pNP (units)/mg protein In-house assays were used for the quantitation of HCP, aggregation, and purity. HCP was assayed by ELISA using proprietary reagents. The aggregation (SEC-HPLC) assay used a TSK-GEL, G3000SWXL, 7.8 mM×30 cm, 5-μm column (TOSO HAAS, King of Prussia, Pa.), while the RP-HPLC purity assay used a YMC Octyl 2 mm×100 mM, 5-μm column (Waters, Milford, Mass.).

Basic Concepts of the Single PCCS

A column operation generally consists of the load, wash, eluate, and regeneration steps. In the single PCCS, multiple columns are used to run the same steps discretely and continuously in a cyclic fashion. Since the columns are operated in series, the flow through and wash from one column is captured by a second column. This unique feature of PCC systems allows for the loading of the resin close to its static binding capacity instead of to the dynamic binding capacity, as is typical during batch-mode chromatography. For the ease of illustration only, a 3-column system is used to describe this principle of PCCS operation (FIG. 3). A cycle is defined as three complete column operations resulting in three discrete elution pools. Once all the steps in a cycle are completed, the cycle is re-started. As a result, the feed stream is processed continuously in an operating PCC system, while recombinant therapeutic protein elution from each column is discrete and periodic.

Column Switching Strategy

To advance from one step to another within a PCCS cycle (FIG. 3), a column switching strategy is employed. There are two automated switching operations required per column in the PCCS, the first of which is related to the initial recombinant therapeutic protein breakthrough, while the second coincides with column saturation. The single PCCS described in this example was operated using a control strategy utilizing dynamic UV monitoring. In general, column switching can be determined by any Process Analytical Technology (PAT) tool capable of in-line measurement of recombinant therapeutic protein concentration with feedback control. However, a PAT tool that operates in real-time, such as UV, is ideal for providing the trigger signal for column switching.

FIG. 4 illustrates the principle of column switching based on the UV absorbance difference (ΔUV) between the feed inlet and column outlet. During column loading (Step 1; FIG. 3), the PCC control system determines the impurity baseline when the absorbance stabilizes. As the recombinant therapeutic protein breaks through (Step 2; FIG. 3), there is an increase in the outlet UV signal above the impurity baseline. At the point when ΔUV has reached a pre-determined threshold (such as 3% breakthrough of the recombinant therapeutic protein), the flow-through from column 1 is directed onto column 2 instead of to the waste (t1; FIG. 4). When column 1 is nearly saturated with recombinant therapeutic protein and the ΔUV has reached a pre-determined value (t2; FIG. 4), the feed is switched to column 2. An important advantage of this ΔUV-based column switching strategy is that it allows for uniform loading of the columns irrespective of the feed recombinant therapeutic product concentration and the column capacity. Within a reasonable range, the strategy is adequate for harvest titer variability, thereby enhancing system robustness.

Accurate determination of the column-switching time, which is based on the UV absorbance difference between the feed and column outlet, is one of the critical elements of the single PCCS real-time control strategy. This requires synchronization of all five UV detectors (one feed and four column outlet detectors) within a narrow range. The UV detectors were calibrated using a 3% acetone solution. The detector path lengths were manually adjusted so that all five absorbance values were within 0.5% of one another. The path length adjustment was ≥10%.

Proof of Concept Using a Recombinant Antibody
Cell Culture

Figure 5A:
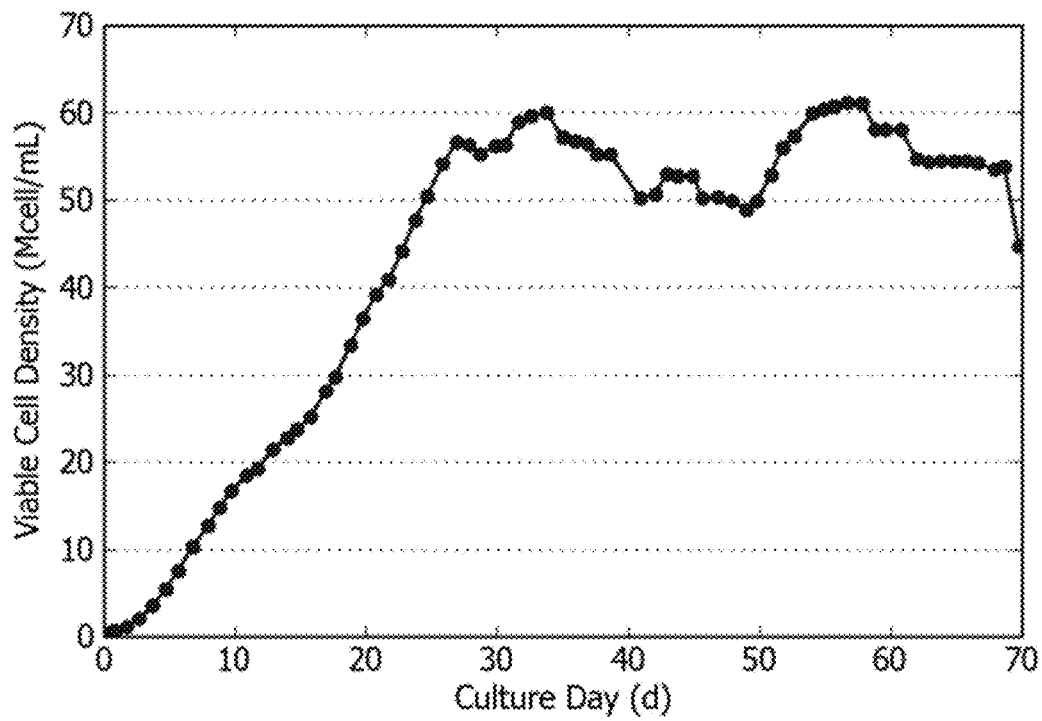
FIG. 5A is a graph of the cell density profile over time in the bioreactor culture producing the recombinant therapeutic antibody. The average cell density in the bioreactor culture was $50\text{-}60 \times 10^6$ cells/mL.
Figure 5B:
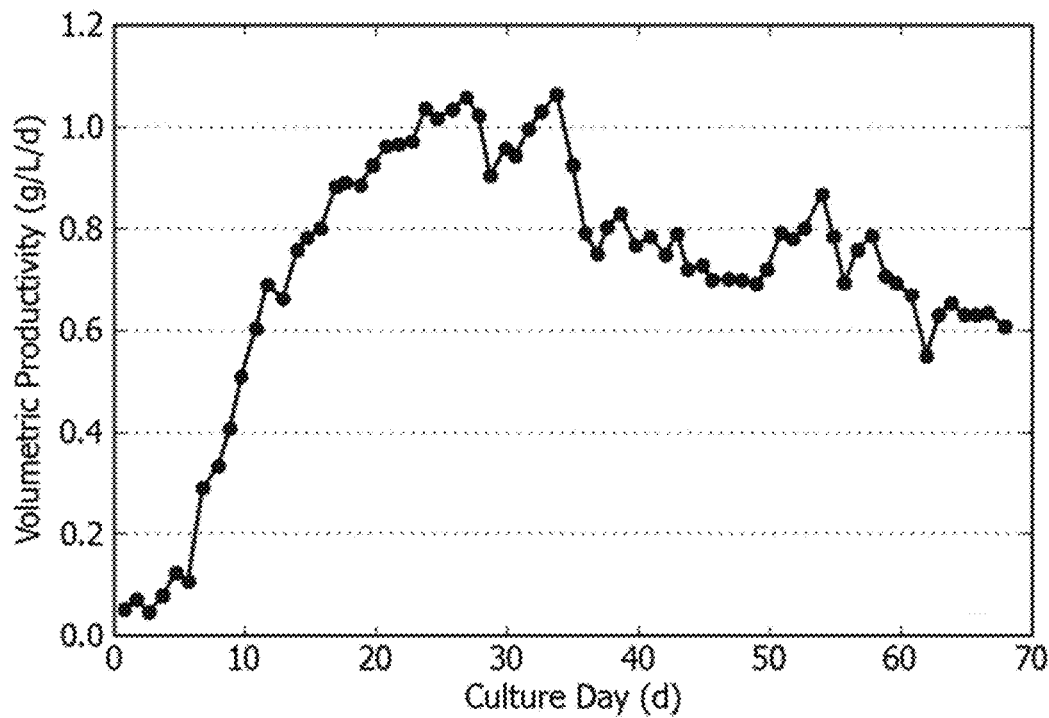
FIG. 5B is a graph of the volumetric productivity rate over time of the bioreactor culture producing the recombinant therapeutic antibody.

The model recombinant therapeutic antibody for this study was produced continuously over a 70-day period in a 12-L perfusion bioreactor under the conditions described in Materials and Methods (FIG. 5). The volumetric productivity rate reached 1 g/L-d between days 30 and 40, then slowly declined for reasons that are yet to be determined. The peak volumetric productivity rate was >5 fold higher than the fed-batch process using the same cell line, with a significant upward potential for the continuous process. It should be noted that the objective of the study was to demonstrate the functionality of the integrated continuous system. In fact, the volumetric production rate change allowed for the testing of the robustness of the single PCCS and, particularly, its ability to handle variability in harvest titer.

Downstream

In batch chromatography, maximum DBC is achieved by increasing the residence time (RT) and subsequently oversizing the column. In PCCSs, the RT can be decreased without increasing the column size because the breakthrough from first column can be captured on the second column. This advantage in PCCSs allows for smaller column sizes and shorter RT. In order for the single PCCS process to be continuous, RT has to be longer than the combined time taken by the rest of the process (equilibration, wash, elution, regeneration, etc.). Therefore, the size and number of columns to be used with a PCCS for a given process are dependent on the resin binding capacity, which dictates the length of the load step. The high-binding capacity of the MabSelect SuRe™ resin in the recombinant antibody process (50 g/L) leads to a load step that is longer than the rest of the column steps combined, which allows for continuous recombinant therapeutic protein capture using a PCCS containing three columns. Frontal loading experiments were utilized to determine the breakthrough curves at different residence times for the recombinant antibody (data not shown), and a residence time of 2.5 minutes was found to be optimal.

Figure 6:
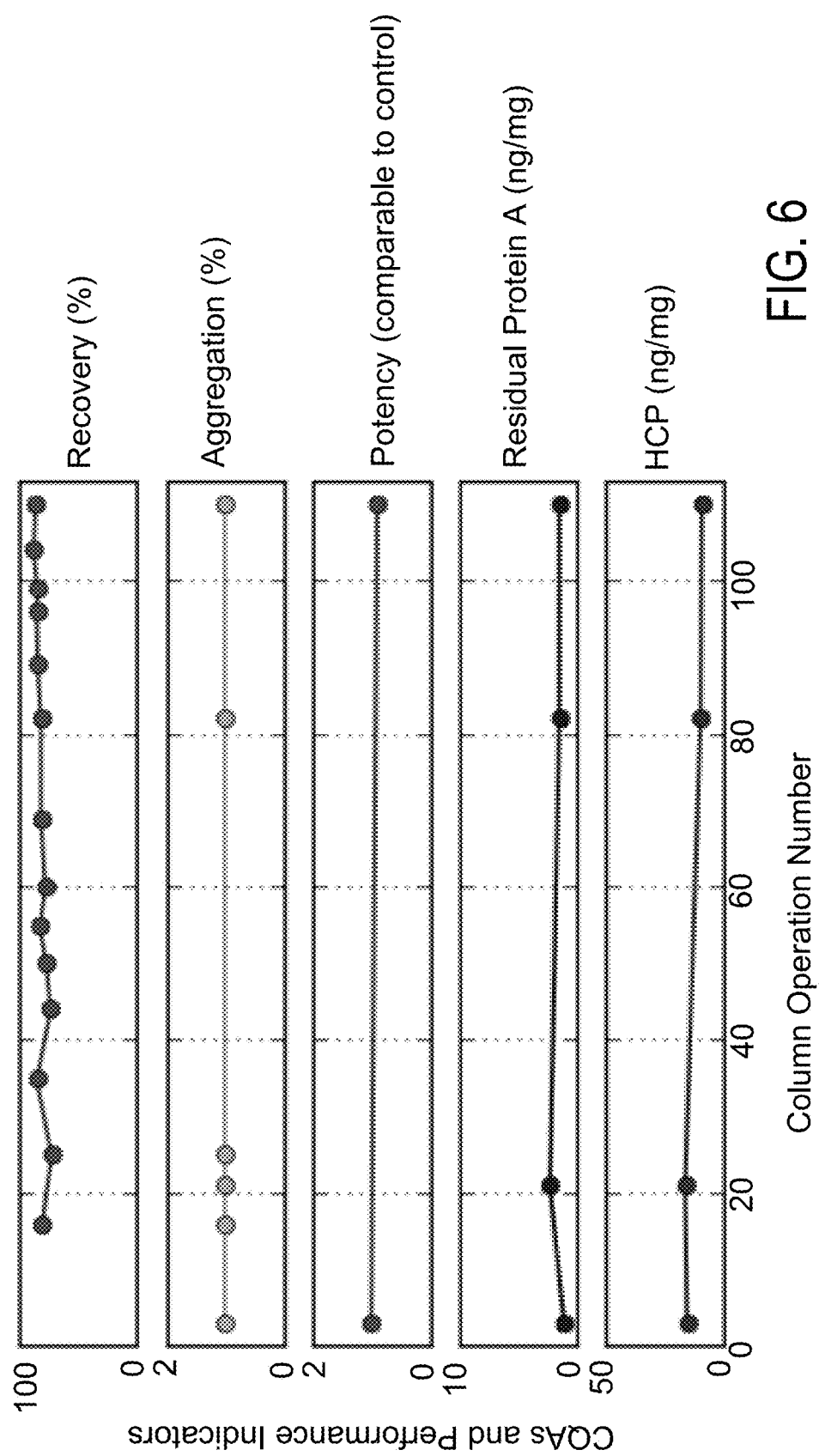
FIG. 6 is a set of graphs showing the percent recovery, percent aggregation, potency (as compared to control), residual protein A concentration (ng/mg), and host cell protein concentration (ng/mg) in the recombinant therapeutic protein eluted from the single PCC system over a total of 30 days, 38 single PCC system cycles, and 110 column operations. The variability associated with the three ELISA assays (recovery, residual protein A, and host cell protein) was ±20%. All of the data shown are within the assay variability.

To test the long-term performance of the single PCCS, bioreactor harvest was continuously captured for 30 days, which corresponds to 38 PCC cycles and 110 column operations, without any indications of time-based performance decline. The consistency of the continuous capture over the study duration was evaluated based on several performance indicators, such as chromatographic profile, recoveries, and recombinant antibody Critical Quality Attributes (CQAs). The UV profile of the feed stream was nearly constant over the duration of the run, and the 3 column UV outlets were reproducible across various cycles. The recovery and five CQAs analyzed for the capture eluate were comparable between the 3 columns, as well as over the entire period of continuous harvest capture (FIG. 6). These results demonstrated the feasibility of the direct continuous recombinant antibody capture from a perfusion bioreactor, yielding consistent process performance indicators and CQAs over a prolonged period of time.

The single PCCS process was compared to an existing single column batch chromatography system in terms of the estimated chromatography column footprint and raw material consumption. Specifically, chromatography media capacity utilization was increased by 20%, buffer usage was reduced by 25%, and individual column size was reduced 75 fold, in the single PCCS as compared to batch-mode purification.

Proof of Concept with Recombinant Human Enzyme
Cell Culture

Figure 7A:
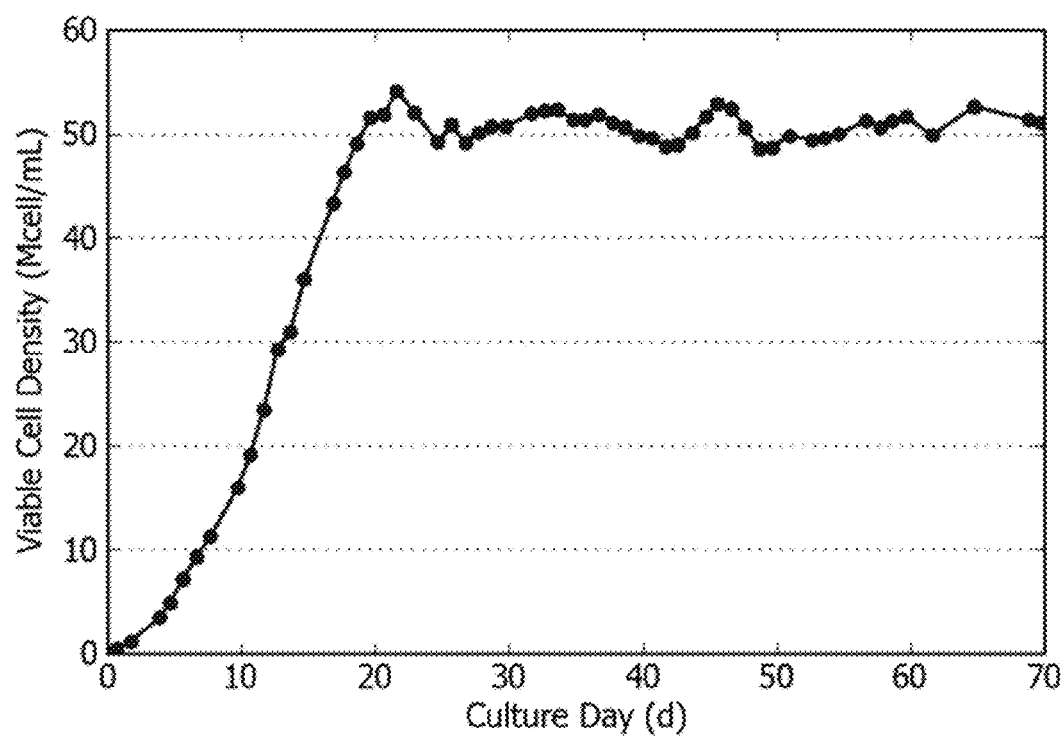
FIG. 7A is a graph of the cell density profile over time in the bioreactor culture producing the recombinant therapeutic human enzyme. The average cell density in the bioreactor culture after day 19 was $50\text{-}60 \times 10^6$ cells/mL.
Figure 7B:
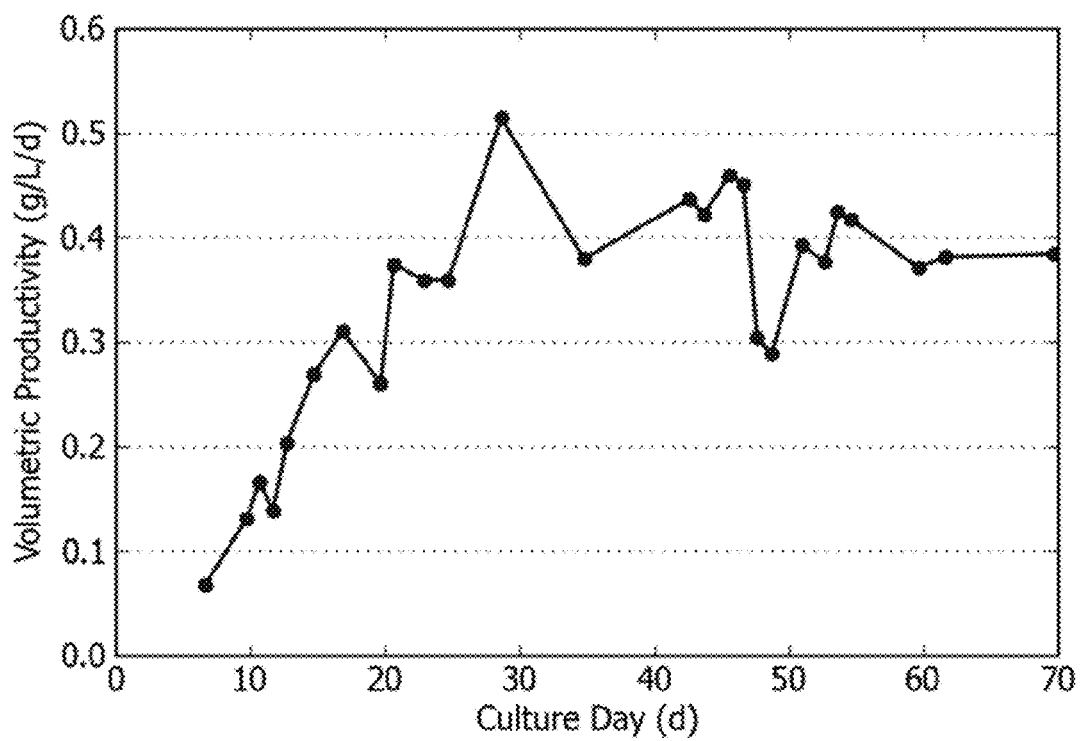
FIG. 7B is a graph of the volumetric productivity rate over time of the bioreactor culture producing the recombinant therapeutic human enzyme. The two low titer values determined around day 48-49 are believed to be due to assay variability as there were no changes in cell density, perfusion rate, or metabolism over this period.

The recombinant therapeutic human enzyme in this study was produced over a 70-day continuous cultivation in a 12-L bioreactor under the conditions described in Materials and Methods (FIG. 7). The volumetric productivity rate reached 0.4 g/L-d around day 25, and remained steady after that with a CV of 16%, largely related to assay variability. Compared to the legacy process for the manufacture of the same molecule, this volumetric productivity is ~40 fold higher, which is a result of the synergistic impact of the high cell density and the significantly improved cell specific production rate.

Downstream

The objective of this study was to determine the consistency of the capture column performance indicators, CQAs of the capture eluate across the columns and cycles, and the robustness of the single PCCS hardware and control strategy over extended periods of time. Given that the binding capacity of the HIC capture column was low (1 g/L resin), the time required to load a column was shorter than the rest of the process steps combined (wash, elution, regeneration, etc.). This resulted in a single PCCS where 4 columns, instead of 3 columns, were required for the harvest to be processed continuously. Therefore, a single 4-column PCCS was developed and used to continuously capture the recombinant human enzyme.

Figure 8:
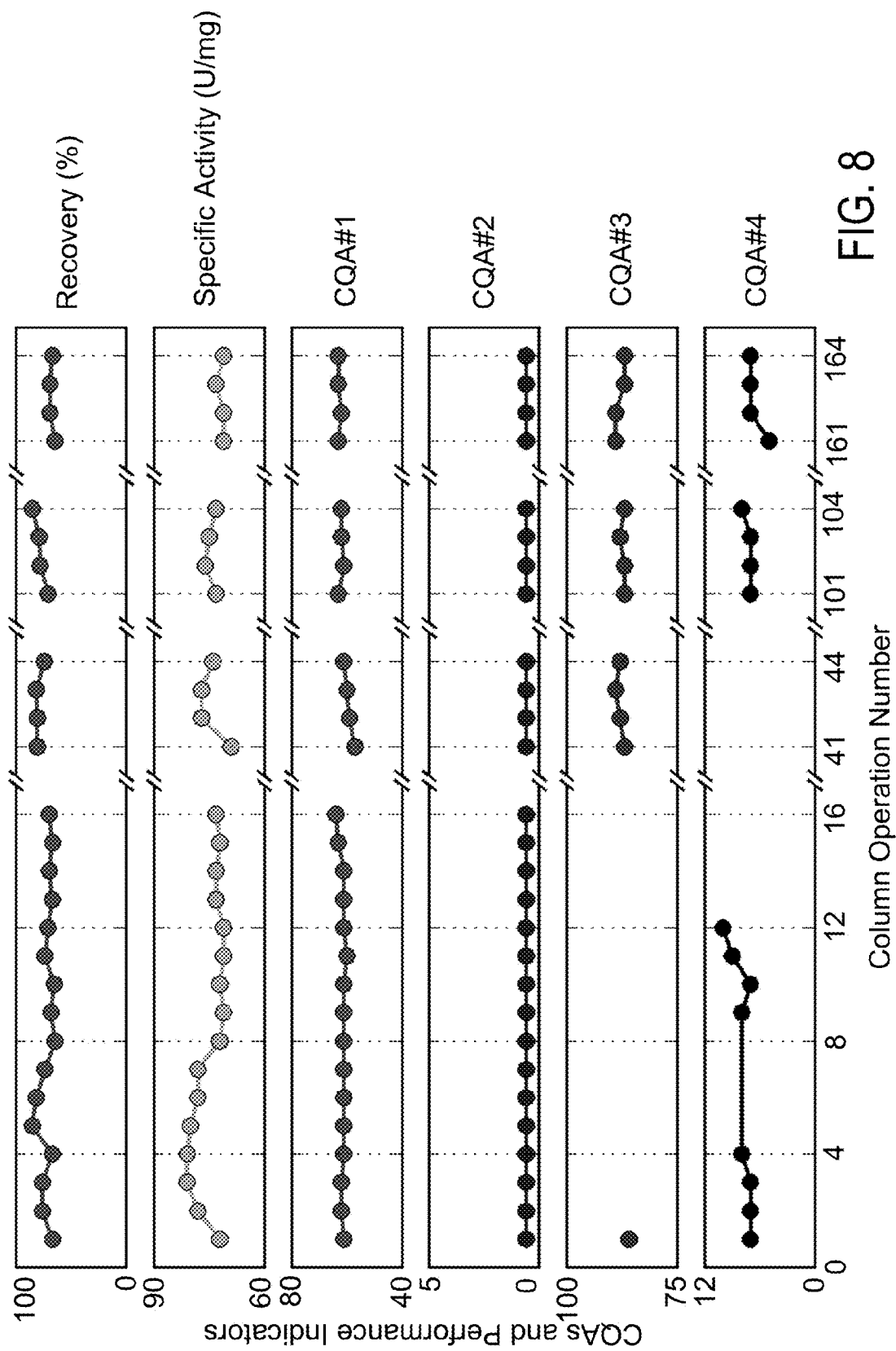
FIG. 8 is a set of graphs showing the percent recovery, specific activity (units/mg), percent aggregation, potency (as compared to control), Critical Quality Attribute (CQA) #1, CQA #2, CQA #3, and CQA #4 in the recombinant therapeutic human enzyme eluted from the single PCC system over a total of 9 days, 41 single PCC system cycles, and 164 column operations. CQAs #3 and #4 have limited data points, but represent the entire operational duration. The standard deviation of the CQAs is in the range of 1-9%.

The study was divided into two phases. The first phase consisted of method development, where previously collected harvest was fed to the single PCCS from a sterile disposable bag. During the second phase, the single PCCS was directly integrated with the bioreactor for continuous processing, as outlined in FIG. 2. In the first phase of this study, the single PCCS was operated continuously for 9 days and 41 single PCCS cycles or 164 column operations. The UV profile of the feed was constant over the entire run, and the 4 column outlet UV signals were reasonably consistent among the 4 columns and across the various cycles. The consistency of the single PCCS operation during the entire run was demonstrated by the analysis of additional column performance indicators and CQAs of the captured recombinant therapeutic protein (FIG. 8). The recovery and the five CQAs analyzed were comparable between the four columns over the period of 9 days of continuous harvest capture.

In the second phase of this study, recombinant therapeutic protein was directly captured from a perfusion bioreactor by integrating the single PCCS with the bioreactor, as shown in FIG. 2. The main objective was to demonstrate the performance of the continuous bioprocessing platform with a highly complex, non-antibody protein over an extended period of time. The column size and RT were scaled according to Equation 1 in order to achieve continuous capture of the bioreactor harvest. The integrated single PCCS was operated continuously for 31 days and 160 single PCCS cycles, which corresponds to 640 independent column operations, without any signs of time-based performance decline. The feed UV profile, the 4 column outlet UV profiles and CQAs were consistent for the entire duration of the PCCS operation. Since the data were practically equivalent to those obtained in the first phase of the study, the time profiles are not shown.

In sum, these data indicate that a single PCCS can be used to process recombinant therapeutic proteins (both recombinant therapeutic antibodies and recombinant therapeutic human enzymes) produced by a mammalian cell culture.

Example 2

Use of a Two Periodic Counter-Current Chromatography Systems (PCCSs) in the Continuous Flow Processing of a Recombinant Protein A system using two different PCCSs was generated which allows for the continuous bioprocessing of a recombinant therapeutic antibody from a cell culture medium of a bioreactor. The eluate of the system containing the recombinant therapeutic antibody is substantially ready for formulation as a pharmaceutical composition and is unformulated therapeutic protein drug substance.

Materials and Methods
Cell Culture

Bioreactors with a working volume of 10 L (Broadley-James Corp., Irvine, Calif.) were operated in perfusion mode utilizing the ATF (Refine Technologies) cell retention system with polyethersulfone 0.2-μm filters. Sintered spargers (20-μm) were used for $O_2$ gas to maintain the dissolved $O_2$ set-point, and drilled-hole spargers (990-μm) were used for $N_2$ gas to maintain the $pCO_2$ set-point in the culture medium. Cell density in the bioreactor was monitored by offline measurements (Vi-CELL, Beckman Coulter, Brea, Calif.) and/or via online capacitance probes (Futura, Aber Instruments, Grand Island, N.Y.). The bioreactor cell culture process runs utilized chemically defined liquid culture media and a CHO cell line producing a recombinant therapeutic monoclonal antibody. After inoculation, the bioreactors contained in the liquid culture medium a viable cell concentration of $0.5 \times 10^6$ cells/mL. The cells were allowed to grow to a cell density of $30\text{-}40 \times 10^6$ cells/mL. Once the cells reached this density, cell bleeding-methods were initiated to maintain cell density at steady state. Perfusion began 24-h after inoculation, and the volume of liquid culture medium removed and replaced in the bioreactor increased proportionally with cell concentration. A steady state cell specific perfusion rate of 0.04-0.05 nL/cell-d was maintained. Dissolved $O_2$ was kept above 30% of air saturation in the liquid culture medium. The pH of the liquid culture medium was maintained between 6.8 and 6.95 through sodium carbonate addition. Antifoam (FoamAway, GIBCO, Grand Island, N.Y.) was used to control foam levels in the bioreactor. The liquid culture medium harvested from the bioreactors was pumped onto the two PCC system without additional clarification.

Downstream

Figure 9:
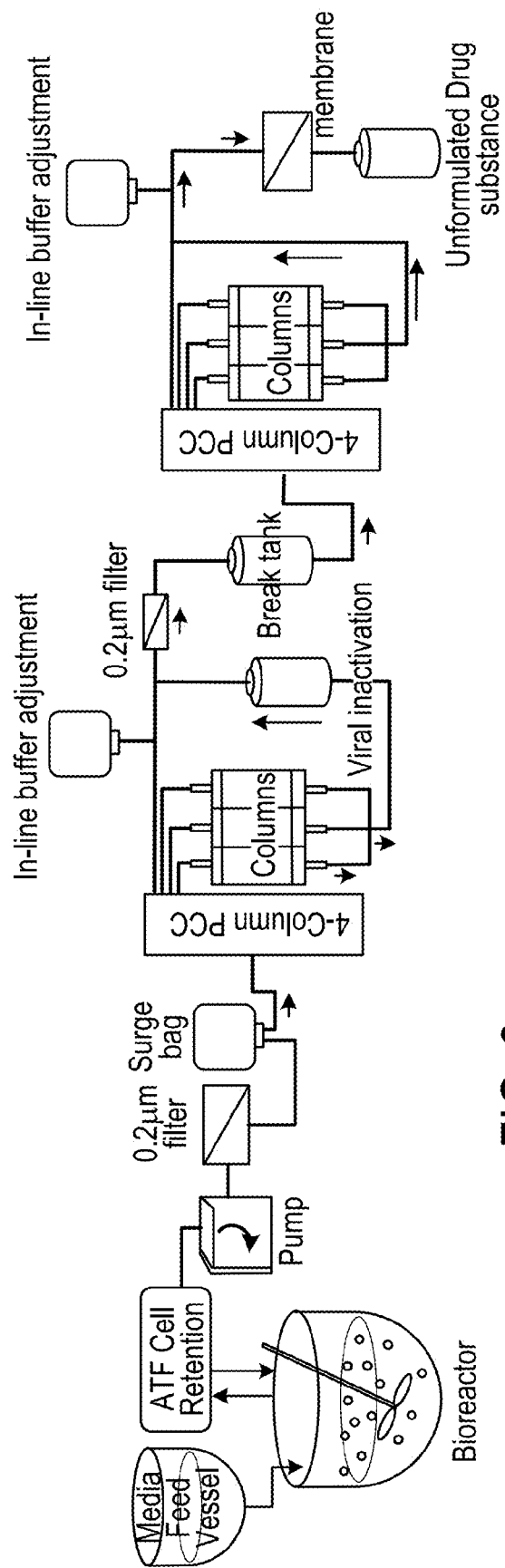
FIG. 9 is a schematic showing the two-PCCS manufacturing system connected with a perfusion culture bioreactor that results in the continuous manufacture of a therapeutic protein drug substance.
Figure 10:
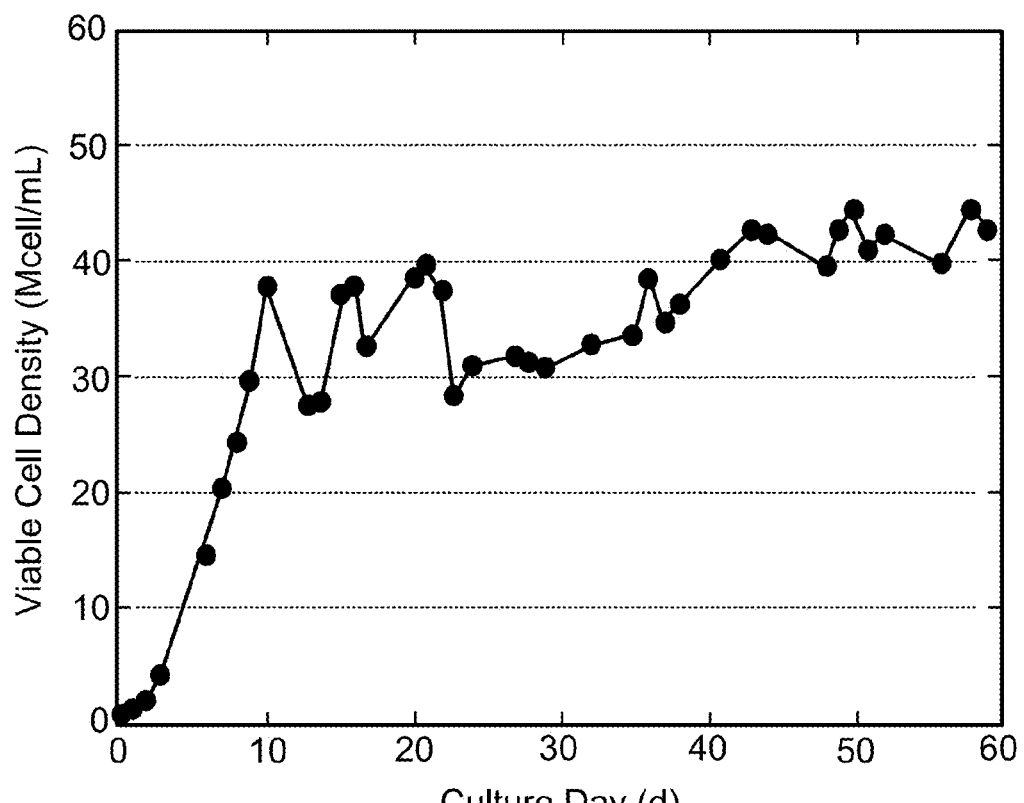
FIG. 10 is a graph of the viable cell density profile over time in the bioreactor culture producing the recombinant therapeutic monoclonal antibody. The average cell density in the bioreactor culture was $50\text{-}60 \times 10^6$ cells/mL.

In order to develop an integrated and fully continuous process for the production of recombinant protein drug substance (DS) two PCCSs (PCCS1 and PCCS2) were used (FIG. 9). Each PCCS performed multiple operations in addition to allowing the use of periodic counter current chromatography for continuous column operations. Since the engineering of the bench-scale PCCS did not allow for closed operation, sodium azide was added to the process stream in-line. This limitation of the small scale system can be successfully addressed by proper design of large scale PCCS hardware.

Two Periodic Counter-Current (PCC) Chromatographic System

The two PCCS used in this study were a custom modified ÄKTA (GE Healthcare, Piscataway, N.J.) capable of running up to four columns. Each system was equipped with five UV monitors (UV-900), three pumps (P-900), multiple valves (PV-908, SV-903), one pH and one conductivity meter (pH/C-900), and Unicorn basedcustom software (GE Healthcare, Piscataway, N.J.).

Integration of Bioreactor to PCCS1 and PCCS2

The harvest from the bioreactor/ATF was pumped into a 2-L disposable bag serving as a small surge vessel (Hyclone, Logan, Utah) using a peristaltic pump (Masterflex, Cole-Parmer, Vernon Hills, Ill.). A 0.2-μm filter (Millipack 40, Millipore, Billerica, Mass.) was added between the bioreactor and the surge bag as an additional sterile barrier. MabSelect SuRe (GE Healthcare, Piscataway, N.J.) Chromatographic media in a XK16™, 1.6 cm×6 cm column was used to capture the recombinant therapeutic monoclonal antibody. The eluate from each Protein A column (pH 3.75) was pumped into 250-mL glass, stirred reservoir with a residence time of 1 hr to perform a viral inactivation (VI) operation. A 0.2 μm-filter (Millipack 100, Millipore, Billerica, Mass.) was added between PCCS1 and PCCS2 to act as a mixing device and a particulate barrier for downstream columns.

Adjusted load material from PCCS1 was further purified on PCCS2, using three XK16™, 1.1 cm×7 cm (GE Healthcare) Capto S (GE Healthcare, Piscataway, N.J.) https://imc-apps:8002/sonora/Home chromatography columns in a bind and elute mode. Finally Capto S eluate was polished using a 7-mL SartoBind Q-membrane (Sartorious XX), connected directly to Capto-S column outlets to yield recombinant protein drug substance. Additionally, in-line dilution required prior to both loading on the Capto-S and SartoBind Q-membrane was performed using PCCS1 and PCCS2 pumps respectively (FIG. 9). Each column operation consisted of equilibration, load, wash, elution, and regeneration steps. The Sartobind Q-membrane consisted of equilibration, load, wash, and regeneration steps. Tables 1 and 2 show the process parameters for all the unit operations performed using PCCS1 and PCCS2, respectively. FIG. 9 also shows the flow rate for the liquids pumped through the two PCCSs.

TABLE 1

Operational Parameters of the First PCCS (PCCS1)

| Step description | Parameter | Value |
| --- | --- | --- |
| Capture by protein A column | Column size | (3 columns); 3.6 mL resin volume |
| | Load Titer | 0.6 mg/ml |
| | Load Flow rate | 0.36 CV/min |
| | Column residence time | 2.8 min |
| | Total time of capture per column | 5.4 hours (325 min) |
| | Load solo column | 75 min |
| | Load on two columns in series | 135 min (1.5 L) |
| | Elution flow rate | 0.13 CV/min |
| | Elution volume | 5 column volumes (CV) |
| | Elution time | 40 min |
| | Wash 1 volume | 4 CV |
| | wash 1 Time | 19 min |
| | Wash 2 volume | 6 CV |
| | wash 2 time | 28 min |
| | Regeneration volume | 3 CV |
| | Regeneration Time | 28 min |
| | protein Conc of the eluate | ~8 mg/ml |
| | Δ UV cut off 1 (t1) | 3 percenrt |
| | Δ UV cut off 2 (t2) | 70 percent |
| | percent recovery | 75 |
| Low pH hold | Time for hold | 60 min |
| | Hold pH | 3.75 |
| Buffer adjustment for S column load (In-line adjustment 1) | Flow rate of Protein A eluate transfer to PCC 2 | 0.5 CV/min |

TABLE 2

Operational Parameters for the Second PCCS (PCCS2)

| Step description | Parameter | Value |
| --- | --- | --- |
| Purifcation by Capto-S column | Column size | (3 columns); 6.7 mL resin volume |
| | Flow rate of transfer of S-load | 0.1 CV/min |
| | Load Titer | ~7 mg/ml |
| | Load Flow rate | 0.1 CV/min |
| | Load solo column | 86 min |
| | Load on two columns in series | 22 min |
| | Wash 1 volume | 2.5 CV |
| | wash 1 Time | 5 min |
| | Wash 2 volume | 2.5 CV |
| | wash 2 time | 5 min |
| | Elution flow rate | |
| | Elution volume | 17 CV |
| | Elution time | 40 min |
| | Regeneration volume | 5 CV |
| | Regeneration Time | 10 min |
| | protein Conc of the eluate | ~4.5 mg/mL |
| | Δ UV cut off 1 (t1) | 3 percenrt |
| | Δ UV cut off 2 (t2) | 70 percent |
| | percent recovery | 90 percenrt |
| In-line buffer dilution | Elution flow rate of adjustment buffer | 0.07 CV/min |
| sartobind Q membrane polish step | membrane volume (mem vol) | 7 mls |
| | membrane equilibration flow rate | 5 membrane volume/min |
| | Time of equilibration | 10 min |
| | Load of Q-membrane flow rate | 0.5 membrane vol/min |
| | Load time | |
| | Chase flow rate | 5 membrane vol/min |
| | Chase time | 2 min |
| | Regeneration flow rate | 5 membrane vol/min |
| | Regeneration time | 10 min |
| | Pertcent Recovery | 95 |
| | Protein concentration of the final therapeutic drug substance | ~3.5 mg/mL |

Analytical Methods

In-house assays were used for the quantitation of titer host cell proteins (HCP), aggregation, residual protein A, and recombinant monoclonal antibody potency. Titer was measured using a Protein A column (Applied Biosystems, Carlsbad, Calif.). Residual protein A and HCP were quantitated by ELISA using antigen and antibodies produced in-house. Aggregation was measured by HPLC-SEC using a TSK-GEL, G3000SWXL, 7.8 mM×30 cm, 5-μm column (TOSO HAAS, King of Prussia, Pa.). Recombinant therapeutic monoclonal antibody potency was measured by an in vitro cell-based assay.

Column Switching Strategy

To advance from one step to another within a PCCS cycle (FIG. 3), a column switching strategy is employed. There are two automated switching operations required per column in each PCC, the first of which is related to the initial recombinant therapeutic protein breakthrough, while the second coincides with column saturation. The PCC system described in this work was operated using either a novel control strategy utilizing dynamic UV monitoring as well as time based switching. In general, column switching can be determined by any PAT tool capable of in-line measurement of recombinant therapeutic protein concentration with feedback control FIG. 4 illustrates the principle of column switching based on the UV absorbance difference (ΔUV) between the feed inlet and column outlet. During column loading (Step 1; FIG. 3), the PCC control system determines the impurity baseline when the absorbance stabilizes. As the recombinant therapeutic protein breaks through (Step 2; FIG. 3), there is an increase in the outlet UV signal above the impurity baseline. At the point when ΔUV has reached a pre-determined threshold (such as 3% breakthrough of the recombinant therapeutic protein), the flow-through from column 1 is directed onto column 2 instead of to the waste (t1; FIG. 4). When column 1 is nearly saturated with recombinant therapeutic protein and the ΔUV has reached a pre-determined value (t2; FIG. 4), the feed is switched to column 2. An important advantage of this ΔUV-based column switching strategy is that it allows for uniform loading of the columns irrespective of the feed recombinant therapeutic protein concentration and the column capacity. Within a reasonable range, the strategy is adequate for harvest titer variability, thereby enhancing system robustness.

As discussed above, accurate determination of the column-switching time, which is based on the UV absorbance difference between the feed and column outlet, is one of the critical elements of the PCC real-time control strategy. This requires synchronization of all five UV detectors (one feed and four column outlet detectors) within a narrow range. The UV detectors were calibrated using a 3% acetone solution. The detector path lengths were manually adjusted so that all five absorbance values were within 0.5% of one another. The path length adjustment was ≤10%.

The second strategy used for column switching was with respect to time. Since the recombinant therapeutic protein titer over 31 days of production was quasi-steady state, the column switching could be calculated based on time it took for pre-determined threshold as well as saturation.

Results and Discussion

Figure 16:
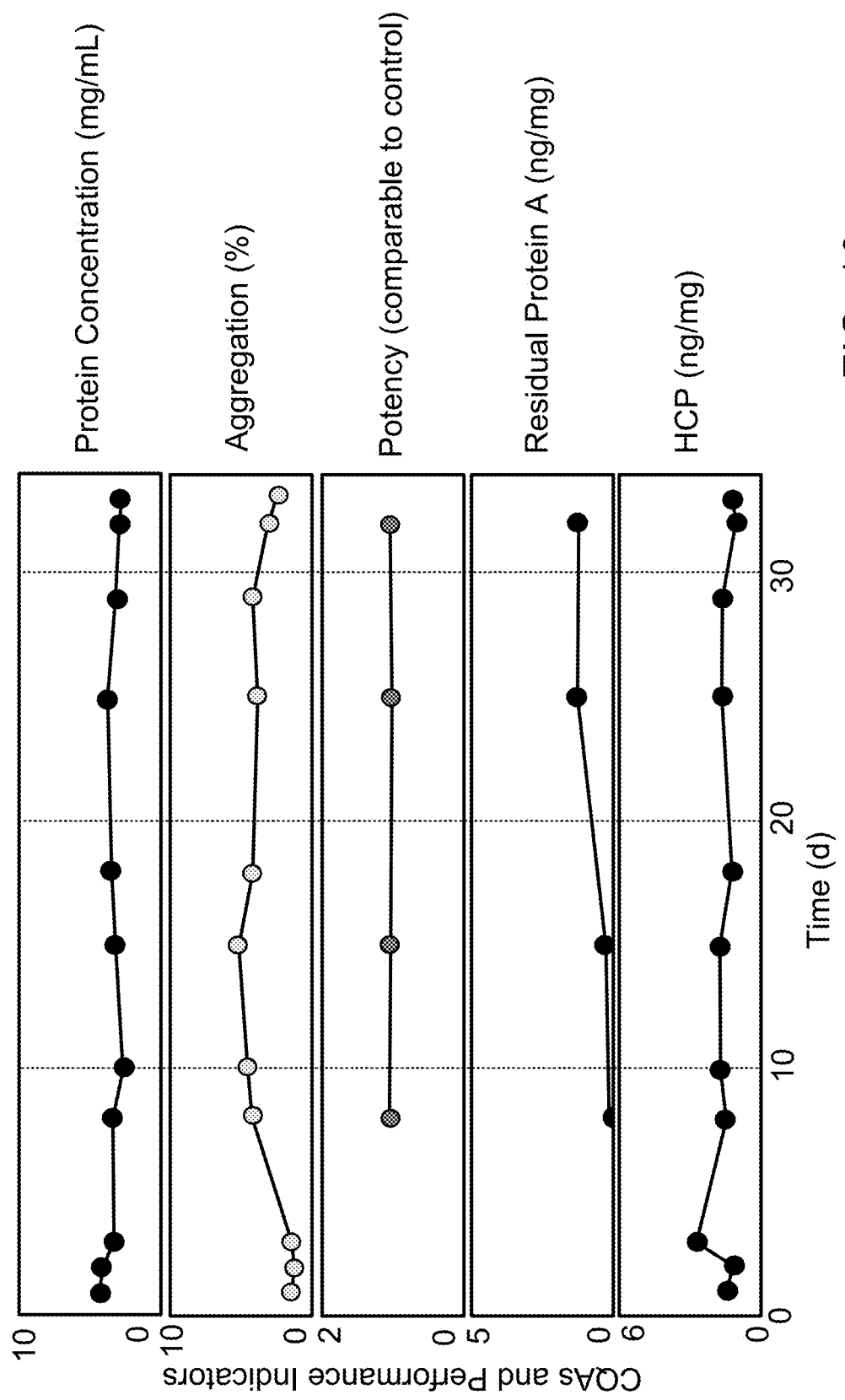
FIG. 16 is a set of graphs showing the protein concentration (mg/mL), percent aggregation, potency (as compared to control), residual protein A concentration (ng/mg), and host cell protein concentration (ng/mg) in the product eluted from the two-PCC system over a total of 31 days and 25 dual system batches. The variability associated with the aggregation and residual protein A measurements was due to the unoptimized Q membrane operation. The trends were, however, comparable between the batch and continuous operation. All the results above are within the assay variability.

To test the long-term performance of the two PCC system, the liquid culture medium harvested from the bioreactor was continuously purified for 31 days, which corresponds to 372 purification cycles, or 25 two PCC system batches of production, without any indications of time-based performance decline. The consistency of the continuous capture over the study duration was evaluated based on several performance indicators, such as chromatographic profile, recoveries, and recombinant therapeutic monoclonal antibody Critical Quality Attributes (CQAs). The UV profile of the feed stream was nearly constant over the duration of the run, and the 3 column UV outlets were reproducible across various cycles. These details and the cycle-to-cycle reproducibility are demonstrated in the run chromatogram snapshot shown in FIGS. 12-14. The recovery and five CQAs analyzed for the capture eluate were comparable between the 3 columns, as well as over the entire period of continuous harvest capture (FIG. 16). These results demonstrate the feasibility of the direct continuous recombinant therapeutic monoclonal antibody capture from a perfusion bioreactor using a two PCC system, yielding consistent process performance indicators and CQAs over a prolonged period of time. A model recombinant therapeutic monoclonal antibody was used to study the feasibility of fully continuous bioprocessing platform using an integrated two PCC system.

Proof of Concept Using a MAb

Cell Culture

Figure 11:
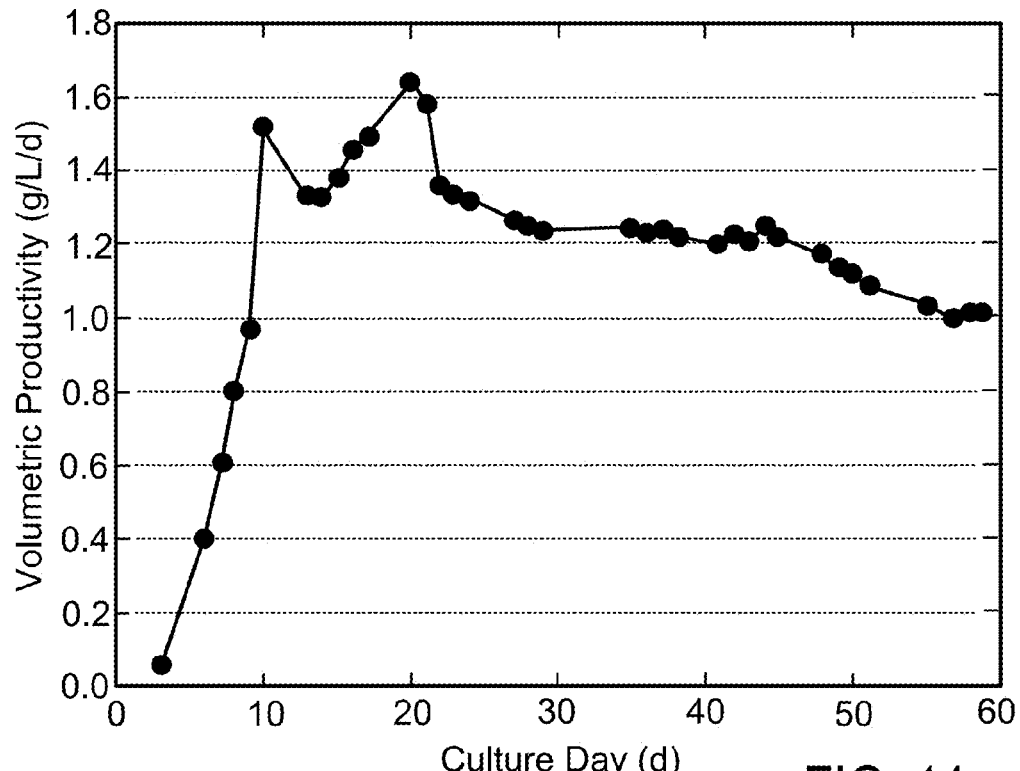
FIG. 11 is a graph of the volumetric productivity rate over time of the bioreactor culture producing the recombinant therapeutic monoclonal antibody.
Figure 12:
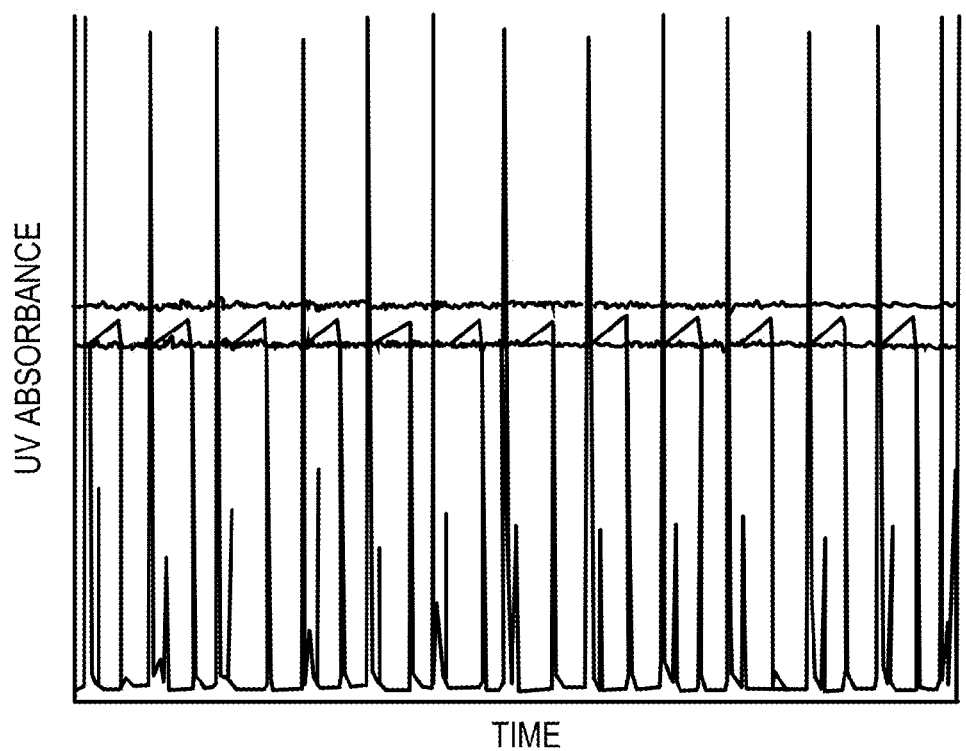
FIG. 12 is a graph of the real-time UV profile of the Protein A capture columns over a limited time window. Every third peak of every three peaks represents the column 1 outlet UV absorbance, every second peak of every three peaks represents the column 2 UV outlet absorbance, every first peak of every three peaks represents the column 3 UV absorbance.

The model recombinant therapeutic monoclonal antibody for this study was produced continuously over a 59-day period in a 12-L perfusion bioreactor under the conditions described in Materials and Methods. The volumetric productivity was maintained between 1.0-1.6 g/L from day 10 through day 59. The peak volumetric productivity was ~8 fold higher than the fed batch process using the same cell line, with a significant upward potential for the continuous process by optimizing perfusion rate and/or increasing the steady state cell density (FIGS. 11 and 12). It should be noted that the objective of the study was to demonstrate the functionality of the integrated continuous system. In fact, the volumetric production rate change allowed for the testing of the robustness of the PCC systems and, particularly, its ability to handle variability in harvest titer.

Downstream

Figure 13:
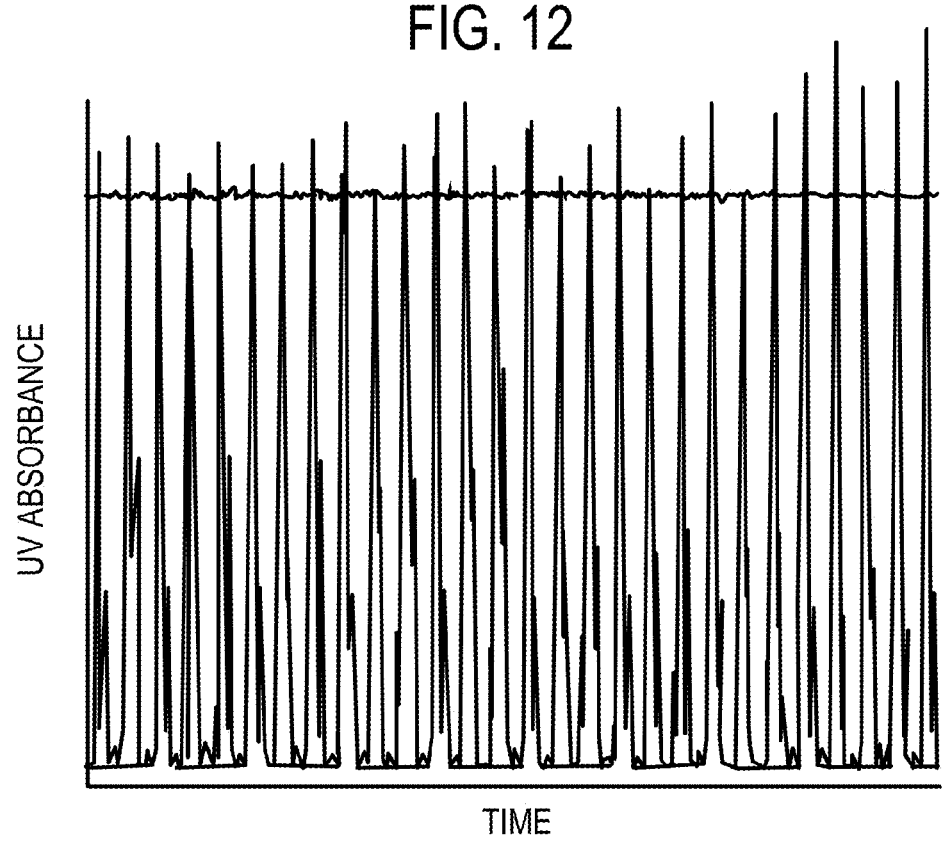
FIG. 13 is a graph of the real-time UV profile of the Capto-S columns over a limited time window. The dashed black line represents the feed UV absorbance, every third peak of every three peaks represents the column 1 outlet UV absorbance, every second peak of every three peaks represents the column 2 UV outlet absorbance, and every first peak of every three peaks represents the column 3 UV absorbance.
Figure 14:
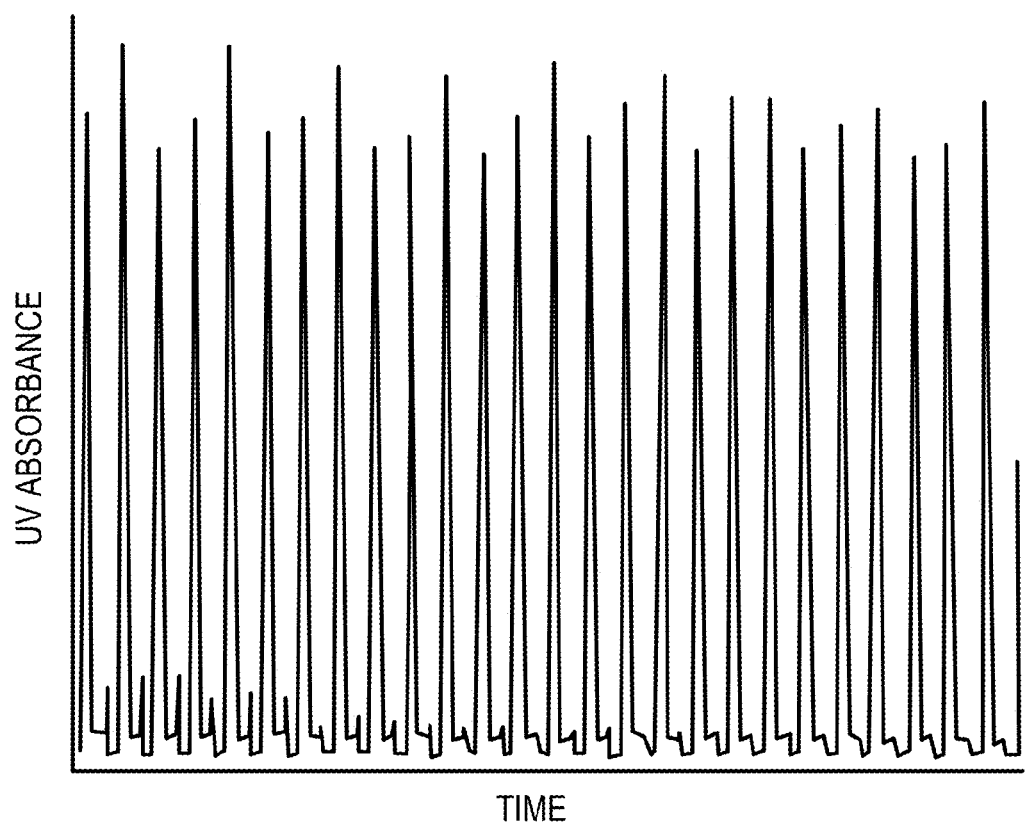
FIG. 14 is a graph of the real-time UV profile of the Sartobind Q-membrane over a limited time window.
Figure 15:
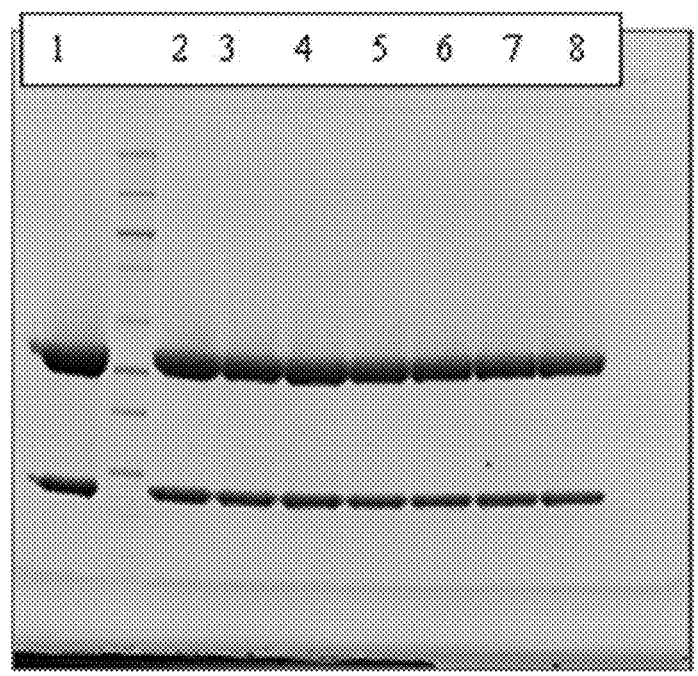
FIG. 15 is a sodium dodecyl sulfate polyacrylamide electrophoresis gel of a reference amount of the recombinant monoclonal antibody (lane 1), and the eluate of the two-PCC system obtained at days 1, 10, 15, 20, 25, 30, or 31 of production (lanes 3-9, respectively).

The main objective was to demonstrate the performance of the continuous bioprocessing platform with a recombinant therapeutic monoclonal antibody using an integrated two PCC system over an extended period of time. The column/membrane size and residence time for both the Protein A and the cation exchange column were scaled to achieve continuous processing of the bioreactor harvest to unformulated drug substance (DS). The integrated system was operated continuously for 31 days which corresponds to 15 independent unformulated DS batches (batch is defined as 1.25 days of processing, 15 Q-membrane filtrates or 0.8 g of DS), without any signs of time-based performance decline. The feed UV profile, the 3-column outlet UV profiles for protein A capture and Capto-S, as well as Sartobind Q membrane filtrates, were constant for the entire duration of the integrated bioreactor-PCC1-PCC2 operation (FIGS. 12-14). Additionally, all CQAs for unformulated DS were consistent for the entire duration of the PCC operation (FIGS. 15 and 16). The advantages of using the integrated continuous two PCC system for production of recombinant therapeutic monoclonal antibody as compared to the existing batch purification processes include an increase in the volumetric productivity, an increase in the chromatography media capacity utilization, a decrease in the volume of buffer usage, and a decrease in the volume of the individual column size.

Implementation of the fully Continuous Biomanufacturing Platform

Currently, there are two dominant platforms for biopharmaceutical manufacturing: (1) perfusion bioreactors, and (2)

fed-batch bioreactors for production of stable proteins. In both cases, non-limiting exemplary systems described herein provide for a bioreactor operation followed by multiple batch unit operations, including clarification, capture, polishing chromatography, and hold steps. The exemplary fully continuous production technology described in this Example allows for streamlined recombinant therapeutic protein production. As demonstrated in this Example, this exemplary system in combination with high producing clones and chemically-defined media can achieve very high cell density and volumetric productivity while operating at steady state. As a result, sufficient production capacity can be achieved with smaller bioreactors (<500 L) versus traditional processes where reactor scales exceed 10,000 L. The use of the ATF cell separation device eliminates the clarification unit operation. Most importantly, the direct integration of the fully continuous production makes harvest hold tanks obsolete, and replaces the large batch capture column with up to 2 orders-of-magnitude smaller columns used in the continuous system. Furthermore, continuous processing of the harvested liquid culture medium confers significant advantages with respect to recombinant therapeutic protein quality. Specifically, elimination of the harvest and other hold steps decreases target recombinant therapeutic protein exposure to enzymatic, chemical, and physical degradation, and thereby mitigates recombinant therapeutic protein stability risks. In summary, the successful development of the fully continuous bioprocessing platform at small scale for the manufacture of recombinant monoclonal antibodies opens up the potential for its large scale industrial implementation. These data show that the exemplary integrated, fully-continuous bioprocessing system offers unique advantages over traditional approaches for recombinant therapeutic protein manufacturing. For example, Tables 3 and 4 below list a few of the advantages provided by the exemplary process and system described in this Example.

TABLE 3

Exemplary Advantages of Two PCC System

| Parameters | Units | Batch | Continuous Processing Protein A column | Continuous Processing Capto-S column |
|---|---|---|---|---|
| Resin capacity | Normalized (%) | 100 | 120 | 110 |
| Buffer Usage | Normalized (%) | 100 | 75 | 80 |
| Column Volume | Normalized (%) | 100 | 3.9 (X3) | 4.7 (X3) |
| Diameter | Normalized (%) | 100 | 16 | 40 |
| Height | Normalized (%) | 100 | 47 | 30 |

TABLE 4

Exemplary Advantages of Two PCC System

| Parameters | Current Batch Process | Continuous Platform Process |
|---|---|---|
| Upstream Cycle Time | 1 BRX volume/14 days | 1 BRX volume/12 hours |
| Downstream Cycle Time | Days-Months | ~10 hours |
| Volumetric Productivity (g/L-Day) | ~0.1-0.2 | ~1.2 |
| Automation | Batch mode, discrete unit ops | Fully automatic |
| Total Number of downstream unit Operations | 9 (harvest, Centrifugation dept filtration, Pro A, VI, Capto S, Capto Q, viral filtration, sterile filtration) | 3 (PCC1, PCC2 and Viral filtration) |
| Hold Steps | 9 | None |

Example 3

Exemplary Two-PCC System that includes a 500-L Bioreactor

The method and system described below can be used to perform continuous bioprocessing of a recombinant therapeutic protein harvested from a 500-L bioreactor culture.

Materials and Methods

Cell Culture

Bioreactors with a working volume of 500-L are operated in perfusion mode utilizing the ATF (Refine Technologies) cell retention system with polyethersulfone 0.2-μm filters. Sintered spargers (20-μm) are used for $O_2$ gas to maintain the dissolved $O_2$ set point, and drilled-hole spargers (990-μm) are used for $N_2$ gas to maintain the $pCO_2$ set point. Cell density in the cell culture is monitored by offline measurements (Vi-CELL, Beckman Coulter, Brea, Calif.) and/or via online capacitance probes (Futura, Aber Instruments, Grand Island, N.Y.).

The bioreactor cell culture process runs utilize chemically-defined culture media and Chinese hamster ovary (CHO) cell lines that secrete recombinant antibodies or recombinant human enzymes. The cell concentration in the bioreactor culture immediately following inoculation is 0.5×$10^6$ cells/mL. The cells are allowed to grow to 50-60×$10^6$ cells/mL. Once the culture reach this cell density, cell-bleeding methods are initiated to maintain cell density at a steady state. Perfusion of the cell culture begins at 24-h after inoculation, at 1 reactor volume/day, with the rate of perfusion increased proportional to the cell concentration in the culture. A steady-state cell specific perfusion rate of 0.04-0.05 nL/cell-d is maintained. Dissolved $O_2$ in the bioreactor is kept above 30% of air saturation. pH in the culture medium is maintained between 6.8 and 6.95 through sodium carbonate addition. Antifoam (FoamAway, GIBCO, Grand Island, N.Y.) is added to the liquid culture medium to control foam levels. The liquid culture medium obtained from the bioreactors is pumped onto the single PCC system without additional clarification.

Periodic Counter-Current (PCC) Chromatographic Systems

The PCC systems to be used in these experiments are custom-modified ÄKTA (GE Healthcare, Piscataway, N.J.) system capable of running up to four columns. The system is equipped with five UV monitors (UV-900), three pumps (P-900), multiple valves (PV-908, SV-903), one pH and one conductivity meter (pH/C-900), and Unicorn-based custom software (GE Healthcare, Piscataway, N.J.). The first PCCS is a four-column PCCS, where the first three columns contain a protein A binding resin and perform the unit operation of capturing the recombinant therapeutic protein from a fluid, and the fourth column performs the unit operation of inactivating viruses present in a fluid (e.g., capable of holding the fluid for about 1 hours at a pH of 3.75). The second PCCS contains a total of three chromatography columns that perform the unit operation of purifying the recombinant therapeutic protein (containing a cationic exchange resin) and one chromatographic membrane that performs the unit operation of polishing (containing a cationic exchange resin). The specific flow rates and other properties of the first and second PCC systems to be used to continuously produce a recombinant protein drug substance are shown in Tables 5 and 6, respectively.

TABLE 5

Operational Parameters for the First PCCS

| Step description | Parameter | Value |
|---|---|---|
| Capture by protein A column | Column size | (3 columns); 1.6 L resin volume |
| | Load Titer | 0.6 mg/mL |
| | Load Flow rate | 0.36 CV/min |
| | Column residence time | 2.8 min |
| | Total time of capture per column | 5.4 hours (325 min) |
| | Load solo column | 75 min |
| | Load on two columns in series | 135 min (1.5 L) |
| | Elution flow rate | 0.13 CV/min |
| | Elution volume | 5 column volumes (CV) |
| | Elution time | 40 min |
| | Wash 1 volume | 4 CV |
| | wash 1 Time | 19 min |
| | Wash 2 volume | 6 CV |
| | wash 2 time | 28 min |
| | Regeneration volume | 3 CV |
| | Regeneration Time | 28 min |
| | protein Conc of the eluate | ~8 mg/mL |
| | Δ UV cut off 1 (t1) | 3 percenrt |
| | Δ UV cut off 2 (t2) | 70 percent |
| | percent recovery | 75 |
| Low pH hold | Time for hold | 60 min |
| | Hold pH | 3.75 |
| Buffer adjustment for S column load (In-line adjustment 1) | Flow rate of Protein A eluate transfer to PCC 2 | 0.5 CV/min |

TABLE 6

Operational Parameters for the Second PCCS

| Purifcation by Capto-S column | Column size | (3 columns); 335 mL resin volume |
|---|---|---|
| | Flow rate of transfer of S-load | 0.1 CV/min |
| | Load Titer | ~7 mg/mL |
| | Load Flow rate | 0.1 CV/min |
| | Load solo column | 86 min |
| | Load on two columns in series | 22 min |
| | Wash 1 volume | 2.5 CV |
| | wash 1 Time | 5 min |
| | Wash 2 volume | 2.5 CV |
| | wash 2 time | 5 min |
| | Elution flow rate | |
| | Elution volume | 17 CV |
| | Elution time | 40 min |
| | Regeneration volume | 5 CV |
| | Regeneration Time | 10 min |
| | protein Conc of the eluate | ~4.5 mg/mL |
| | Δ UV cut off 1 (t1) | 3 percenrt |
| | Δ UV cut off 2 (t2) | 70 percent |
| | percent recovery | 90 percenrt |
| In-line buffer dilution | Elution flow rate of adjustment buffer | 0.07 CV/min |
| sartobind Q membrane polish step | membrane volume | 350 mls |
| | membrane equilibration flow rate | 5 membrane vol/min |
| | Time of equilibration | 10 min |
| | Load of Q-membrane flow rate | 0.5 membrane vol/min |
| | Load time | |

TABLE 6-continued

Operational Parameters for the Second PCCS

| Chase flow rate | 5 membrane vol/min |
|---|---|
| Chase time | 2 min |
| Regeneration flow rate | 5 membrane vol/min |
| Regeneration time | 10 min |
| Pertcent Recovery | 95 |
| Protein concentration of the final therapeutic drug substance | ~3.5 mg/mL |

Breakthrough Curves

Protein breakthrough curves are required to determine the appropriate column switching strategy for each PCC system. To obtain breakthrough curves under the capture conditions, frontal loading experiments are performed. The dynamic binding capacity (DBC) is evaluated as a function of residence time using clarified harvest and breakthrough profiles measured by UV absorbance (280 nm). Column sizes of 6.0-mL and 1.0-mL are used for the determination of DBC for recombinant therapeutic antibodies and recombinant therapeutic human enzyme, respectively. The residence times are selected such that they are sufficiently long to satisfy the binding capacity requirements, while also ensuring that the loading time is longer than the rest of the column operations (wash, elution, regeneration, etc.).

Integration of the Single PCC System to the Bioreactor

In PCC systems, the residence time (RT) of the protein on the column can be decreased without increasing the column size because the breakthrough from the first column in the system can be captured on the second column in the system. This unique feature is used to design a continuous process such that the culture harvest could be processed at any perfusion rate (D) by varying the column volume (V) and RT, as outlined by Eq. 1:

$$V = D * RT \qquad (1)$$

To achieve continuous capture of the recombinant protein, the first single PCCS is directly connected to the bioreactor as shown in FIG. 2. The harvest from the bioreactor/ATF is pumped into a 2-L disposable bag serving as a small surge vessel (Hyclone, Logan, Utah) using a peristaltic pump (Masterflex, Cole-Parmer, Vernon Hills, Ill.). A 0.2-µm filter (Millipack 40, Millipore, Billerica, Mass.) is added between the bioreactor and the surge bag as an additional sterile barrier. MabSelect SuRe (GE Healthcare, Piscataway, N.J.) column is used to capture the recombinant therapeutic antibody and the recombinant therapeutic human enzyme, respectively). The operation of each column consists of equilibration, load, wash, elution, and regeneration steps. Since the engineering of the bench-scale single PCC system does not allow for closed operation, sodium azide is added to the process stream in-line.

Analytical Methods

Recombinant Antibodies

In-house assays are used for the quantitation of the titer of host cell proteins (HCP), aggregation, residual protein A, and potency of the recombinant antibodies. Titer is measured using a Protein A column (Applied Biosystems, Carlsbad, Calif.). Residual protein A and HCP are quantitated by ELISA using antigen and antibodies produced in-house. Aggregation is measured by HPLC-SEC using a TSK-GEL, G3000SWXL, 7.8 mM×30 cm, 5-µm column (TOSO HAAS, King of Prussia, Pa.). Recombinant antibody potency is measured by an in vitro cell-based assay.

Basic Concepts of the Single PCC System

A column operation generally consists of the load, wash, eluate, and regeneration steps. In each PCC system, multiple columns will be used to run the same steps discretely and continuously in a cyclic fashion. Since the columns are operated in series, the flow through and wash from one column is captured by a second column. This unique feature of PCC systems allows for the loading of the resin close to its static binding capacity instead of to the dynamic binding capacity, as is typical during batch-mode chromatography. For the ease of illustration, a 3-column system is used to describe this principle of PCC system operation (FIG. 3). A cycle is defined as three complete column operations resulting in three discrete elution pools. Once all the steps in a cycle are completed, the cycle is re-started. As a result, the feed stream is processed continuously in an operating PCC system, while recombinant therapeutic protein elution from each column is discrete and periodic.

Column Switching Strategy

To advance from one step to another within a PCC system cycle (FIG. 3), a column switching strategy is employed. There are two automated switching operations required per column in the PCC system, the first of which is related to the initial recombinant therapeutic protein breakthrough, while the second coincides with column saturation. Each single PCC system described in this example is operated using a control strategy utilizing dynamic UV monitoring. In general, column switching can be determined by any Process Analytical Technology (PAT) tool capable of in-line measurement of recombinant therapeutic protein concentration with feedback control. However, a PAT tool that operates in real time, such as UV, is ideal for providing the trigger signal for column switching.

FIG. 4 illustrates the principle of column switching based on the UV absorbance difference (ΔUV) between the feed inlet and column outlet. During column loading (Step 1; FIG. 3), the PCC control system determines the impurity baseline when the absorbance stabilizes. As the recombinant therapeutic protein breaks through (Step 2; FIG. 3), there is an increase in the outlet UV signal above the impurity baseline. At the point when ΔUV has reached a pre-determined threshold (such as 3% breakthrough of the recombinant therapeutic protein), the flow-through from column 1 is directed onto column 2 instead of to the waste (t1; FIG. 4). When column 1 is nearly saturated with recombinant therapeutic protein and the ΔUV has reached a pre-determined value (t2; FIG. 4), the feed is switched to column 2. An important advantage of this ΔUV-based column switching strategy is that it allows for uniform loading of the columns irrespective of the feed recombinant therapeutic protein concentration and the column capacity. Within a reasonable range, the strategy is adequate for harvest titer variability, thereby enhancing system robustness.

Accurate determination of the column-switching time, which is based on the UV absorbance difference between the feed and column outlet, is one of the critical elements of the each single PCC system real-time control strategy. This requires synchronization of all five UV detectors (one feed and four column outlet detectors) within a narrow range. The UV detectors are calibrated using a 3% acetone solution. The detector path lengths are manually adjusted so that all five absorbance values are within 0.5% of one another. The path length adjustment is ≤10%.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An integrated and continuous process for manufacturing a therapeutic protein drug substance, the process comprising:
   (i) culturing recombinant therapeutic protein-secreting cells in a perfusion bioreactor comprising a liquid culture medium under conditions that allow the cells to secrete the recombinant therapeutic protein into the medium, and wherein at least 90% cell-free volumes of the medium are continuously or periodically removed from the perfusion bioreactor and fed into a first periodic counter current chromatography system (PCCS1);
   (ii) capturing the recombinant therapeutic protein from the medium using the PCCS1, wherein an eluate of the PCCS1 comprising the recombinant therapeutic protein is continuously fed into a second periodic counter current chromatography system (PCCS2); and
   (iii) purifying and polishing the recombinant therapeutic protein using the PCCS2, wherein the purifying is performed using a resin in the PCCS2 that is different in chemical structure compared to the resin in the PCCS2 used to perform the polishing, and an eluate from the PCCS2 is the therapeutic protein drug substance; and
   wherein the process is integrated and runs continuously from the culturing step to the purifying and polishing step, and the elapsed time between feeding the medium into the PCCS1 and eluting the therapeutic protein drug substance from the PCCS2 is about 4 hours to about 9 hours.

2. The process of claim 1, wherein the PCCS1 performs at least two different unit operations.

3. The process of claim 2, wherein the use of the PCCS1 or the PCCS2, or both, includes column switching.

4. The process of claim 2, wherein the PCCS1 performs the unit operations of capturing the recombinant therapeutic protein and inactivating viruses.

5. The process of claim 1, wherein the PCCS1 or the PCCS2, or both, utilizes at least two chromatography columns.

6. The process of claim 1, wherein the PCCS1 comprises four chromatography columns, wherein three of the four chromatography columns in the PCCS1 perform the unit operation of capturing the recombinant therapeutic protein from the medium.

7. The process of claim 6, wherein the capturing is performed using affinity chromatography, cation exchange chromatography, anion exchange chromatography, or molecular sieve chromatography.

8. The process of claim 7, wherein the affinity chromatography is performed with a capture mechanism selected from the group consisting of: protein A-binding capture mechanism, substrate-binding capture mechanism, antibody-or antibody fragment-binding capture mechanism, aptamer-binding capture mechanism, and cofactor-binding capture mechanism.

9. The process of claim 8, wherein the affinity chromatography is performed with a protein A-binding capture mechanism, and the recombinant therapeutic protein is an antibody or an antibody fragment.

10. The process of claim 6, wherein an eluate comprising the recombinant therapeutic protein from the three of the four chromatography columns in the PCCS1 is fed into the fourth column of the PCCS1.

11. The process of claim 10, wherein the fourth chromatography column of the PCCS1 performs the unit operation of inactivating viruses by incubating the eluate from the three of the four chromatography columns in the PCCS1 at a pH of about 3.0 to 5.0.

12. The process of claim 11, further comprising adjusting the pH of an eluate comprising the recombinant therapeutic protein from the fourth chromatography column of the PCCS1 using an in-line buffer adjustment reservoir before the eluate from the fourth column of the PCCS1 is fed into the PCCS2.

13. The process of claim 12, wherein the PCCS2 comprises three chromatography columns and a chromatographic membrane, wherein the three chromatography columns in the PCCS2 perform the unit operations of purifying the recombinant therapeutic protein from the eluate from the fourth chromatography column of the PCCS1 through cation or anion exchange chromatography, and an eluate comprising the recombinant protein from the three chromatography columns in the PCCS2, is fed into the chromatographic membrane in the PCCS2.

14. The process of claim 13, wherein the chromatographic membrane in the PCCS2 performs the unit function of polishing the recombinant therapeutic protein present in the eluate from the three chromatography columns in the PCCS2 through cation or anion exchange chromatography.

15. The process of claim 14, wherein the chromatographic membrane in the PCCS2 performs the unit function of polishing through cation exchange chromatography.

16. The process of claim 1, further comprising formulating the therapeutic protein drug substance into a pharmaceutical composition.

17. The process of claim 1, wherein the recombinant therapeutic protein is an antibody or antibody fragment, an enzyme, an engineered protein, or an immunogenic protein or protein fragment.

18. The process of claim 1, wherein the entire process does not include storing the recombinant therapeutic protein in a break tank.

19. The process of claim 1, wherein the entire process includes storing the recombinant therapeutic protein in 1, 2, or 3 break tank(s).

20. The process of claim 19, wherein the 1, 2, or 3 break tank(s) are used to store the therapeutic protein for a total time period of about 5 minutes to about 4 hours.

21. The process of claim 19, wherein the 1, 2, or 3 break tank(s) has/have a volume of 1 mL to about 100 mL.

22. The method of claim 1, wherein the elapsed time between feeding the medium into the PCCS1 and eluting the therapeutic protein drug substance from the PCCS2 is greater than about 4 hours and is less than about 7 hours.

23. The method of claim 22, wherein the elapsed time between feeding the medium into the PCCS1 and eluting the therapeutic protein drug substance from the PCCS2 is greater than about 4 hours and is less than about 6 hours.

24. The method of claim 23, wherein the elapsed time between feeding the medium into the PCCS1 and eluting the therapeutic protein drug substance from the PCCS2 is greater than about 4 hours and is less than about 5 hours.

25. An integrated and continuous process for manufacturing a therapeutic protein drug substance, the process comprising:

(i) culturing recombinant therapeutic protein-secreting mammalian cells in a perfusion bioreactor comprising a liquid culture medium under conditions that allow the cells to secrete the recombinant therapeutic protein into the medium, and wherein at least 90% cell-free volumes of the medium are continuously or periodically removed from the perfusion bioreactor and fed from the perfusion bioreactor into a first periodic counter current chromatography system (PCCS1);

(ii) capturing the recombinant therapeutic protein from the medium using the PCCS1, wherein an eluate of the PCCS1 comprising the recombinant therapeutic protein is continuously fed into a second periodic counter current chromatography system (PCCS2); and (iii) purifying and polishing the therapeutic recombinant protein using the PCCS2, wherein the purifying is performed using a resin in the PCCS2 that is different in chemical structure compared to the resin in the PCCS2 used to perform the polishing, and an eluate from the PCCS2 is the therapeutic protein drug substance;

wherein:

the process is integrated and runs continuously from the culturing step to the purifying and polishing step, the entire process includes storing the recombinant therapeutic protein in a maximum of 1, 2, or 3 break tank(s), and the 1, 2, or 3 break tank(s) store(s) the therapeutic protein for a total time period of about 5 minutes to less than about 6 hours or has/have a volume of 1 mL to about 100 mL.

26. The method of claim 25, wherein the 1, 2, or 3 break tank(s) store(s) the therapeutic protein for a total time period of about 5 minutes to less than about 6 hours.

27. The method of claim 26, wherein the 1, 2, or 3 break tank(s) store(s) the therapeutic protein for a total time period of about 5 minutes to about 4 hours.

28. The method of claim 27, wherein the 1, 2, or 3 break tank(s) store(s) the therapeutic protein for a total time period of about 5 minutes to about 2 hours.

29. The method of claim 25, wherein the 1, 2, or 3 break tank(s) has/have a volume of 1 mL to about 100 mL.

30. The method of claim 29, wherein the 1, 2, or 3 break tank(s) has/have a volume of 1 mL to about 60 mL.

31. The method of claim 30, wherein the 1,2, or 3 break tank(s) has/have a volume of 1 mL to about 20 mL.

32. The method of claim 25, wherein the PCCS1 performs at least two different unit operations.

33. The process of claim 25, wherein the PCCS1 comprises four chromatography columns, wherein three of the four chromatography columns in the PCCS1 perform the unit operation of capturing the recombinant therapeutic protein from the medium.

34. The process of claim 33, wherein:

an eluate comprising the recombinant therapeutic protein from the three of the four chromatography columns in the PCCS1 is fed into the fourth column of the PCCS1, and the fourth chromatography column of the PCCS1 performs the unit operation of inactivating viruses by incubating the eluate from the three of the four chromatography columns in the PCCS1 at a pH of about 3.0 to 5.0.

35. The process of claim 34, wherein the PCCS2 comprises three chromatography columns and a chromatographic membrane, wherein the three chromatography columns in the PCCS2 perform the unit operations of purifying the recombinant therapeutic protein from the eluate from the fourth chromatography column of the PCCS1 through cation or anion exchange chromatography, and an eluate comprising the recombinant protein from the three chromatography columns in the PCCS2, is fed into the chromatographic membrane in the PCCS2.

36. The process of claim 35, wherein the chromatographic membrane in the PCCS2 performs the unit function of polishing the recombinant therapeutic protein present in the eluate from the three chromatography columns in the PCCS2 through cation or anion exchange chromatography.

37. The process of claim 25, further comprising formulating the therapeutic protein drug substance into a pharmaceutical composition.

* * * * *